United States Patent [19]
Otsuji et al.

[11] Patent Number: 5,391,806
[45] Date of Patent: Feb. 21, 1995

[54] HEAT-SENSITIVE RECORDING MATERIALS AND PHENOL COMPOUNDS

[75] Inventors: Atsuo Otsuji; Toshihiro Motoshima; Yoshimitsu Tanabe; Kiyoharu Hasegawa; Kazuyoshi Kikkawa; Masakatsu Nakatsuka; Akihiro Yamaguchi, all of Kanagawa, Japan

[73] Assignee: Mitsui Toatsu Chemicals, Incorporated, Tokyo, Japan

[21] Appl. No.: 131,549

[22] Filed: Oct. 5, 1993

Related U.S. Application Data

[62] Division of Ser. No. 901,486, Jun. 22, 1992, Pat. No. 5,270,281.

[30] Foreign Application Priority Data

| Jun. 21, 1991 | [JP] | Japan | 3-150419 |
| Jul. 26, 1991 | [JP] | Japan | 3-187399 |
| Jul. 26, 1991 | [JP] | Japan | 3-187415 |
| Dec. 11, 1991 | [JP] | Japan | 3-327546 |
| Dec. 20, 1991 | [JP] | Japan | 3-338416 |
| Dec. 24, 1991 | [JP] | Japan | 3-370770 |
| Mar. 2, 1992 | [JP] | Japan | 4-044534 |

[51] Int. Cl.$^6$ .......................... C07C 271/28
[52] U.S. Cl. .......................... 560/27; 560/9; 560/11; 558/234; 558/235; 558/241
[58] Field of Search .............. 560/9, 11, 27; 558/234, 558/235, 241

[56] References Cited

U.S. PATENT DOCUMENTS

| 3,639,341 | 2/1972 | Krimm et al. | 260/47 CZ |
| 4,316,042 | 2/1982 | Fünfschilling | 560/27 |
| 4,396,418 | 8/1983 | Schirmer et al. | 560/27 X |
| 4,405,358 | 9/1983 | Schirmer et al. | 560/27 X |
| 4,535,347 | 8/1985 | Glanz | 346/208 |
| 4,566,900 | 1/1986 | Plath et al. | 560/27 X |

FOREIGN PATENT DOCUMENTS

| 0035712 | 9/1981 | European Pat. Off. |
| 2190805 | 2/1974 | France |
| 43-4160 | 2/1968 | Japan |
| 45-14039 | 5/1970 | Japan |
| 56-144193 | 11/1981 | Japan |
| 57-193388 | 11/1981 | Japan |
| 58-211494 | 12/1983 | Japan |
| 60-56588 | 4/1985 | Japan |
| 60-225789 | 11/1985 | Japan |
| 63-7958 | 2/1988 | Japan |

(List continued on next page.)

*Primary Examiner*—Richard L. Raymond
*Attorney, Agent, or Firm*—Millen, White, Zelano & Branigan

[57] ABSTRACT

Heat-sensitive recording materials contain an electron-donating chromogenic compound and an electron-attracting compound. The recording materials also contain at least one compound represented by the following formula:

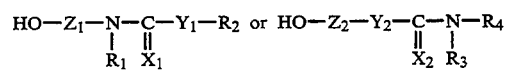

wherein $R_1$ and $R_3$ mean a hydrogen atom or an alkyl, aralkyl or aryl group, $R_2$ and $R_4$ denote an alkyl, alkenyl, aralkyl or aryl group, $X_1$, $X_2$, $Y_1$ and $Y_2$ stand for an oxygen or a sulfur atom, and $-Z_1-$ and $-Z_2-$ are a specific aromatic group. Also provided are phenol compounds represented by the following formula:

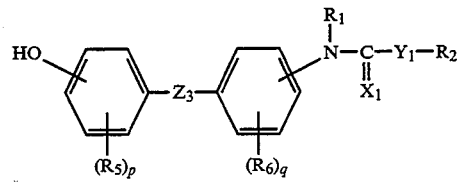

wherein $R_1$, $R_2$, $X_1$ and $Y_1$ have the same meanings as defined above; $R_5$ and $R_6$ are a hydrogen or halogen atom or an alkyl, alkoxy, aralkyl, aryl or hydroxyl group; p and q stand for an integer of 1-4; $R_5$ and $R_6$ may be either the same or different when p and q represent an integer of 2 or greater; and $-Z_3-$ means a specific divalent group.

20 Claims, No Drawings

FOREIGN PATENT DOCUMENTS

| | | |
|---|---|---|
| 63-30878 | 6/1988 | Japan . |
| 63-42590 | 8/1988 | Japan . |
| 1583 | 1/1989 | Japan . |
| 30640 | 6/1989 | Japan . |
| 18084 | 1/1990 | Japan . |
| 11437 | 3/1990 | Japan . |
| 31678 | 7/1990 | Japan . |
| 59796 | 12/1990 | Japan . |
| 4-187491 | 7/1992 | Japan . |
| 2131189 | 6/1984 | United Kingdom . |

HEAT-SENSITIVE RECORDING MATERIALS AND PHENOL COMPOUNDS

This application is a division of application Ser. No. 07/901,486, filed Jun. 22, 1992, now U.S. Pat. No. 5,270,281.

BACKGROUND OF THE INVENTION

FIELD OF THE INVENTION

This invention relates to heat-sensitive recording materials, and especially to heat-sensitive recording materials capable of producing color images with improved storage stability. This invention is also concerned with novel phenol compounds, and in particular with novel phenol compounds useful as color-developing agents or additives for recording materials (for example, heat-sensitive recording materials) or as monomers or additives for high molecular materials.

Heat-sensitive recording materials making use of the color-producing reaction between an electron-donating chromogenic compound and an electron-attracting compound (color-developing agent) have been well known conventionally (for example, Japanese Patent Publication Nos. 4160/1968 and 14039/1970). These heat-sensitive recording materials are relatively inexpensive and, moreover, have the merit that recording equipment therefor are compact and maintenance-free. They have hence found utility in a wide variety of fields such as facsimiles, recorders and printers.

As electron-attracting compounds, phenol compounds are widely used. Among these, 2,2-bis(4'-hydroxyphenyl)propane (also called "bisphenol A") is extensively used for its availability at low cost. Bisphenol A is, however, accompanied by the drawback that heat-recording materials using bisphenol A as an electron-attracting compound cannot produce color images with good storage stability. In addition, heat-sensitive recording materials with bisphenol A as an electron-attracting compound also involve the drawback that their color-producing sensitivity is low. Heat-sensitive recording materials using, as an electron-attracting compound, a phenol compound other than bisphenol A have also been proposed, for example, 4-hydroxybenzoate esters (Japanese Patent Laid-Open No. 144193/1981 and Japanese Patent Publication No. 30640/1989), aralkyloxyphenols (Japanese Patent Publication No. 31678/1990 and Japanese Patent Laid-Open No. 225789/1985) and hydroxybenzophenones (Japanese Patent Laid-Open No. 193388/1982).

The use of 4-hydroxybenzoate esters, for example, benzyl 4-hydroxybenzoate as an electron-attracting compound, however, leads to the drawback that the density of a produced color image drops with time. It is also accompanied by the drawback that white crystals of benzyl 4-hydroxybenzoate are formed on the produced color image thereby to present a powdered appearance (the so-called "whitening phenomenon"). The use of aralkyloxyphenols, for example, 4-benzyloxyphenol as an electron-attracting compound also results in the drawback that the density of a produced color image drops as time goes on. When hydroxybenzophenones, for example, 4-hydroxybenzophenone is used as an electron-attracting compound, the resulting color image has poor storage stability (for example, hydrothermoresistance and waterproofness) so that they are not considered to have sufficient quality or properties for practical use.

On the other hand, heat-sensitive recording materials containing—as a method for improving the color-producing sensitivity—a thermofusible compound (sensitizer) in addition to an electron-donating chromogenic compound and an electron-attracting compound are also widely used. Proposed as thermofusible compounds include terphenyls (Japanese Patent Publication No. 7958/1988), benzyl 4-benzyloxybenzoate (Japanese Patent Publication No. 30878/1988), naphthol derivatives (Japanese patent Publication No. 42590/1988), aminophenol derivatives (Japanese Patent Laid-Open No. 211494/1983), benzylbiphenyls (Japanese Patent Publication No. 11437/1990), diaryloxyalkane derivatives (Japanese Patent Laid-Open Nos. 56588/1985 and 16888/1986), oxalate ester derivatives (Japanese Patent Laid-Open No. 1583/1989), etc. However, it is the current situation that, although heat-sensitive recording materials containing one or more of these thermofusible compounds have been improved to some extent in color-producing sensitivity, they are accompanied by the problem of the extremely poor storage stability of produced color images, said storage stability being usually still inferior to that of color images produced without the addition of any thermofusible compound.

Accordingly, there is now a strong demand for the provision of heat-sensitive recording materials free of the drawbacks or problems described above, namely, for the provision of heat-sensitive recording materials capable of producing color images with excellent storage stability and, further, heat-sensitive recording materials having good color-producing sensitivity and capable of producing color images with excellent storage stability.

SUMMARY OF THE INVENTION

An object of this invention is, therefore, to provide a heat-sensitive recording material significantly improved in the storage stability of resulting color images. Another object of this invention is to provide a heat-sensitive recording material which is good in color-producing sensitivity and is excellent in the storage stability of resulting color images. A further object of this invention is to-provide a novel phenol compound useful as a color-developing agent or an additive for heat-sensitive recording materials.

With a view toward meeting the demand described above, the present inventors have conducted extensive research on heat-sensitive recording materials and also on electron-attracting compounds and additives for heat-sensitive recording materials.

In one aspect of this invention, there is thus provided a heat-sensitive recording material containing an electron-donating chromogenic compound and an electron-attracting compound, comprising at least one of the compounds represented by the following formula

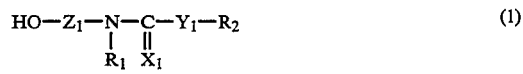

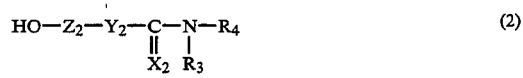

wherein $R_1$ and $R_3$ individually mean a hydrogen atom or an alkyl, aralkyl or aryl group, $R_2$ and $R_4$ individually denote an alkyl, alkenyl, aralkyl or aryl group, $X_1$, $X_2$, $Y_1$ and $Y_2$ stand for an oxygen or a sulfur atom, and —$Z_1$— and —$Z_2$ are a group represented by the following formulae (i) or (ii):

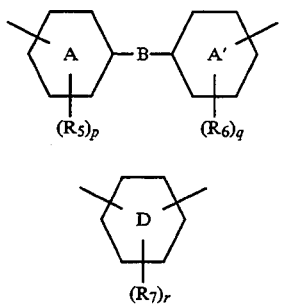

wherein $R_5$, $R_6$ and $R_7$ individually mean a hydrogen or halogen atom or an alkyl, alkoxy, aralkyl, aryl or hydroxyl group, p, q and r stand for an integer of 1-4, $R_5$, $R_6$ and $R_7$ may be either the same or different when p, q and r individually represent an integer of 2 or greater, the rings A and A' individually denote a benzene or naphthalene ring, the ring D represents a naphthalene ring, and —B—0 represents a group containing at least one group selected from the class consisting of —$R_8C$-$R_9$— (in which $R_8$ and $R_9$ individually represent a hydrogen atom or an alkyl, trifluoromethyl or aryl group or are combined together to form a ring), —O—, —S—, a phenylene group, —CO—, a single bond, —$C_mH_{2m}$—, m being an integer of 2-10, —$CR_{10}$=$CR_{11}$— (in which $R_{10}$ and $R_{11}$ are individually a hydrogen atom or an alkyl or aryl group), —SO—, and —$SO_2$—.

In another aspect of this invention, there is also provided a phenol compound represented by the following formula (3):

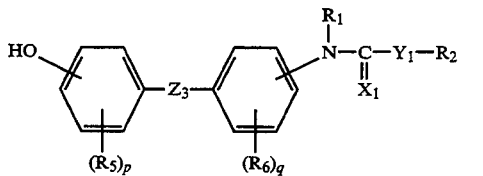

wherein $R_1$ means a hydrogen atom or an alkyl, aralkyl or aryl group, $R_2$ denotes an alkyl, alkenyl, aralkyl or aryl group, $R_5$ and $R_6$ are a hydrogen or halogen atom or an alkyl, alkoxy, aralkyl, aryl or hydroxyl group, p and q stand for an integer of 1-4, $R_5$ and $R_6$ may be either the same or different when p and q individually represent an integer of 2 or greater, $X_1$ and $Y_1$ individually represent an oxygen or sulfur atom, and —$Z_3$— means a group containing at least one group selected from the class consisting of —$R_8CR_9$— (in which $R_8$ and $R_9$ individually represent a hydrogen atom or an alkyl, trifluoromethyl or aryl group or are combined together to form a ring), —O—, —S—, a phenylene group, —CO—, —$C_mH_{2m}$—, m being an integer of 2-10, —$CR_{10}$=$CR_{11}$— (in which $R_{10}$ and $R_{11}$ are individually a hydrogen atom or an alkyl or aryl group), —SO— and —$SO_2$—.

The heat-sensitive recording material according to the present invention can promptly produce a color at low temperatures so that it is suitable for use in high-speed recording. Moreover, the color image so produced has excellent storage stability (heat resistance, hydrothermoresistance, waterproofness and oil resistance).

DETAILED DESCRIPTION OF THE INVENTION AND PREFERRED EMBODIMENTS

Where the ring A and/or the ring A' in the group represented by the formula (i) in the compound according to the present invention, said compound being represented by the formula (1) or (2), is a benzene ring, the position of substitution by each phenolic hydroxyl group and/or carbamate group substituted on the benzene ring may be preferably the ortho-, meta- or para-position, more preferably the meta- or para-position, both relative to the —B— group in the formula (i). Where the ring A and/or ring A' is a naphthalene ring, the position of substitution by each phenolic hydroxyl group and/or carbamate group substituted on the naphthalene ring may be preferably the 2-, 3-, 4-, 5-, 6-, 7- or 8-position when the —B— group is substituted to the 1-position (α-position) of the naphthalene ring. When the —B— group is substituted to the 2-position (β-position) of the naphthalene ring, on the other hand, the position of substitution by each phenolic hydroxyl group and/or carbamate group substituted on the naphthalene ring may be preferably the 1-, 3-, 4-, 5-, 6-, 7- or 8-position.

In the naphthalene ring in the group represented by the formula (ii), the positions of substitution by phenolic hydroxyl and/or carbamate groups may be on the same benzene ring or the different benzene rings in the naphthalene ring.

In the compound represented by the formula (1) or (2), $R_1$ and $R_3$ are a hydrogen atom or an alkyl, aralkyl or aryl group; preferably a hydrogen atom or a $C_{1-20}$ alkyl, $C_{5-14}$ cycloalkyl, $C_{7-20}$ aralkyl or substituted or unsubstituted phenyl group; more preferably a hydrogen atom or a $C_{1-4}$ alkyl, cyclopentyl, cyclohexyl, cycloheptyl, benzyl or phenyl group; still more preferably a hydrogen atom or a $C_{1-4}$ alkyl group; most preferably a hydrogen atom.

In the compound represented by the formula (1) or (2), $R_2$ and $R_4$ are an alkyl, alkenyl, aralkyl or aryl group; preferably a substituted or unsubstituted alkyl, substituted or unsubstituted cycloalkyl, substituted or unsubstituted alkenyl, substituted or unsubstituted cycloalkenyl, substituted or unsubstituted aralkyl, substituted or unsubstituted phenyl, substituted or unsubstituted naphthyl, or substituted or unsubstituted heteroaromatic group.

The alkyl and alkenyl groups represented by $R_2$ or $R_4$ may contain one or more substituents, for example, may be monosubstituted or multisubstituted by substituent(s) such as $C_{1-20}$ alkoxy, $C_{2-20}$ alkoxyalkyloxy, $C_{2-20}$ alkenyloxy, $C_{7-20}$ aralkyloxy, $C_{8-20}$ aralkyloxyalkoxy, $C_{6-20}$ aryloxy, $C_{7-20}$ aryloxyalkoxy and/or heteroatom-containing cycloalkyl group(s) and/or halogen atom(s).

Further, the aryl groups contained in these substituents may be substituted further by one or more $C_{1-6}$ alkyl, $C_{1-6}$ alkoxy, $C_{7-10}$ aralkyl, $C_{7-10}$ aralkyloxy and/or hydroxyl groups and/or one or more halogen atoms.

The aryl group in the aralkyl or aryl group represented by $R_2$ or $R_4$ may contain one or more substituents, for example, one or more $C_{1-20}$ alkyl, $C_{2-20}$ alkenyl, $C_{7-16}$ aralkyl, $C_{6-16}$ aryl, $C_{1-20}$ alkoxy, $C_{2-20}$ alkoxyalkyl, $C_{2-20}$ alkoxyalkyloxy, $C_{2-20}$ alkenyloxy, $C_{3-20}$ alkenyloxyalkyl, $C_{3-20}$ alkenyloxyalkyloxy, $C_{7-20}$ aralkyloxy, $C_{8-20}$ aralkyloxyalkyl, $C_{8-20}$ aralkyloxyalkyloxy, $C_{6-20}$ aryloxy, $C_{7-20}$ aryloxyalkyl, $C_{7-20}$ aryloxyalkyloxy, $C_{2-20}$ alkylcarbonyl, $C_{3-20}$ alkenylcarbonyl, $C_{8-20}$ aralkylcarbonyl, $C_{7-20}$ arylcarbonyl, $C_{2-20}$ alkoxycarbonyl, $C_{3-20}$ alkenyloxycarbonyl, $C_{8-20}$ aralkyloxycarbonyl, $C_{7-20}$ aryloxycarbonyl, $C_{2-20}$ alkylcarbonyloxy, $C_{3-20}$ alkenylcarbonyloxy, $C_{8-20}$ aralkylcarbonyloxy, $C_{7-20}$ arylcarbonyloxy, $C_{14-20}$ aralkyloxyaralkyl, $C_{1-20}$ alkylthio, $C_{7-20}$ aralkylthio, $C_{6-20}$ arylthio, nitro, formyl, hydroxyl and/or cyano groups and/or one or more halogen atoms.

The aryl groups contained in these substituents may be substituted further by one or more $C_{1-6}$ alkyl, $C_{1-6}$ alkoxy, $C_{7-10}$ aralkyl, $C_{7-10}$ aralkyloxy and/or hydroxyl groups and/or one or more halogen atoms.

Specific examples of $R_2$ and $R_4$ include methyl, ethyl, n-propyl, isopropyl, n-butyl, isobutyl, sec-butyl, tert-butyl, n-pentyl, isopentyl, n-hexyl, 2-ethylhexyl, n-octyl, n-nonyl, n-decyl, n-undecyl, n-dodecyl, n-tridecyl, n-tetradecyl, n-pentadecyl, n-hexadecyl, n-heptadecyl, n-octadecyl, cyclopentyl, cyclohexyl, 4-methylcyclohexyl, 2,5-dimethylcyclohexyl, 2,6-dimethylcyclohexyl, 3,4-dimethylcyclohexyl, 3,5-dimethylcyclohexyl, 3,3,5-trimethylcyclohexyl, 4-tert-butylcyclohexyl, cycloheptyl, cyclooctyl, cyclohexylmethyl, 2-cyclohexylethyl, bornyl, isobornyl, 2-norbornanemethyl, 1-adamantylmethyl, vinyl, allyl, 3-butenyl, 2-hexenyl, 3-hexenyl, 4-hexenyl, 5-hexenyl, 2-heptenyl, 6-nonenyl, 1-cyclohexenyl, cinnamyl, 2-methoxyethyl, 2-ethoxyethyl, 2-isopropoxyethyl, 2-n-butoxyethyl, 2-n-hexyloxyethyl, 3-methoxypropyl, 3-ethoxypropyl, 3-n-propoxypropyl, 3-n-butoxypropyl, 3-n-hexyloxypropyl, 3-cyclohexyloxypropyl, 2-methoxyethoxyethyl, 2-ethoxyethoxyethyl, 2-allyloxyethyl, 2-benzyloxyethyl, 2-phenethyloxyethyl, 2-(4'-methylbenzyloxy)ethyl, 2-(4'-chlorobenzyloxy)ethyl, 2-benzyloxymethoxyethyl, 2-phenoxyethyl, 2-(4'-chlorophenoxy)ethyl, 2-(4'-methylphenoxy)ethyl, 2-(4'-methoxyphenoxy)ethyl, 2-phenoxyethoxyethyl, 2-tetrahydrofurfuryl, 2-chloroethyl, 3-chloropropyl, 2,2,2-trichloroethyl, benzyl, α-methylbenzyl, α-ethylbenzyl, phenethyl, α-methylphenethyl, α,α-dimethylphenethyl, 4-(4'-methylphenethyl), 4-methylbenzyl, 3-methylbenzyl, 2-methylbenzyl, 4-isopropylbenzyl, 4-allylbenzyl, 4-benzylbenzyl, 4-phenethylbenzyl, 4-phenylbenzyl, 4-(4'-methylphenyl)benzyl, 4-methoxybenzyl, 4-n-butoxybenzyl, 3,4-dimethoxybenzyl, 4-methoxymethylbenzyl, 4-allyloxybenzyl, 4-vinyloxymethylbenzyl, 4-benzyloxybenzyl, 4-phenethyloxybenzyl, 4-phenoxybenzyl, 3-hydroxybenzyl, 2-hydroxybenzyl, 4-hydroxy-3-methoxybenzyl, 4-chlorobenzyl, 3-chlorobenzyl, 2-chlorobenzyl, 2-furfuryl, diphenylmethyl, phenyl, 1-naphthyl, 2-naphthyl, 3-furyl, 3-thienyl, 4-methylphenyl, 3-methylphenyl, 2-methylphenyl, 4-ethylphenyl, 3-ethylphenyl, 2-ethylphenyl, 4-n-propylphenyl, 4-isopropylphenyl, 4-n-butylphenyl, 4-sec-butylphenyl, 4-tert-butylphenyl, 4-n-pentylphenyl, 4-isopentylphenyl, 4-n-hexylphenyl, 4-n-octylphenyl, 4-tert-octylphenyl, 4-n-decylphenyl, 4-n-dodecylphenyl, 4-cyclopentylphenyl, 4-cyclohexylphenyl, 2-cyclohexylphenyl, 4-allylphenyl, 4-benzylphenyl, 2-benzylphenyl, 4-cumylphenyl, 4-(4'-methoxycumyl)phenyl, 4-(4'-chlorobenzyl)phenyl, 4-phenylphenyl, 3-phenylphenyl, 2-phenylphenyl, 4-( 4'-methoxyphenyl)phenyl, 2-(2'-methoxyphenyl)phenyl, 4-(4'-chlorophenyl)phenyl, 4-methoxyphenyl, 3-methoxyphenyl, 2-methoxyphenyl, 4-ethoxyphenyl, 2-ethoxyphenyl, 4-isopropoxyphenyl, 4-n-butoxyphenyl, 4-n-hexyloxyphenyl, 4-n-octyloxyphenyl, 4-n-dodecyloxypehenyl, 4-cyclohexyloxyphenyl, 1-(2-methylnaphthyl), 1-(4-methoxynaphthyl), 1- (4-n-butoxynaphthyl), 1-(5-ethoxynaphthyl), 2-(6-ethoxynaphthyl), 2-(6-n-hexyloxynaphthyl), 2-(7-methoxynaphthyl), 2-(7-n-butoxynaphthyl), 4-methoxymethylphenyl, 4-ethoxymethylphenyl, 4-n-butoxymethylphenyl, 3-methoxymethylphenyl, 4-(2'-methoxyethyl)phenyl, 4-(2'-ethoxyethyloxy)phenyl, 4-(2'-n-butoxyethyloxy)phenyl, 4-vinyloxyphenyl, 4-allyloxyphenyl, 4-(5'-pentenyloxy)phenyl, 1-(4-allyloxynaphthyl), 4-allyloxymethylph 4-(2'-allyloxyethyloxy)phenyl, 4-benzyloxyphenyl, 2-benzyloxyphenyl, 4-phenethyloxyphenyl, 4-(4'-chlorobenzyloxy)phenyl, 4-(4'-methylbenzyloxy)phenyl, 4-(4'-methoxybenzyloxy)phenyl, 1-(4-benzyloxy)naphthyl, 2-(6-benzyloxynaphthyl), 2-(7-benzyloxynaphthyl), 4-(benzyloxymethyl)phenyl, 4-(2'-benzyloxyethyloxy)phenyl, 4-phenoxyphenyl, 3-phenoxyphenyl, 4-(4'-methylphenoxy)phenyl, 4-(4'-methoxyphenoxy)phenyl, 4-(4-chlorophenoxy)phenyl, 1-(4-phenoxynaphthyl), 4-phenoxymethylphenyl, 4-(2'-phenoxyethyloxy)phenyl, 4-[2'-(4'-methylphenyl)oxyethyloxy]phenyl, 4-[2'-4'-methoxyphenyl)oxyethyloxy]phenyl, 4-[2'-(4'-chlorophenyl)oxyethyloxy]phenyl, 4-acetylphenyl, 2-acetylphenyl, 4-ethylcarbonylphenyl, 4-n-butylcarbonylphenyl, 4-n-hexylcarbonylphenyl, 4-n-octylcarbonylphenyl, 4-cyclohexylcarbonylphenyl, 1-(4-acetylnaphthyl), 4-allylcarbonylphenyl, 4-benzylcarbonylphenyl, 4-(4'-methylbenzyl)carbonylphenyl, 4-phenylcarbonylphenyl, 4-(4'-methylphenyl)carbonylphenyl, 4-(4'-chlorophenyl)carbonylphenyl, 1-(4-phenylcarbonylnaphthyl), 4-methoxycarbonylphenyl, 4-ethoxycarbonylphenyl, 4-n-propoxycarbonylphenyl, 4-n-butoxycarbonylphenyl, 4-n-hexyloxycarbonylphenyl, 4-n-decyloxycarbonylphenyl, 4-cyclohexyloxycarbonyphenyl, 1-(4-ethoxycarbonynaphthyl), 2-(6-methoxycarbonylnaphthyl), 2-(6-n-butoxycarbonylnaphthyl), 4-allyloxycarbonylphenyl, 4-benzyloxycarbonylphenyl, 4-phenethyloxycarbonylphenyl, 2-(6-benzyloxycarbonylnaphthyl), 4-phenyloxycarbonylphenyl, 4-(4'-ethylphenyl)oxycarbonylphenyl, 4-(4'-chlorophenyl)oxycarbonylphenyl, 2-(6-phenyloxycarbonylnaphthyl), 4-acetyloxyphenyl, 4-ethylcarbonyloxyphenyl, 4-n-propylcarbonyloxyphenyl, 4-n-pentylcarbonyloxyphenyl, 4-n-octylcarbonyloxyphenyl, 4-cyclohexylcarbonyloxyphenyl, 1-(4-acetyloxynaphthyl), 1-(5-acetyloxynaphthyl), 2-(6-ethylcarbonyloxynaphthyl), 4-allylcarbonyloxyphenyl, 4-benzylcarbonyloxyphenyl, 4-phenethylcarbonyloxyphenyl, 2-(6-benzylcarbonyloxynaphthyl), 4-phenylcarbonyloxyphenyl, 4-(4'-methylphenyl)carbonyloxyphenyl, 4-(2'-methylphenyl)carbonyloxyphenyl, 4-(4'-chlorophenyl)carbonyloxyphenyl, 4-(2'-chlorophenyl)carbonyloxyphenyl, 1-(4-phenylcarbonyloxynaphthyl), 2-(6-phenylcarbonyloxynaphthyl), 4-(4'-benzyloxy)cumylphenyl, 4-methylthiophenyl, 4-ethylthiophenyl, 4-n-butylthiophenyl, 4-n-hexylthiophenyl, 4-cyclohexylthiophenyl, 4-benzylthiophenyl, 4-(4'-chlorobenzylthio)phenyl, 4-phenylthiophenyl, 4-(4'-methylphenylthio)phenyl, 4-(4'-methoxyphenylthio)phenyl, 4-(4'-chlorophenylthio)phenyl, 1-(4-methylthionaphthyl), 2-(6-ethylthionaphthyl), 2-(6-phenylthionaphthyl), 4-fluorophenyl, 3-fluorophenyl, 2-fluorophenyl, 4-chlorophenyl, 3-chlorophenyl 2,-chlorophenyl, 4-bromophenyl, 1-(4-chloronaphthyl), 2-(4-chloronaphthyl), 2-(6-bromonaphthyl), 4-nitrophenyl, 3-nitrophenyl, 4-formylphenyl, 3-formylphenyl, 2-formylphenyl, 4-hydroxyphenyl, 3-hydroxyphenyl 2-hydroxyphenyl, 4-cyanophenyl, 2-cyanophenyl, 2-chloro-4-nitrophenyl, 4-chloro-2-nitrophenyl, 6-chloro-3-methylphenyl, 2-chloro-6-methylphenyl, 4-chloro-2-methylphenyl, 4-chloro-3-methylphenyl, 2,4-dimethylphenyl, 2,5-dimethylphenyl, 3,4-dimethylphenyl, 3,5-dimethylphenyl, 2,6-dimethylphenyl, 2,3,5-trimethylphenyl, 2,3,6-trimethylphenyl, 2,4,6-trimethylphenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4,6-trichlorophenyl, 2-methoxy-4-methylphenyl, 2,6-dimethoxyphenyl, 3,5-dimethoxyphenyl, 3,5-diethoxyphenyl, 3,5-di-n-butoxyphenyl, 3,4,5-trimethoxyphenyl, and 1-(2,4-dichloronaphthyl). $X_1$, $X_2$, $Y_1$ and $Y_2$ individually represent an oxygen atom or a sulfur atom.

In the formulae (i) and (ii), the ring A and ring A' individually represent a benzene ring or naphthalene ring while the ring D indicates a naphthalene ring. More preferably, the ring A and ring A' are each a benzene ring.

In the formulae (i) and (ii), p, q and r individually represent an integer of 1–4. When p, q and r individually represent an integer of 2 or greater, $R_5$, $R_6$ and $R_7$ may be either the same or different. Namely, when p (q or r) is 2, for example, two $R_5$s ($R_6$s or $R_7$s) may be the same alkyl group or different alkyl groups, or may be an alkyl group and a halogen atom, respectively.

In the formulae (i) and (ii), $R_5$, $R_6$ and $R_7$ individually represent a hydrogen or halogen atom or an alkyl, alkoxy, aralkyl, aryl or hydroxyl group; preferably a hydrogen, fluorine, chlorine or bromine atom or a $C_{1-20}$ alkyl, $C_{5-14}$ cycloalkyl, $C_{1-20}$ alkoxy, $C_{7-20}$ aralkyl, phenyl or hydroxyl group; more preferably a hydrogen, fluorine or chlorine atom or a $C_{1-4}$ alkyl, cyclohexyl, $C_{1-4}$ alkoxy, benzyl, phenyl or hydroxyl group, with a hydrogen atom being particularly preferred.

In the formula (i), —B— represents a group containing at least one group selected from the class consisting of —$R_8CR_9$— (in which $R_8$ and $R_9$ individually represent a hydrogen atom or an alkyl, trifluoromethyl or aryl group or are combined together to form a ring), —O—, —S—, a phenylene group, —CO—, a single bond, $C_mH_{2m}$—, m standing for an integer of 2–10, —$CR_{10}$=$CR_{11}$— (in which $R_{10}$ and $R_{11}$ are individually a hydrogen atom or an alkyl or aryl group), —SO—, and —$SO_2$—.

$R_8$ and $R_9$ individually represent a hydrogen atom or an alkyl, trifluoromethyl or aryl group or are combined together to form a ring, preferably a hydrogen atom, a $C_{1-20}$ alkyl, trifluoromethyl or phenyl group or a $C_{5-14}$ cycloalkane ring formed of $R_8$ and $R_9$; more preferably a hydrogen atom, a $C_{1-4}$ alkyl, trifluoromethyl or phenyl group, or a cyclopentane, cyclohexane, cycloheptane or cyclooctane ring formed of $R_8$ and $R_9$.

m stands for an integer of 2–10, with an integer of 2–6 being more preferred.

$R_{10}$ and $R_{11}$ individually represent a hydrogen atom or an alkyl or aryl group, preferably a hydrogen atom or a $C_{1-20}$ alkyl or phenyl group, more preferably a hydrogen atom or a $C_{1-4}$ alkyl group.

In particular, —B— is preferably a group containing at least one group selected from the class consisting of —$R_8CR_9$— (in which $R_8$ and $R_9$ individually represent a hydrogen atom or an alkyl, trifluoromethyl or aryl group or are combined together to form a ring), —O—, —S—, a phenylene group, —CO—, and a single bond. Of these, —$R_8CR_9$ (in which $R_8$ and $R_9$ individually represent a $C_{1-4}$ alkyl group) , —O—, —S—,

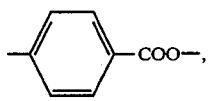

—OOC— and single bond are preferred.
Specific examples include

—$CH_2$—, —$CH_3CH$—, —$CH_3CCH_3$—,

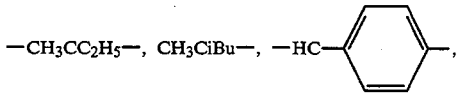

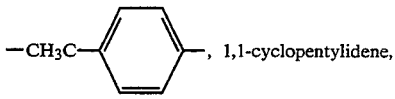, 1,1-cyclopentylidene, 1,1-cyclohexylidene, 1,1-cycloheptylidene, 1,1-cyclooctylidene, —$CF_3CCF_3$—, —O—, —S—, 1,4-phenylene, 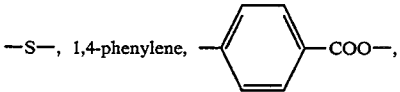

—COO—, —OOC—, single bond, —CO—,

—$(CH_2)_2$—, —$(CH_2)_3$—, —$(CH_2)_4$—, —CH=CH—,

—$CCH_3$=$CCH_3$—, —$CC_2H_5$=$CC_2H_5$—, —$OCH_2$—,

—$CH_2O$—, —$O(CH_2)_2O$—, —$O(CH_2)_3O$—,

—$O(CH_2)_4O$—, —$O(CH_2)_5O$—, —$O(CH_2)_6O$—,

—$CH_2CO$—, —$COCH_2$—, —$CH_2CH_2CO$—,

—$COCH_2CO$—, 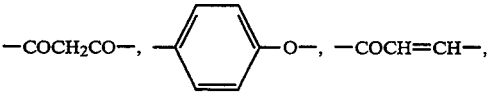, —COCH=CH—,

—$COOCH_2CO$—, —$CH_3CCH_3$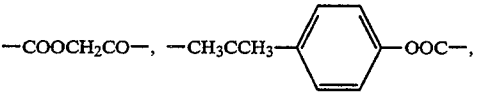OOC—, and

—$COOCH_2CH_2OOC$—.

In the formulae (1) and (2) of this invention, particularly preferred —$Z_1$— and —$Z_2$— are the groups represented by the following formulae (iii) to (ix), respectively:

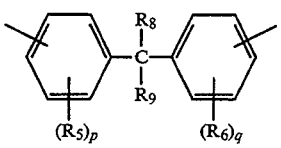 (iii)

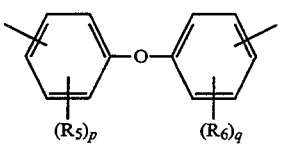 (iv)

-continued

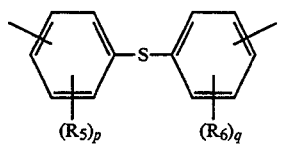 (v)

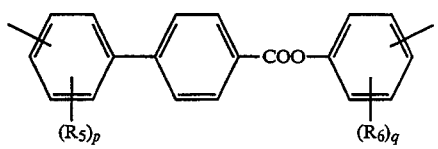 (vi)

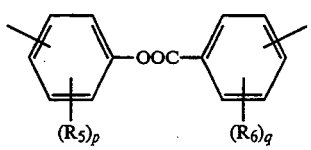 (vii)

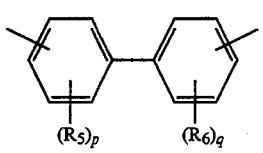 (viii)

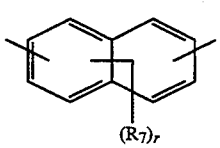 (ix)

wherein $R_5$, $R_6$, $R_7$, $R_8$, $R_9$, p, q and r have the same meanings as defined above.

Among the compounds according to this invention, which are represented by the formula (1), the compounds represented by the formula (3) are novel compounds found by the present inventors.

In the compounds represented by the formula (3) according to this invention, the position of substitution by each phenolic hydroxyl group or carbamate group is preferably the ortho-, meta- or para-position, more preferably the meta- or para-position, both relative to $-Z_3-$.

Of the compounds (3) according to the present invention, preferred examples include those represented by the following formula (3-a) to (3-i), respectively:

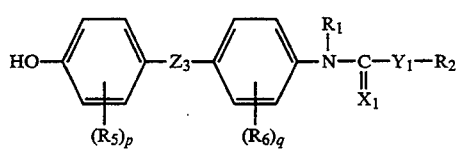 (3-a)

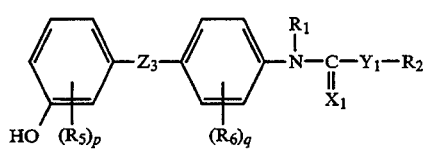 (3-b)

-continued

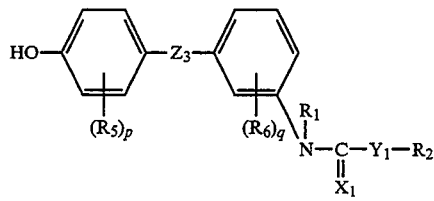 (3-c)

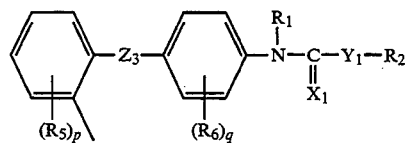 (3-d)

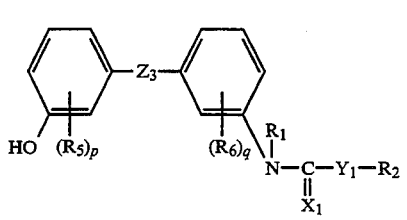 (3-e)

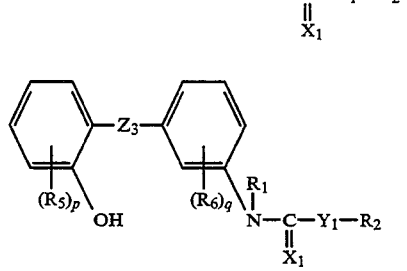 (3-f)

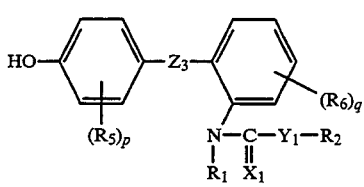 (3-g)

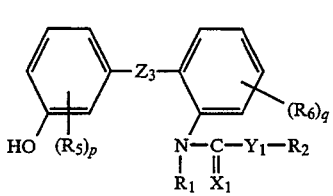 (3-h)

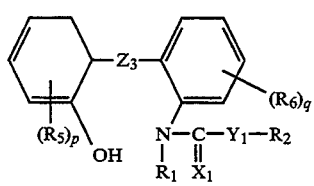 (3-i)

wherein $R_1$, $R_2$, $R_5$, $R_6$, $X_1$, $Y_1$, P and q have the same meanings as defined above.

In the formulae (3-a) to (3-i), examples of $R_1$, $R_2$, $R_5$, $R_6$, $X_1$, $Y_1$, P and q are as described above. In particular, $R_1$ is preferably a hydrogen atom or a $C_{1-4}$ alkyl group, notably a hydrogen atom, $R_5$ and $R_6$ are preferably a hydrogen atom or a $C_{1-4}$ alkyl group, notably a hydrogen atom, and $X_1$ is preferably an oxygen atom.

In the formulae (3-a) to (3-i), $-Z_3-$ represents a group containing at least one group selected from the class consisting of —$R_8CR_9$— (in which $R_8$ and $R_9$ individually represent a hydrogen atom or an alkyl, trifluoromethyl or aryl group or are combined together to form a ring), —O—, —S—, a phenylene group, —CO—, —$C_mH_{2m}$— (in which m stands for an integer of 2-10), —$CR_{10}=CR_{11}$— (in which $R_{10}$ and $R_{11}$ individually represent a hydrogen atom or an alkyl or aryl group), —SO—, and —$SO_2$—.

In —$Z_3$—, $R_8$ and $R_9$ may individually represent a hydrogen atom or an alkyl, trifluoromethyl or aryl group or may be combined together to form a ring; preferably a hydrogen atom, a $C_{1-20}$ alkyl, trifluoromethyl or phenyl group or a $C_{5-14}$ cycloalkane ring formed of $R_8$ and $R_9$; most preferably a hydrogen atom, a $C_{1-4}$ alkyl, trifluoromethyl or phenyl group, or a cycloheptane, cyclohexane or cyclopentane ring formed by $R_8$ and $R_9$. A methyl group is especially preferred. m stands for an integer of 2-10, more preferably an integer of 2-6. $R_{10}$ and $R_{11}$ individually represent a hydrogen atom or an alkyl or aryl group, preferably a hydrogen atom or a $C_{1-20}$ alkyl or phenyl group, more preferably a hydrogen atom or a $C_{1-4}$ alkyl group.

More preferred —$Z_3$— is a group containing at least one group selected from the class consisting of —$R_8CR_9$— (in which $R_8$ and $R_9$ individually represent a hydrogen atom or an alkyl, trifluoromethyl or aryl group or are combined together to form a ring), —O—, —S—, 1,4-phenylene and —CO—. Particularly preferred is a group containing at least one group selected from the class consisting of —$R_8CR_9$— (in which $R_8$ and $R_9$ individually represent a $C_{1-4}$ alkyl group), —O—, —S—,

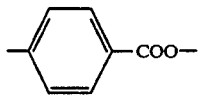

and —OOC—.

Among the compounds (3) according to the present invention, particularly preferred compounds are those represented by the following formulae (4) to (8), respectively:

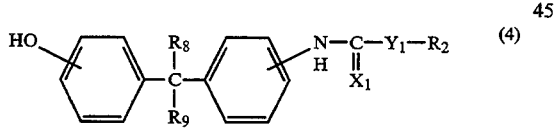

wherein $R_8$ and $R_9$ individually represent a $C_{1-4}$ alkyl group, and $R_2$, $X_1$ and $Y_1$ have the same meanings as defined above.

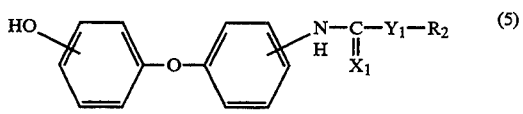

wherein $R_2$, $X_1$ and $Y_1$ have the same meanings as defined above.

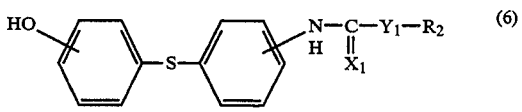

wherein $R_2$, $X_1$ and $Y_1$ have the same meanings as defined above.

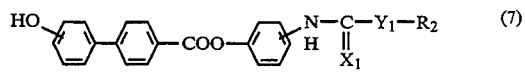

wherein $R_2$, $X_1$ and $Y_1$ have the same meanings as defined above.

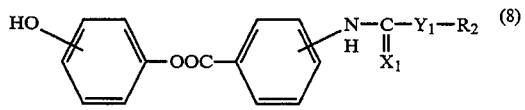

wherein $R_2$, $X_1$ and $Y_1$ have the same meanings as defined above.

Among the compounds represented by the formula (4), the compounds represented by the formula (4-1) or (4-2) are particularly preferred.

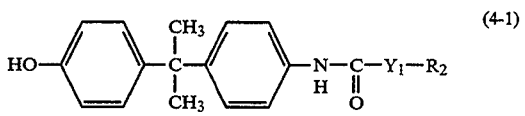

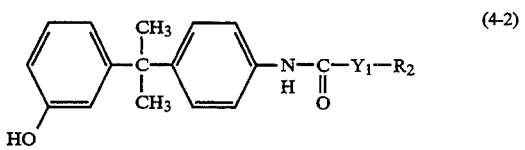

wherein $R_2$ and $Y_1$ have the same meanings as defined above.

Among the compounds represented by the formula (5), the compounds represented by the following formula (5-1) or (5-2) are particularly preferred.

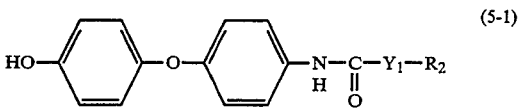

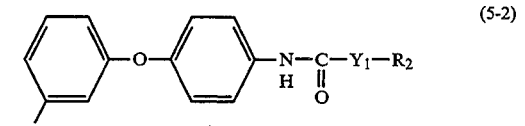

wherein $R_2$ and $Y_1$ have the same meanings as defined above.

Among the compounds represented by the formula (6), the compounds represented by the following formulae (6-1) are particularly preferred.

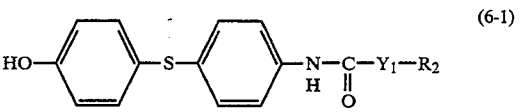

wherein $R_2$ and $Y_1$ have the same meanings as defined above.

Among the compounds represented by the formula (7), the compounds represented by the following formula (7-1) or (7-2) are particularly preferred.

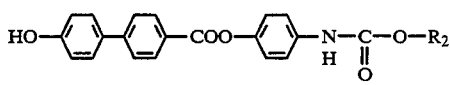 (7-1)

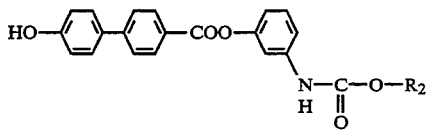 (7-2)

wherein $R_2$ has the same meaning as defined above.

Among the compounds represented by the formula (8), the compounds represented by the following formula (8-1) are particularly preferred.

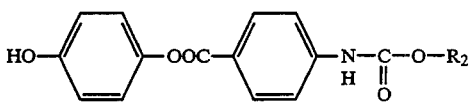 (8-1)

wherein $R_2$ has the same meaning as defined above.

The phenol compounds represented by the formula (1), (2) or (3), said compounds pertaining to the present invention, can be prepared in a manner known per se in the art [for example, the process disclosed in Methoden Der Organischen Chemie, 8, 137(1952), Shin Jikken Kagaku Koza (New Textbook of Experimental Chemistry), 14, 1658,1836, Maruzen (1977), or Angewandte Chemie International Edition, 6, 281(1967)].

The compounds represented by the formula (1), which pertain to the present invention, can each be prepared typically from an aminophenol derivative, which is represented by the following formula (a):

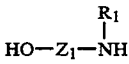 (a)

wherein $R_1$ and $Z_1$ have the same meanings as defined above, and a chloroformate ester, chlorothioformate ester or chlorodithioformate ester represented by the following formula (b):

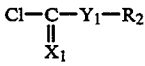 (b)

wherein $R_2$, $X_1$ and $Y_1$ have the same meanings as defined above.

The compounds represented by the formula (2), which relate to the present invention, can each be prepared typically from a phenol derivative, which is represented by the following formula (c);

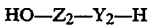 (c)

wherein $Y_2$ and $Z_2$ have the same meanings as defined above, and from an isocyanate or thioisocyanate derivative, which is represented by the following formula (d):

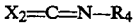 (d)

wherein $R_4$ and $X_2$ have the same meanings as defined above, or a chloroformic amide derivative represented by the following formula (e):

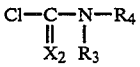 (e)

wherein $R_3$, $R_4$ and $X_2$ have the same meanings as defined above.

The novel phenol compounds represented by the formula (3), which also relate to the present invention, can each be prepared typically from an aminophenol derivative, which is represented by the following formula (aa):

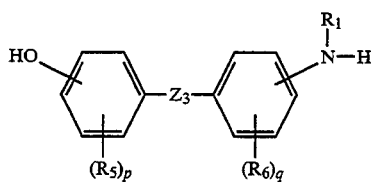 (aa)

wherein $R_1$, $R_5$, $R_6$, $Z_3$, p and q have the same meanings as defined above, and a chloroformate ester, chlorothioformate ester or chlorodithioformate ester represented by the above formula (b).

The aminophenol derivative useful as a raw material upon preparation of the novel phenol compound (3) of the present invention can be prepared in a manner known per se in the art.

For example, an aminophenol derivative, which is represented by the following formula (4-a):

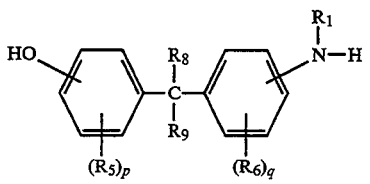 (4-a)

wherein $R_1$, $R_5$, $R_6$, $R_8$, $R_9$, p and q have the same meanings as defined above, can be prepared in a manner known per se in the art, for example, in accordance with the process disclosed in Journal of American Chemical Society, 68, 2600 (1946), British Patent 1,028,156, Japanese Patent Laid-Open No. 114942/1987, 116546/1987 or 172364/1989, or the like, namely, by decomposing the diazonium salt of a corresponding dianilinoalkane, by reacting a corresponding diphenol alkane with a corresponding aniline, by reacting a corresponding monoalkenylaniline with a corresponding phenol in the presence of a catalyst, or by reacting a corresponding monoalkenylphenol and a corresponding aniline in the presence of a catalyst.

Further, aminophenol derivatives represented by the following formula (5-a):

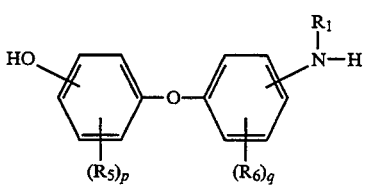 (5-a)

wherein $R_1$, $R_5$, $R_6$, p and q have the same meanings as defined above can each be prepared in a manner known per se in the art, for example, in accordance with the process disclosed in Pharmaceutical Bulletin, 5, 397 (1952), Journal of the Society of Synthetic Organic Chemistry, Japan, 24, 44 (1966), U.S. Pat. No. 3,240,706 or the like, namely, by, for example, reacting a nitrochlorobenzene with a dihydroxybenzene in the presence of a base and then reducing the resultant nitrophenoxyphenol.

Aminophenol derivatives represented by the following formula (6-a):

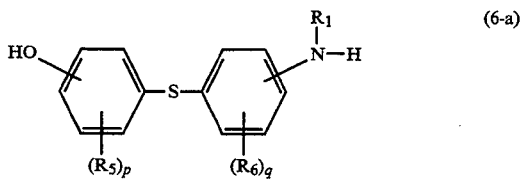

wherein $R_1$, $R_5$, $R_6$, p and q have the same meanings as defined above can each be prepared in a manner known per se in the art, for example, in accordance with the process disclosed in Indian Journal of Chemistry, 15B, 661 (1977), U.S. Pat. No. 3,443,943 or the like, namely, by reacting a nitrochlorobenzene with a hydroxythiophenol in the presence of a base and then reducing the resultant hydroxyphenyl-nitrophenyl sulfide.

In addition, aminophenol derivatives represented by the following formula (7-a):

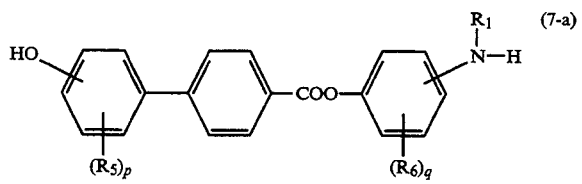

wherein $R_1$, $R_5$, $R_6$, p and q have the same meanings as defined above can each be prepared in a manner known per se in the art, for example, in accordance with the process disclosed in Japanese Patent Laid-Open No. 14441/1974 or the like, namely, by reacting a hydroxybiphenylcarboxylic acid with a nitrophenol in the presence of a catalyst and then reducing the resultant nitrophenyl hydroxybiphenylcarboxylate.

Aminophenol derivatives represented by the following formula (8-a):

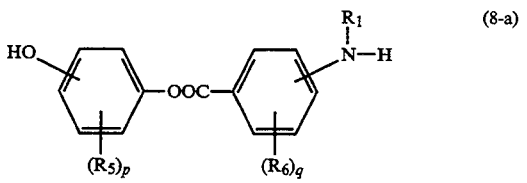

wherein $R_1$, $R_5$, $R_6$, p and q have the same meanings as defined above can each be prepared in a manner known per se in the art, for example, in accordance with the process disclosed in Journal of Organic Chemistry, 37, 1425 (1972), Journal of Organic Chemistry, 38, 3160 (1973) or the like, namely, by reacting a dihydroxybenzene with a nitrobenzoic acid and then reducing the resultant hydroxyphenyl nitrobenzoate.

Furthermore, the compounds represented by the formula (b) can each be prepared in a manner known per se in the art, for example, in accordance with the process disclosed in Methoden Der Organischen Chemie, 8, 101 (1952), Journal of American Chemical Society, 72, 1254 (1950), Angewandte Chemie International Edition, 4, 281 (1967), Chemical Review, 73, 75 (1973) or the like, namely, by the reaction between phosgene or thiophosgene and an alcohol, phenol, thiol or thiophenol.

Upon production of the phenol compound (3) of the present invention, a conventional reaction process can be employed for the reaction between the aminophenol derivative represented by the formula (aa) and the compound represented by the formula (b). For example, they can be reacted by adding the compound (b) dropwise to the compound (aa) under stirring. Upon conducting the reaction, the molar ratio of the compound (aa) to the compound (b) is generally in a range of about 1 to about 0.5–2, preferably in a range of about 1 to about 0.8–1.5, more preferably in a range of about 1 to about 0.8–1.2.

Although the reaction may be conducted in a solventless manner, it is generally more preferable to carry it out using a solvent.

Examples of solvents usable in the reaction include hydrocarbon solvents such as hexane, octane, benzene, toluene and xylene; ketone solvents such as acetone, methyl ethyl ketone, methyl isobutyl ketone and cyclohexanone; ester solvents such as ethyl acetate, butyl acetate and amyl acetate; ether solvents such as diethyl ether, diisopropyl ether, dibutyl ether, tetrahydrofuran and dioxane; halogenated solvents such as dichloromethane, chloroform, carbon tetrachloride, 1,2-dichloroethane, Perclene, chlorobenzene and dichlorobenzene; and mixed solvents thereof. The reaction can also be conducted in the presence of both one of the solvents or mixed solvents and water.

The reaction temperature generally ranges from 0° C. to 200° C., with about 0°–100° C. being preferred. The reaction time is generally in a range of from several minutes to several tens of hours although it varies significantly depending on reaction conditions such as reaction temperature.

During the reaction, hydrogen chloride is by-produced. Use of a dehydrochlorinating agent, for example, an organic base such as dimethylaniline or an inorganic base such as sodium hydrogencarbonate, sodium carbonate, potassium hydrogencarbonate or potassium carbonate is preferred. It is particularly preferred to use an inorganic base. When such an inorganic base is employed, the inorganic base can be used as an aqueous solution without any problems.

After the completion of the reaction, the phenol compound (3) of the present invention can be isolated by collecting the reaction product in a manner known per se in the art and then purifying it in accordance with a conventional procedure, for example, recrystallization or column chromatography.

Among the compounds (1) of the present invention, those of the formula (1) in which $-Z_1-$ is represented, for example, by the formula (viii) can be prepared in a manner known per se in the art, for example, in accordance with the process disclosed in Chemical and Pharmaceutical Bulletin, 26, 2508 (1978).

Among the compounds (1) of the present invention, those of the formula (1) in which $-Z_1-$ is represented, for example, by the formula (ix) can be prepared in a manner known per se in the art, for example, in accordance with the process disclosed in Synthesis, 277 (1979).

Among the compounds (2) of the present invention, those of the formula (2) in which —$Z_2$— is represented, for example, by the formula (iii) can be prepared in a manner known per se in the art, for example, in accordance with the process disclosed in Collection of Czechoslovak Chemical Communication, 42, 1651 (1977) or U.S. Pat. No. 3,632,631.

Among the compounds (2) of the present invention, those of the formula (2) in which —$Z_2$— is represented, for example, by the formula (iv) or (v) can be prepared in a manner known per se in the art, for example, in accordance with the process disclosed in U.S. Pat. No. 3,371,109.

Among the compounds (2) of the present invention, those of the formula (2) in which —$Z_2$— is represented, for example, by the formula (viii) can be prepared in a manner known per se in the art, for example, in accordance with the process disclosed in U.S. Pat. No. 3,632,631.

Among the compounds (2) of the present invention, those of the formula (2) in which —$Z_2$— is represented, for example, by the formula (ix) can be prepared in a manner known per se in the art, for example, in accordance with the process disclosed in Journal of Agricultural and Food Chemistry, 13, 537 (1965), 14, 555 (1966), 16, 561 (1968) or 19, 432,441 (1971).

The heat-sensitive recording material according to the present invention features the inclusion of at least one compound represented by the formula (1) or (2) in a heat-sensitive recording material which contains an electron-donating chromogenic compound and an electron-attracting compound. Describing in more detail the constitution of the heat-sensitive recording material of this invention, it is a heat-sensitive recording material which contains an electron-donating chromogenic compound and, as an electron attracting compound, at least one compound represented by the formula (1) or (2), or a heat-sensitive recording material which contains an electron-donating chromogenic compound, an electron-attracting compound and at least one compound represented by the formula (1) or (2).

As will be described later, these heat-sensitive recording materials additionally contain various known additives which have been used to produce conventional heat-sensitive materials, for example, a thermofusible compound.

Each compound represented by the formula (1) or (2), which pertains to the present invention, features the inclusion of a phenolic hydroxyl group and a carbamate group in its molecule. The present invention relates to a heat-sensitive recording material containing an electron-donating chromogenic compound and an electron-attracting compound, in which one or more of the compounds represented by the formula (1) or (2) are contained as the electron-attracting compound. The heat-sensitive recording material of this invention has very strong color-producing ability and provides a color image with excellent storage stability (hydrothermoresistance, waterproofness, etc.). Among the compounds represented by the formula (1) or (2) and useful in the heat-sensitive recording material according to this invention, those having a melting point not lower than about 60° C. are preferred. By using as an electron-attracting compound a compound—whose melting point is about 60° C. to 150° C., preferably about 80° C. to 130° C.—out of the compounds represented by the formula (1) or (2), it is possible to provide a heat-sensitive recording material which is not only excellent in the storage stability of a color image to be produced but also good in color-producing sensitivity.

Further, a compound which is represented by the formula (1) or (2) and has a melting point of 150° C. or higher can also provide a heat-sensitive recording material not only excellent in the storage stability of a color image to be produced but also good in color-producing sensitivity, provided that another electron-attracting compound and/or a thermofusible compound having a melting point of about 60° C. to 150° C., said thermofusible compound being to be described subsequently, is used in combination.

As a compound containing a phenolic hydroxyl group and a carbamate group in its molecule, 3-ethoxycarbonylaminophenol, 4-phenyloxycarbonylaminophenol or the like can be mentioned. As a result of a study conducted by the present inventors, it has, however, been found that a heat-sensitive recording material using the above compound, which contains only one benzene ring in its molecule, as an electron-attracting compound or a heat-sensitive recording material using, as an electron-attracting compound, the above compound in combination with another known electron-attracting compound is hardly considered to be good in the storage stability of a color image to be produced.

Japanese Patent Publication No. 59796/1990 proposes heat-sensitive recording materials which use, as an electron-attracting compound (color-developing agent), a blocked phenol compound obtained by the reaction of an isocyanate compound and a phenol compound. The blocked phenol compounds disclosed in the above patent publication are, however, compounds which do not contain any hydroxyl group in their molecules. Accordingly, heat-sensitive recording materials containing as electron-attracting compounds these blocked phenol compounds, for example, 4-tert-butylphenyloxycarbonylaminobenzene or 2,4-bis(4'-tert-butylphenyloxycarbonylamino)toluene have very poor color-producing ability and cannot produce any color even when heated at high temperatures, for example, at 150° C. These blocked phenol compounds are therefore not considered to have any practical function as an electron-attracting compound. From the foregoing, it is unique and also surprising that the heat-sensitive recording material according to this invention, which contains as an electron-attracting compound at least one compound represented by the formula (1) or (2), is excellent in the storage stability of a color image to be produced.

Further, Japanese Patent Laid-Open No. 18084/1990 proposes, as thermofusible compounds (sensitizers) for heat-sensitive recording materials, carbamate compounds having one of several specific structures. The carbamate compounds disclosed in the above patent publication are considerably different from the compounds of the formula (1) or (2), the latter compounds pertaining to the present invention, in that the former compounds do not contain any phenolic hydroxyl group in their molecules. Because of this, heat-sensitive recording materials containing as a sensitizer one of the compounds disclosed in the above patent publication, for example, 1,6-bis(phenyloxycarbonylamino)hexane are very poor in the storage stability (for example, heat resistance, hydrothermoresistance and waterproofness) of a color image to be produced, compared with heat-sensitive recording materials according to the present invention, the latter heat-sensitive recording materials containing an electron-donating chromogenic compound, an electron-attracting compound (for example, bisphenol A) and a compound of the formula (1) or (2). As has been described above, the excellent storage stability of a color image produced on the heat-sensitive recording material according to the present invention cannot be inferred from any conventional compounds or conventional technology and, although the mechanism has not been fully elucidated, is believed to be attributed to certain advantageous effects inherent to the compound of the formula (1) or (2) which pertains to the present invention and contains both a phenolic hydroxyl group and a carbamate group in its molecule.

Specific examples of the compounds according to the present invention, which are represented by the formula (1) or (2), include, but are not limited to, the following compounds.

1. 2-(4'-Hydroxyphenyl)-2-(4'''-methoxycarbonylaminophenyl)propane
2. 2-(4'-Hydroxyphenyl)-2-(4'''-n-propoxycarbonylaminophenyl)propane
3. 2-(4'-Hydroxyphenyl)-2-(4'''-n-butoxycarbonylaminophenyl)propane
4. 2-(4'-Hydroxyphenyl)-2-(4'''-n-decyloxycarbonylaminophenyl)propane
5. 2-(4'-Hydroxyphenyl)-2-(4'''-n-hexadecyloxycarbonylaminophenyl)propane
6. 2-(4'-Hydroxyphenyl)-2-(4'''-cyclohexyloxycarbonylaminophenyl)propane
7. 2-(4'-Hydroxyphenyl)-2-(4'''-cyclohexylmethyloxycarbonylaminophenyl)propane
8. 2-(4'-Hydroxyphenyl)-2-[4'''-(2-tetrahydrofurfuryl)oxycarbonylaminophenyl]propane
9. 2-(4'-Hydroxyphenyl)-2-[4'''-(2-methoxyethyl)oxycarbonylaminophenyl]propane
10. 2-(4'-Hydroxyphenyl)-2-[4'''-(2-n-butoxyethyl)oxycarbonylaminophenyl]propane
11. 2-(4'-Hydroxyphenyl)-2-[4'''-(3-ethoxypropyl)oxycarbonylaminophenyl]propane
12. 2-(4'-Hydroxyphenyl)-2-[4'''-(3-n-hexyloxypropyl)oxycarbonylaminophenyl]propane
13. 2-(4'-Hydroxyphenyl)-2-[4'''-(2-methoxyethoxyethyl)oxycarbonylaminophenyl]propane
14. 2-(4'-Hydroxyphenyl)-2-[4'''-(2-phenoxyethyl)oxycarbonylaminophenyl]propane
15. 2-(4'-Hydroxyphenyl)-2-{4'''-[2-(4-chlorophenoxy)ethyl]oxycarbonylaminophenyl}propane
16. 2-(4'-Hydroxyphenyl)-2-[4'''-(3-chloropropyl)oxycarbonylaminophenyl]propane
17. 2-(4'-Hydroxyphenyl)-2-(4'''-allyloxycarbonylaminophenyl)propane
18. 2-(4'-Hydroxyphenyl)-2-(4'''-benzyloxycarbonylaminophenyl)propane
19. 2-(4'-Hydroxyphenyl)-2-[4'''-(4-methylbenzyl)oxycarbonylaminophenyl]propane
20. 2-(4'-Hydroxyphenyl)-2-[4'''-(4-phenoxybenzyl)oxycarbonylaminophenyl]propane
21. 2-(4'-Hydroxyphenyl)-2-[4'''-(4-chlorobenzyl)oxycarbonylaminophenyl]propane
22. 2-(4'-Hydroxyphenyl)-2-[4'''-(3-hydroxybenzyl)oxycarbonylaminophenyl]propane
23. 2-(4'-Hydroxyphenyl)-2-[4'''-(2-phenylethyl)oxycarbonylaminophenyl]propane
24. 2-(4'-Hydroxyphenyl)-2-(4'''-phenyloxycarbonylaminophenyl)propane
25. 2-(4'-Hydroxyphenyl)-2-[4'''-(2-naphthyl)oxycarbonylaminophenyl]propane
26. 2-(4'-Hydroxyphenyl)-2-[4'''-(4-phenylphenyl)oxycarbonylaminophenyl]propane
27. 2-(4'-Hydroxyphenyl)-2-[4'''-(4-methylphenyl)oxycarbonylaminophenyl]propane
28. 2-(4'-Hydroxyphenyl)-2-[4'''-(3-methylphenyl)oxycarbonylaminophenyl]propane
29. 2-(4'-Hydroxyphenyl)-2-[4'''-(4-cyclohexylphenyl)oxycarbonylaminophenyl]propane
30. 2-(4'-Hydroxyphenyl)-2-[4'-(4-cumylphenyl)oxycarbonylaminophenyl]propane
31. 2-(4'-Hydroxyphenyl)-2-[4'''-(4-methoxyphenyl)oxycarbonylaminophenyl]propane
32. 2-(4'-Hydroxyphenyl)-2-[4'''-(4-phenoxyphenyl)oxycarbonylaminophenyl]propane
33. 2-(4'-Hydroxyphenyl)-2-[4'''-(4-chlorophenyl)oxycarbonylaminophenyl]propane
34. 2-(4'-Hydroxyphenyl)-2-[4'''-(2-chlorophenyl)oxycarbonylaminophenyl]propane
35. 2-(4'-Hydroxyphenyl)-2-[4'''-(4-nitrophenyl)oxycarbonylaminophenyl]propane
36. 2-(4'-Hydroxyphenyl)-2-[4'''-(4-acetylphenyl)oxycarbonylaminophenyl]propane
37. 2-(4'-Hydroxyphenyl)-2-[4'''-(4-ethoxycarbonylphenyl)oxycarbonylaminophenyl]propane
38. 2-(4'-Hydroxyphenyl)-2-[4'''-(4-benzyloxyphenyl)oxycarbonylaminophenyl]propane
39. 2-(4'-Hydroxyphenyl)-2-[4'''-(4-phenylcarbonylphenyl)oxycarbonylaminophenyl]propane
40. 2-(4'-Hydroxyphenyl)-2-[4'''-(2-chloro-4-nitrophenyl)oxycarbonylaminophenyl]propane
41. 2-(4'-Hydroxyphenyl)-2-[4'''-(2,4-dimethylphenyl)oxycarbonylaminophenyl]propane
42. 2-(3'-Methyl-4'-hydroxyphenyl)-2-(4'''-ethoxycarbonylaminophenyl)propane
43. 2-(3'-Methyl-4'-hydroxyphenyl)-2-[4'''-(4-methoxybenzyl)oxycarbonylaminophenyl]propane
44. 2-(3'-Ethyl-4'-hydroxyphenyl)-2-[4'''-(4-tert-butylphenyl)oxycarbonylaminophenyl)]propane
45. 2-(3',5'-Dimethyl-4'-hydroxyphenyl)-2-[4'''-(2-methylphenyl)oxycarbonylaminophenyl]propane
46. 2-(3'-Methyl-4'-hydroxyphenyl)-2-(3''-methyl-4'-isobutoxycarbonylaminophenyl)propane
47. 2-(4'-Hydroxyphenyl)-2-[3''-methyl-4'''-(4-allylphenyl)oxycarbonylaminophenyl]propane
48. 2-(4'-Hydroxyphenyl)-2-[3''-chloro-4'''-(3-methoxyphenyl)oxycarbonylaminophenyl]propane
49. 2-(4'-Hydroxyphenyl)-2-[3'',5''-dimethyl-4'''-(4-tert-butylcyclohexyl)oxycarbonylaminophenyl]propane
50. 1-(4'-Hydroxyphenyl)-1-(4'''-phenyloxycarbonylaminophenyl)cyclopentane
51. 1-(4'-Hydroxyphenyl)-1-[4'''-(4-methylcyclohexyl)oxycarbonylaminophenyl]cyclohexane
52. 1-(4'-Hydroxyphenyl)-1-(4'''-isopropoxycarbonylaminophenyl)cycloheptane
53. 1-(4'-Hydroxyphenyl)-1-[4'''-(2-acetylphenyl)oxycarbonylaminophenyl]cyclooctane
54. 1-(4'-Hydroxyphenyl)-1-(4'''-sec-butoxycarbonylaminophenyl)methane
55. 1-(4'-Hydroxyphenyl)-1-[4'''-(1-naphtyl)oxycarbonylaminophenyl]methane
56. 2-(4'-Hydroxyphenyl)-2-(4'''-tert-butoxycarbonylaminophenyl)butane
57. 2-(4'-Hydroxyphenyl)-2-[4'''-(3-furyl)oxycarbonylaminophenyl]isohexane
58. 1-(4'-Hydroxyphenyl)-1-(4'''-n-pentyloxycarbonylaminophenyl)-1-phenylmethane
59. 1-(4'-Hydroxyphenyl)-1-[4'''-(3-thienyl)oxycarbonylaminophenyl]-1-phenylethane
60. 2-(4'-Hydroxyphenyl)-2-(4'''-phenyloxycarbonylaminophenyl)hexafluoropropane 61. 2-(4'-Hydroxyphenyl)-2-(4''-N-phenyloxycarbonyl-N-methylaminophenyl)propane
62. 2-(4'-Hydroxyphenyl)-2-(4''-phenylthiolcarbonylaminophenyl)propane
63. 2-(4'-Hydroxyphenyl)-2-(4''-phenyloxythiocarbonylaminophenyl)propane
64. 2-(4'-Hydroxyphenyl)-2-(4''-ethoxycarbonylamino-1''-naphtyl)propane
65. 2-(3'-Hydroxyphenyl)-2-(4''-methoxycarbonylaminophenyl)propane
66. 2-(3''-Hydroxyphenyl)-2-(4''-n-butoxycarbonylaminophenyl)propane
67. 2-(3'-Hydroxyphenyl)-2-[4''-(2-phenoxyethoxyethyl)oxycarbonylaminophenyl]propane
68. 2-(3'-Hydroxyphenyl)-2-[4''-benzyloxycarbonylaminophenyl) propane
69. 2-(3'-Hydroxyphenyl)-2-[4''-(4-chlorobenzyl)oxycarbonylaminophenyl]propane
70. 2-(3'-Hydroxyphenyl)-2-(4''-phenyloxycarbonylaminophenyl)propane
71. 2-(3'-Hydroxyphenyl)-2-[4''-(1-naphtyl)oxycarbonylaminophenyl]propane
72. 2-(3'-Hydroxyphenyl)-2-[4''-(2-phenylphenyl)oxycarbonylaminophenyl]propane
73. 2-(3'-Hydroxyphenyl)-2-[4''-(2-methylphenyl)oxycarbonylaminophenyl]propane
74. 2-(3'-Hydroxyphenyl)-2-[4''-(2-cyclohexylphenyl)oxycarbonylaminophenyl]propane
75. 2-(3'-Hydroxyphenyl)-2-[4''-(2-ethoxyphenyl)oxycarbonylaminophenyl]propane
76. 2-(3'-Hydroxyphenyl)-2-[4''-(3-phenoxyphenyl)oxycarbonylaminophenyl]propane
77. 2-(3'-Hydroxyphenyl)-2-[4''-(4-chlorophenyl)oxycarbonylaminophenyl]propane
78. 2-(3'-Hydroxyphenyl)-2-[4''-(2-chlorophenyl)oxycarbonylaminophenyl]propane
79. 2-(3'-Hydroxyphenyl)-2,-[4''-(4-bromophenyl)oxycarbonylaminophenyl]propane
80. 2-(3'-Hydroxyphenyl)-2-[4''-(4-benzyloxyphenyl)oxycarbonylaminophenyl]propane
81. 2-(3'-Hydroxyphenyl)-2-[4''-(4-cumylphenyl)oxycarbonylaminophenyl]propane
82. 2-(3'-Hydroxyphenyl)-2-[4''-(2,4-dimethylphenyl)oxycarbonylaminophenyl]propane
83. 2-(3'-Hydroxyphenyl)-2-(3'',5''-dimethyl-4''-phenyloxycarbonylaminophenyl)propane
84. 1-(3'-Hydroxyphenyl)-1-(4''-isopentyloxycarbonylaminophenyl)cyclohexane
85. 1-(3'-Hydroxyphenyl)-1-[4''-(2-acetylphenyl)oxycarbonylaminophenyl]cyclohexane
86. 1-(3'-Hydroxyphenyl)-1-[4''-(4-acetyloxyphenyl)oxycarbonylaminophenyl]methane
87. 2-(3'-Hydroxyphenyl)-2-(4''-phenyloxycarbonylaminophenyl)butane
88. 2-(3'-Hydroxyphenyl)-2-(4''-methoxycarbonylaminophenyl)isohexane
89. 1-(4'-methyl-3'-hydroxyphenyl)-1-(4''-methyl-3''-phenyloxycarbonylaminophenyl)methane
90. 1-(4'-methyl-3'-hydroxyphenyl)-1-[4''-methyl-3''-(4-chlorophenyl)oxycarbonylaminophenyl]methane
91. 2-(4'-Hydroxyphenyl)-2-(3''-n-propoxycarbonylaminophenyl)propane
92. 2-(4'-Hydroxyphenyl)-2-[3''-(4-methylcyclohexyl)oxycarbonylaminophenyl]propane
93. 2-(4'-Hydroxyphenyl)-2-[3''-(2-cyclohexylethyl)oxycarbonylaminophenyl]propane
94. 2-(4'-Hydroxyphenyl)-2-[3''-(2-ethoxyethyl)oxycarbonylaminophenyl]propane
95. 2-(4'-Hydroxyphenyl)-2-[3''-(2-isopropoxyethyl)oxycarbonylaminophenyl]propane
96. 2-(4'-Hydroxyphenyl)-2-(3''-phenyloxycarbonylaminophenyl)propane
97. 2-(4'-Hydroxyphenyl)-2-[3''-(4-ethylphenyl)oxycarbonylaminophenyl]propane
98. 2-(4'-Hydroxyphenyl)-2-[3''-(4-methoxyphenyl)oxycarbonylaminophenyl]propane
99. 2-(4'-Hydroxyphenyl)-2-[3''-(2-fluorophenyl)oxycarbonylaminophenyl]propane
100. 2-(4'-Hydroxyphenyl)-2-[3''-(2-ethylphenyl)oxycarbonylaminophenyl]propane
101. 1-(4'-Hydroxyphenyl)-1-(3''-ethoxycarbonylaminophenyl)cyclohexane
102. 1-(4'-Hydroxyphenyl)-1-(3''-phenyloxycarbonylaminophenyl)cyclohexane
103. 2-(4'-Hydroxyphenyl)-2-[3''-(4-benzylphenyl)oxycarbonylaminophenyl]isohexane
104. 1-(2'-Hydroxyphenyl)-1-(4''-n-propoxycarbonylaminophenyl)methane
105. 1-(2'-Hydroxyphenyl)-1-(4''-cyclohexyloxycarbonylaminophenyl)methane
106. 1-(2'-Hydroxyphenyl)-1-(4''-benzyloxycarbonylaminophenyl)methane
107. 1-(2'-Hydroxyphenyl)-1-[4''-(2-methoxyphenyl)oxycarbonylaminophenyl]methane
108. 1-(4'-Hydroxyphenyl)-1-[2''-(4-methylphenyl)oxycarbonylaminophenyl]methane
109. 2-(4'-Hydroxyphenyl)-2-(4''-ethyl-2''-phenyloxycarbonylaminophenyl)propane
110. 1-(2'-Hydroxy-5'-methylphenyl)-1-(2''-hydroxy-3''-phenyloxycarbonylaminophenyl)methane
111. 1-(2',5'-Dihydroxyphenyl)-1-(3''-phenyloxycarbonylaminophenyl)methane
112. 1-(2',5'-Dihydroxyphenyl)-1-(4''-methyl-3''-methoxycarbonylaminophenyl)methane
113. 1-(2',5'-Dihydroxyphenyl)-1-(4''-methyl-3''-phenyloxycarbonylaminophenyl)methane
114. 1-(2'-Hydroxy-5'-n-butylphenyl)-1-(2''-benzyloxycarbonylaminophenyl)methane
115. 1-(2'-Hydroxy-5'-n-pentylphenyl)-1-(2''-phenyloxycarbonylaminophenyl)methane
116. 1-(2'-Hydroxy-5'-cumylphenyl)-1-(2''-methoxycarbonylaminophenyl)methane
117. 4-Hydroxyphenyl-4'-methoxycarbonylaminophenyl ether
118. 4-Hydroxyphenyl-4'-ethoxycarbonylaminophenyl ether
119. 4-Hydroxyphenyl-4'-n-butoxycarbonylaminophenyl ether
120. 4-Hydroxyphenyl-4'-n-hexyloxycarbonylaminophenyl ether
121. 4-Hydroxyphenyl-4'-n-hexadecyloxycarbonylaminophenyl ether
122. 4-Hydroxyphenyl-4'-(2-methoxyethyl)oxycarbonylaminophenyl ether
123. 4-Hydroxyphenyl-4'-(3-methoxypropyl)oxycarbonylaminophenyl ether
124. 4-Hydroxyphenyl-4'-(2-allyloxyethyl)oxycarbonylaminophenyl ether
125. 4-Hydroxyphenyl-4'-benzyloxycarbonylaminophenyl ether
126. 4-Hydroxyphenyl-4'-phenyloxycarbonylaminophenyl ether
127. 4-Hydroxyphenyl-4'-(3-ethylphenyl)oxycarbonylaminophenyl ether
128. 4-Hydroxyphenyl-4'-(4-phenylphenyl)oxycarbonylaminophenyl ether 129. 4-Hydroxyphenyl-4'-(3-phenylphenyl)oxycarbonylaminophenyl ether
130. 4-Hydroxyphenyl-4'-(4-cyclopentylphenyl)oxycarbonylaminophenyl ether
131. 4-Hydroxyphenyl-4'-(3-chlorophenyl)oxycarbonylaminophenyl ether
132. 4-Hydroxyphenyl-4'-(2-benzyloxyphenyl)oxycarbonylaminophenyl ether
133. 4-Hydroxyphenyl-4'-(2,6-dimethylphenyl)oxycarbonylaminophenyl ether
134. 4-Hydroxyphenyl-4'-phenylthiolcarbonylaminophenyl ether
135. 4-Hydroxy-1-naphthyl-4'-ethoxycarbonylaminophenyl ether
136. 3-Hydroxyphenyl-4'-methoxycarbonylaminophenyl ether
137. 3-Hydroxyphenyl-4'-ethoxycarbonylaminophenyl ether
138. 3-Hydroxyphenyl-4'-n-octyloxycarbonylaminophenyl ether
139. 3-Hydroxyphenyl-4'-(3-chlorobenzyl)oxycarbonylaminophenyl ether
140. 3-Hydroxyphenyl-4'-phenyloxycarbonylaminophenyl ether
141. 3-Hydroxyphenyl-4'-(4-isopropylphenyl)oxycarbonylaminophenyl ether
142. 3-Hydroxyphenyl-4'-(4-allylcarbonylphenyl)oxycarbonylaminophenyl ether
143. 3-Hydroxyphenyl-4'-(4-methylthiophenyl)oxycarbonylaminophenyl ether
144. 3-Hydroxyphenyl-4'-(4-methoxyphenyl)oxycarbonylaminophenyl ether
145. 3-Hydroxyphenyl-440 -(3-chlorophenyl)oxycarbonylaminophenyl ether
146. 3-Hydroxyphenyl-3'-methyl-4'-phenyloxycarbonylaminophenyl ether
147. 4-Hydroxyphenyl-3'-n-butoxycarbonylaminophenyl ether
148. 4-Hydroxyphenyl-3'-cyclohexyloxycarbonylaminophenyl ether
149. 4-Hydroxyphenyl-3'-(3-n-butoxypropyl)oxycarbonylaminophenyl ether
150. 4-Hydroxyphenyl-3'-(3-methylbenzyl)oxycarbonylaminophenyl ether
151. 4-Hydroxyphenyl-3'-phenyloxycarbonylaminophenyl ether
152. 4-Hydroxyphenyl-3'-(4-methylphenyl)oxycarbonylaminophenyl ether
153. 4-Hydroxyphenyl-3'-(4-phenoxyphenyl)oxycarbonylaminophenyl ether
154. 4-Hydroxyphenyl-3'-(3-nitrophenyl)oxycarbonylaminophenyl ether
155. 3-Methyl-4-Hydroxyphenyl-3'-phenyloxycarbonylaminophenyl ether
156. 3-Isopropyl-4-Hydroxyphenyl-3'-phenyloxycarbonylaminophenyl ether
157. 4-Hydroxyphenyl-4'-ethoxycarbonylaminophenyl sulfide
158. 4-Hydroxyphenyl-4'-isobutoxycarbonylaminophenyl sulfide
159. 4-Hydroxyphenyl-4'-n-hexadecyloxycarbonylaminophenyl sulfide
160. 4-Hydroxyphenyl-4'-cyclohexyloxycarbonylaminophenyl sulfide
161. 4-Hydroxyphenyl-4'-(2-methoxyethyl)oxycarbonylaminophenyl sulfide
162. 4-Hydroxyphenyl-4'-(2-benzyloxyethyl)oxycarbonylaminophenyl sulfide
163. 4-Hydroxyphenyl-4'-allyloxycarbonylaminophenyl sulfide
164. 4-Hydroxyphenyl-4'-(2-methylbenzyl)oxycarbonylaminophenyl sulfide
165. 4-Hydroxyphenyl-4'-phenyloxycarbonylaminophenyl sulfide
166. 4-Hydroxyphenyl-4'-(2-naphthyl)oxycarbonylaminophenyl sulfide
167. 4-Hydroxyphenyl-4'-(4-phenylphenyl)oxycarbonylaminophenyl sulfide
168. 4-Hydroxyphenyl-4'-(4-methylphenyl)oxycarbonylaminophenyl sulfide
169. 4-Hydroxyphenyl-4'-(4-chlorophenyl)oxycarbonylaminophenyl sulfide
170. 4-Hydroxyphenyl-4'-(4-methoxycarbonylphenyl)oxycarbonylaminophenyl sulfide
171. 4-Hydroxyphenyl-4'-(4-cumylphenyl)oxycarbonylaminophenyl sulfide
172. 4-Hydroxyphenyl-4'-phenylthiolcarbonylaminophenyl sulfide
173. 3-Hydroxyphenyl-4'-methoxycarbonylaminophenyl sulfide
174. 3-Hydroxyphenyl-4'-(2-chloroethyl)oxycarbonylaminophenyl sulfide
175. 3-Hydroxyphenyl-4'-benzyloxycarbonylaminophenyl sulfide
176. 3-Hydroxyphenyl-4'-phenyloxycarbonylaminophenyl sulfide
177. 3-Hydroxyphenyl-4'-(4-n-butylphenyl)oxycarbonylaminophenyl sulfide
178. 3-Hydroxyphenyl-4'-(4-formylphenyl)oxycarbonylaminophenyl sulfide
179. 3-Hydroxyphenyl-4'-(2,5-dimethylphenyl)oxycarbonylaminophenyl sulfide
180. 3-Hydroxyphenyl-3'-methyl-4'-phenyloxycarbonylaminophenyl sulfide
181. 4-Hydroxyphenyl-3'-n-hexyloxycarbonylaminophenyl sulfide
182. 4-Hydroxyphenyl-3'-cyclohexyloxycarbonylaminophenyl sulfide
183. 4-Hydroxyphenyl-3'-(2-n-hexyloxyethyl)oxycarbonylaminophenyl sulfide
184. 4-Hydroxyphenyl-3'-(4-allylbenzyl)oxycarbonylaminophenyl sulfide
185. 4-Hydroxyphenyl-3'-phenyloxycarbonylaminophenyl sulfide
186. 4-Hydroxyphenyl-3'-(4-allyloxyphenyl)oxycarbonylaminophenyl sulfide
187. 4-Hydroxyphenyl-3'-(4-hydroxyphenyl)oxycarbonylaminophenyl sulfide
188. 4-Hydroxyphenyl-3'-(3,4-dimethylphenyl)oxycarbonylaminophenyl sulfide
189. 3-Methyl-4-Hydroxyphenyl-3'-phenyloxycarbonylaminophenyl sulfide
190. 3-Isopropyl-4-Hydroxyphenyl-3'-phenyloxycarbonylaminophenyl sulfide
191. 4"-Methoxycarbonylaminophenyl-4-(4,-hydroxy)phenylbenzoate
192. 4"-Phenyloxycarbonylaminophenyl-4-(4'-hydroxy)phenylbenzoate
193. 3"-Phenyloxycarbonylaminophenyl-4-(4'-hydroxy)phenylbenzoate
194. 4'-Hydroxyphenyl-4-ethoxycarbonylaminobenzoate
195. 4'-Hydroxyphenyl-4-phenyloxycarbonylaminobenzoate
196. 4-Hydroxy-4'-n-octyloxycarbonylaminobiphenyl 197. 4-Hydroxy-4'-(2,6-dimethylcyclohexyl)oxycarbonylaminobiphenyl
198. 4-Hydroxy-4'-(2-ethoxyethoxyethyl)oxycarbonylaminobiphenyl
199. 4-Hydroxy-4'-(2-benzyloxyethyl)oxycarbonylaminobiphenyl
200. 4-Hydroxy-4'-benzyloxycarbonylaminobiphenyl
201. 4-Hydroxy-4'-phenyloxycarbonylaminobiphenyl
202. 4-Hydroxy-4'-(2-naphthyl)oxycarbonylaminobiphenyl
203. 4-Hydroxy-4'-(4-phenylphenyl)oxycarbonylaminobiphenyl
204. 4-Hydroxy-4'-(4-tert-octylphenyl)oxycarbonylaminobiphenyl
205. 4-Hydroxy-4'-(4-isopropoxyphenyl)oxycarbonylaminobiphenyl
206. 4-Hydroxy-4'-(4-chlorophenyl)oxycarbonylaminobiphenyl
207. 4-Hydroxy-4'-(4-cyanophenyl)oxycarbonylaminobiphenyl
208. 4-Hydroxy-2'-phenyl-4'-methoxycarbonylaminobiphenyl
209. 4-Hydroxy-3,5-diphenyl-4'-phenyloxycarbonylaminobiphenyl
210. 3-Hydroxy-4'-methoxycarbonylaminobiphenyl
211. 3-Hydroxy-4'-(2-chlorobenzyl)oxycarbonylaminobiphenyl
212. 3-Hydroxy-4'-phenyloxycarbonylaminobiphenyl
213. 3-Hydroxy-4'-(4-n-propylphenyl)oxycarbonylaminobiphenyl
214. 3-Hydroxy-4'-(2-chlorophenyl)oxycarbonylaminobiphenyl
215. 3-Hydroxy-3'-methyl-4'-phenyloxycarbonylaminobiphenyl
216. 3-Hydroxy-5'-phenyl-4'-methoxycarbonylaminobiphenyl
217. 4-Hydroxy-3'-n-nonyloxycarbonylaminobiphenyl
218. 4-Hydroxy-3'-cyclohexyloxycarbonylaminobiphenyl
219. 4-Hydroxy-3'-phenyloxycarbonylaminobiphenyl
220. 4-Hydroxy-3'-(4-fluorophenyl)oxycarbonylaminobiphenyl
221. 2-Hydroxy-2'-methoxycarbonylaminobiphenyl
222. 1-Hydroxy-4-methoxycarbonylaminonaphthalene
223. 1-Hydroxy-4-(2-ethylhexyl)oxycarbonylaminonaphthalene
224. 1-Hydroxy-4-benzyloxycarbonylaminonaphthalene
225. 1-Hydroxy-4-(4'-methylphenyl)oxycarbonylaminonaphthalene
226. 1-Hydroxy-4-(4'-phenylphenyl)oxycarbonylaminonaphthalene
227. 1-Hydroxy-5-methoxycarbonylaminonaphthalene
228. 1-Hydroxy-5-cyclohexyloxycarbonylaminonaphthalene
229. 1-Hydroxy-5-(4'-acetyloxyphenyl)oxycarbonylaminonaphthalene
230. 2-Hydroxy-7-methoxycarbonylaminonaphthalene
231. 2-Hydroxy-7-phenyloxycarbonylaminonaphthalene
232. 2-Hydroxy-7-(4'-methoxycarbonylphenyl)oxycarbonylaminonaphthalene
233. 2-Hydroxy-6-(4'-isopropoxyphenyl)oxycarbonylaminonaphthalene
234. 2-Hydroxy-8-phenyloxycarbonylaminonaphthalene
235. 2-Hydroxy-8-(4'-cumylphenyl)oxycarbonylaminonaphthalene
236. 1-(4'-hydroxyphenyl)-4-(4''-methoxycarbonylaminophenyl)benzene
237. 1-(4'-hydroxyphenyl)-4-(4''-phenyloxycarbonylaminophenyl)benzene
238. 4-Hydroxy-4'-n-butoxycarbonylaminobenzophenone
239. 4-Hydroxy-4'-(2-naphthyl)oxycarbonylaminobenzophenone
240. 3-Hydroxy-2'-cyclohexyloxycarbonylaminobenzophenone
241. 2-Hydroxy-3'-(4-methylphenyl)oxycarbonylaminobenzophenone
242. 2-Hydroxy-5-methyl-3'-(4-tert-butylphenyl)oxycarbonylaminobenzophenone
243. 3-Hydroxy-2'-(4-cyclohexylphenyl)oxycarbonylamino-5'-chlorobenzophenone
244. 4-Hydroxy-3,5-di-tert-butyl-4'-(4-cumylphenyl)oxycarbonylaminobenzophenone
245. 1-(4'-Hydroxyphenyl)-2-(4''-allyloxycarbonylaminophenyl)ethane
246. 1-(4'-Hydroxyphenyl)-2-[4''-(4-phenylphenyl)oxycarbonylphenyl]ethane
247. 1-(2',5'-Dihydroxyphenyl)-2-[3''-methoxy-4''-(4-methoxyphenyl)oxycarbonylaminophenyl]ethane
248. 1-(3'-Hydroxyphenyl)-3-[3''-(2-methoxyethyl)oxycarbonylaminophenyl]propane
249. 1-(3'-Hydroxyphenyl)-3-[4''-(3-methoxymethylphenyl)oxycarbonylaminophenyl]propane
250. 1-(4'-Hydroxyphenyl)-2-[4''-(2-n-butoxyethyl)oxycarbonylaminophenyl]ethene
251. 1-(4'-Hydroxyphenyl)-2-[4''-(4-allyloxyphenyl)oxycarbonylaminophenyl]ethene
252. 3-(4'-Hydroxyphenyl)-4-[4''-(2-methoxyethoxyethyl)oxycarbonylaminophenyl]-3-hexene
253. 3-(4'-Hydroxyphenyl)-4-[4''-(4-benzyloxyphenyl)oxycarbonylaminophenyl]-3-hexene
254. 3-(4'-Hydroxyphenyl)-4-[3''-(2-benzyloxyphenyl)oxycarbonylamino-4''-hydroxyphenyl]-3-hexene
255. 1-(4''-Hydroxyphenyl)-4-[4''-(2-allyloxyethyl)oxycarbonylaminophenyl]oxybenzene
256. 1-(4'-Hydroxyphenyl)-4-[4''-(4-octyloxyphenyl)oxycarbonylaminophenyl]oxybenzene
257. 4'-(2-Benzyloxyethyl)oxycarbonylaminophenyl 2-hydroxybenzoate
258. 4'-(4-Phenoxyphenyl)oxycarbonylaminophenyl 2-hydroxybenzoate
259. 3'-(2-Benzyloxyethoxyethyl)oxycarbonylamino-4'-chlorophenyl 4-hydroxy-3,5-di-tert-butylbenzoate
260. 3'-(4-Acetylphenyl)oxycarbonylamino-4'-chlorophenyl 4-hydroxy-3,5-di-tert-butylbenzoate
261. 1-(4'-Hydroxyphenyl)-2-[2''-hydroxy-4''-(2-phenoxyethyl)oxycarbonylaminophenylcarbonyl]ethane
262. 1-(4'-Hydroxyphenyl)-2-[2''-hydroxy-4''-(4-benzylcarbonylphenyl)oxycarbonylaminophenylcarbonyl]ethane
263. 1-(4'-Hydroxyphenyl)-2-[2''-hydroxy-4''-(2-tetrahydrofurfuryl)oxycarbonylaminophenylcarbonyl]ethane
264. 1-(4'-Hydroxyphenyl)-2-[2''-hydroxy-4''-(4-methoxycarbonylphenyl)oxycarbonylaminophenylcarbonyl]ethene
265. 1-(4'-Hydroxyphenyl)-2-[4''-(2-chloroethyl)oxycarbonylaminophenyl]ethene
266. 1-(4'-Hydroxyphenyl)-2-[4''-(4-acetyloxycarbonylphenyl)oxycarbonylaminophenyl]ethene
267. 1-(2',4',6'-Trihydroxyphenylcarbonyl)-1-(4''-benzyloxycarbonylaminophenyl)methane 268. 1-(2',4',6'-Trihydroxyphenylcarbonyl)-1-[4"-(4-phenylcarbonyl)oxycarbonylaminophenyl]methane
269. 3-(4'-Hydroxyphenyl)-4-[4"-(4-chlorobenzyl)oxycarbonylaminophenyl]hexane
270. 3-(4'-Hydroxyphenyl)-4-[4"-(4-methylthiophenyl)oxycarbonylaminophenyl]hexane
271. 1-(4'-Hydroxyphenyloxy)-2-[4"-(4-allylbenzyl)oxycarbonylaminophenyloxy]ethane
272. 1-(4'-Hydroxyphenyloxy)-4-[4"-(4"-chlorophenyl)oxycarbonylaminophenyloxy]butane
273. 1-(4'-Hydroxyphenyloxy)-5-[4"-(3-hydroxybenzyl)oxycarbonylaminophenyloxy]pentane
274. 1-(4'-Hydroxyphenyloxy)-6-[4"-(4-nitrophenyl)oxycarbonylaminophenyloxy]hexane
275. 1-(4'-Hydroxyphenylcarbonyl)-1-[4"-(4-hydroxy-3methoxybenzyl)oxycarbonylaminophenylcarbonyl]methane
276. 1-(4'-Hydroxyphenylcarbonyl)-1-[4"-(2,4-dimethylphenyl)oxycarbonylaminophenylcarbonyl]methane
277. 1-(3'-Methoxy-4'-hydroxyphenylcarbonyl)-1-[4"-(4-chlorobenzyl)oxycarbonylaminophenylcarbonyl]methane
278. 1-(3'-Methoxy-4'-hydroxyphenylcarbonyl)-1-[4"-(2,4,6-trichlorophenyl)oxycarbonylaminophenylcarbonyl]methane
279. 1-(4'-Hydroxyphenylcarbonyl)-1-[3"-(2-furfuryl)oxycarbonylaminophenylcarbonyloxy]methane
280. 1-(4'-Hydroxyphenylcarbonyl)-1-[3"-(2,4,6-trimethoxyphenyl)oxycarbonylaminophenylcarbonyloxy]methane
281. 2-(4'-Hydroxyphenyl)-2-(4"-methylaminocarbonyloxyphenyl]propane
282. 2-(4'-Hydroxyphenyl)-2-(4"-n-octylaminocarbonyloxyphenyl)propane
283. 2-(4'-Hydroxyphenyl)-2-(4"-cyclohexylaminocarbonyloxyphenyl)propane
284. 2-(4'-Hydroxyphenyl)-2-[4"-(2-tetrahydrofurfuryl)aminocarbonyloxyphenyl]propane
285. 2-(4'-Hydroxyphenyl)-2-[4"-(2-methoxyethyl)aminocarbonyloxyphenyl]propane
286. 2-(4'-Hydroxyphenyl)-2-[4"-(2-methoxyethoxyethyl)aminocarbonyloxyphenyl]propane
287. 2-(4'-Hydroxyphenyl)-2-[4"-(3-chloropropyl)aminocarbonyloxyphenyl]propane
288. 2-(4'-Hydroxyphenyl)-2-(4"-allylaminocarbonyloxyphenyl)propane
289. 2-(4'-Hydroxyphenyl)-2-[4"-(4-methylbenzyl)aminocarbonyloxyphenyl]propane
290. 2-(4'-Hydroxyphenyl)-2-(4"-phenylaminocarbonyloxyphenyl) propane
291. 2-(4'-Hydroxyphenyl)-2-[4"-(1-naphthyl)aminocarbonyloxyphenyl]propane
292. 2-(4'-Hydroxyphenyl)-2-[4"-(4-phenylphenyl)aminocarbonyloxyphenyl ]propane
293. 2-(4'-Hydroxyphenyl)-2-[4"-(4-methylphenyl)aminocarbonyloxyphenyl]propane
294. 2-(4'-Hydroxyphenyl)-2-[4"-(4-methoxyphenyl)aminocarbonyloxyphenyl]propane
295. 2-(4'-Hydroxyphenyl)-2-[4"-(4-chlorophenyl)aminocarbonyloxyphenyl]propane
296. 2-(4'-Hydroxyphenyl)-2-[4"-(4-acetylphenyl)aminocarbonyloxyphenyl]propane
297. 2-(4'-Hydroxyphenyl)-2-[4"-(4-ethoxycarbonylphenyl)aminocarbonyloxyphenyl]propane
298. 2-(4'-Hydroxyphenyl)-2-[4"-(4-phenylcarbonylphenyl)aminocarbonyloxyphenyl] propane
299. 2-(4'-Hydroxyphenyl)-2-[4"-(2-chloro-6-methylphenyl)aminocarbonyloxyphenyl]propane
300. 2-(4'-Hydroxyphenyl)-2-[4"-(2,4-dimethylphenyl)aminocarbonyloxyphenyl]propane
301. 2-(3'-Methyl-4'-hydroxyphenyl)-2-(3"-methyl-4"-ethylaminocarbonyloxyphenyl)propane
302. 2-(3'-Methyl-4'-hydroxyphenyl)-2-(3"-methyl-4"-phenylaminocarbonyloxyphenyl)propane
303. 2-(3',5'-Di-tert-butyl-4'-hydroxyphenyl)-2-(3",5"-di-tert-butyl-4"-n-butylaminocarbonyloxyphenyl)propane
304. 2-(3'-chloro-4'-hydroxyphenyl)-2-(3"-chloro-4"-phenylaminocarbonyloxyphenyl)propane
305. 1-(4'-Hydroxyphenyl)-1-(4"-phenylaminocarbonyloxyphenyl)cyclopentane
306. 1-(4'-Hydroxyphenyl)-1-(4"-methylaminocarbonyloxyphenyl)cyclohexane
307. 1-(4'-Hydroxyphenyl)-1-(4"-phenylaminocarbonyloxyphenyl)cyclohexane
308. 1-(4'-Hydroxyphenyl)-1-(4"-n-propylaminocarbonyloxyphenyl)cycloheptane
309. 1-(4'-Hydroxyphenyl)-1-(4"-phenylaminocarbonyloxyphenyl)cyclooctane
310. 1-(4'-Hydroxyphenyl)-1-(4"-methylaminocarbonyloxyphenyl)methane
311. 1-(4'-Hydroxyphenyl)-1-(4"-benzylaminocarbonyloxyphenyl)methane
312. 1-(4'-Hydroxyphenyl)-1-(4"-phenylaminocarbonyloxyphenyl)methane
313. 2-(4'-Hydroxyphenyl)-2-(4"-methylaminocarbonyloxyphenyl)butane
314. 2-(4'-Hydroxyphenyl)-2-(4"-phenylaminocarbonyloxyphenyl)isohexane
315. 1-(4'-Hydroxyphenyl)-1-(4"-phenylaminocarbonyloxyphenyl)-1-phenylethane
316. 1-(3'-Methyl-4'-hydroxyphenyl)-1-(3"-methyl-4"-phenylaminocarbonyloxyphenyl)methane
317. 1-(3'-Methyl-4'-hydroxyphenyl)-1-(3"-methyl-4"-(4-chlorophenyl)aminocarbonyloxyphenyl)methane
318. 2-(4'-Hydroxyphenyl)-2-(4"-phenylaminocarbonyloxyphenyl)hexafluoropropane
319. 2-(4'-Hydroxyphenyl)-2-(4"-dimethylaminocarbonyloxyphenyl)propane
320. 2-(4'-Hydroxyphenyl)-2-(4"-N-phenyl-N-methylaminocarbonyloxyphenyl)propane
321. 2-(4'-Hydroxyphenyl)-2-(4"-phenylaminothiocarbonyloxyphenyl)propane
322. 2-(3'-Hydroxyphenyl)-2-(4"-methylaminocarbonyloxyphenyl)propane
323. 2-(4'-Hydroxyphenyl)-2-(3"-ethylaminocarbonyloxyphenyl)propane
324. 2-(2'-Hydroxyphenyl)-2-(4"-phenylaminocarbonyloxyphenyl)propane
325. 2-(4'-Hydroxyphenyl)-2-(2"-n-butylaminocarbonyloxyphenyl)propane
326. 1-(4'-Hydroxyphenyl)-1-(2"-phenylaminocarbonyloxyphenyl)methane
327. 1-(2'-Hydroxyphenyl)-1-(4"-n-butylaminocarbonyloxyphenyl)methane
328. 1-(2'-Hydroxyphenyl)-1-[2"-(4-methylphenyl)aminocarbonyloxyphenyl)methane
329. 4-Hydroxyphenyl-4'-methylaminocarbonyloxyphenyl ether
330. 4-Hydroxyphenyl-4'-n-hexylaminocarbonyloxyphenyl ether
331. 4-Hydroxyphenyl-4'-n-hexadecylaminocarbonyloxyphenyl ether 332. 4-Hydroxyphenyl-4'-cyclohexylaminocarbonyloxyphenyl ether
333. 4-Hydroxyphenyl-4'-(2-methoxyethyl)aminocarbonyloxyphenyl ether
334. 4-Hydroxyphenyl-4'-benzylaminocarbonyloxyphenyl ether
335. 4-Hydroxyphenyl-4'-phenylaminocarbonyloxyphenyl ether
336. 4-Hydroxyphenyl-4'-(4-methylphenyl)aminocarbonyloxyphenyl ether
337. 4-Hydroxyphenyl-4'-(3-chlorophenyl)aminocarbonyloxyphenyl ether
338. 4-Hydroxyphenyl-4'-(2,4-dimethylphenyl)aminocarbonyloxyphenyl ether
339. 4-Hydroxyphenyl-4'-phenylaminothiocarbonyloxyphenyl ether
340. 2-Hydroxyphenyl-2'-methylaminocarbonyloxyphenyl ether
341. 2-Hydroxyphenyl-2'-(4-methylbenzyl)aminocarbonyloxyphenyl ether
342. 2-Hydroxyphenyl-2'-phenylaminocarbonyloxyphenyl ether
343. 2-Hydroxyphenyl-2'-(4-methoxyphenyl)aminocarbonyloxyphenyl ether
344. 2-Hydroxyphenyl-2'-(4-chlorophenyl)aminocarbonyloxyphenyl ether
345. 2-Hydroxyphenyl-2'-(3-chlorophenyl)aminocarbonyloxyphenyl ether
346. 4-Hydroxyphenyl-4'-ethylaminocarbonyloxyphenyl sulfide
347. 4-Hydroxyphenyl-4'-n-octylaminocarbonyloxyphenyl sulfide
348. 4-Hydroxyphenyl-4'-cyclohexylaminocarbonyloxyphenyl sulfide
349. 4-Hydroxyphenyl-4'-(2-phenoxyethyl)aminocarbonyloxyphenyl sulfide
350. 4-Hydroxyphenyl-4'-allylaminocarbonyloxyphenyl sulfide
351. 4-Hydroxyphenyl-4'-(4-methylbenzyl)aminocarbonyloxyphenyl sulfide
352. 4-Hydroxyphenyl-4'-phenylaminocarbonyloxyphenyl sulfide
353. 4-Hydroxyphenyl-4'-(2-chlorophenyl)aminocarbonyloxyphenyl sulfide
354. 4-Hydroxyphenyl-4'-(4-acetyloxyphenyl)aminocarbonyloxyphenyl sulfide
355. 4-Hydroxyphenyl-4'-(4-chloro-3-methylphenyl)aminocarbonyloxyphenyl sulfide
356. 4-Hydroxyphenyl-4'-(2,4-dimethylphenyl)aminocarbonyloxyphenyl sulfide
357. 3-Methyl-4-Hydroxyphenyl-3'-methyl-4'-phenylaminocarbonyloxyphenyl sulfide
358. 3,5-Dichloro-4-Hydroxyphenyl-3',5'-dichloro-4'-phenylaminocarbonyloxyphenyl sulfide
359. 4-Hydroxyphenyl-4'-phenylaminothiocarbonyloxyphenyl sulfide
360. 2-Hydroxyphenyl-2'-methylaminocarbonyloxyphenyl sulfide
361. 2-Hydroxyphenyl-2'-phenylaminocarbonyloxyphenyl sulfide
362. 2-Hydroxy-3,5-dichlorophenyl-2'-phenylaminocarbonyloxy-3',5'-dichlorophenyl sulfide
363. 4-Hydroxyphenyl-4'-phenylaminocarbonyloxyphenyl sulfoxide
364. 4-Hydroxyphenyl-4'-phenylaminocarbonyloxyphenyl sulfone
365. 4''-Methylaminocarbonyloxyphenyl 4-(4'-hydroxy)phenylbenzoate
366. 4'''-Phenylaminocarbonyloxyphenyl 4-(4'-hydroxy)phenylbenzoate
367. 4-Hydroxyphenyl 4-n-butylaminocarbonyloxybenzoate
368. 4-Hydroxyphenyl 4-phenylaminocarbonyloxybenzoate
369. 4-Hydroxy-4'-ethylaminocarbonyloxybiphenyl
370. 4-Hydroxy-4'-cyclohexylaminocarbonyloxybiphenyl
371. 4-Hydroxy-4'-(2-methoxyethyl)aminocarbonyloxybiphenyl
372. 4-Hydroxy-4'-benzylaminocarbonyloxybiphenyl
373. 4-Hydroxy-4'-phenylaminocarbonyloxybiphenyl
374. 4-Hydroxy-4'-(4-methoxyphenyl)aminocarbonyloxybiphenyl
375. 3,5-Di-tert-butyl-4-hydroxy-3',5'-di-tert-butyl-4'-phenylaminocarbonyloxybiphenyl
376. 2-Hydroxy-2'-n-propylaminocarbonyloxybiphenyl
377. 2-Hydroxy-2'-phenylaminocarbonyloxybiphenyl
378. 1-Hydroxy-4-methylaminocarbonyloxynaphthalene
379. 1-Hydroxy-4-phenylaminocarbonyloxynaphthalene
380. 1-Hydroxy-4-methylaminothiocarbonyloxynaphthalene
381. 1-Hydroxy-5-methylaminocarbonyloxynaphthalene
382. 2-Hydroxy-1-methylaminocarbonyloxynaphthalene
383. 2-Hydroxy-5-ethylaminocarbonyloxynaphthalene
384. 2-Hydroxy-8-methylaminocarbonyloxynaphthalene
385. 2-Hydroxy-8-phenylaminocarbonyloxynaphthalene
386. 1,8-Dihydroxy-4-n-butylaminocarbonyloxynaphthalene
387. 1,8-Dihydroxy-4-methylaminothiocarbonyloxynaphthalene Examples of the colorless or slightly-colored electron-donating chromogenic compounds usable in the present invention include triarylmethane compounds, diarylmethane compounds, Rhodamine-lactam compounds, fluoran compounds, indolylphthalide compounds, pyridine compounds, spiro compounds and fluorene compounds.

Specific examples of the triarylmethane compounds include 3,3-bis(4-dimethylaminophenyl)-6-dimethylaminophthalide [also called "crystal violet lactone"], 3,3-bis(4-dimethylaminophenyl)phthalide, 3-(4-dimethylaminophenyl)-3-(1,3-dimethylindol-3-yl)phthalide, 3-(4-dimethylaminophenyl)-3-(2-methylindol-3-yl)phthalide, 3,3-bis(9-ethylcarbazol-3-yl)-6-dimethylaminophthalide, 3-(4-dimethylaminophenyl)-3-(1-methylpyrrol-3-yl)-6-dimethylaminophthalide and 3,3-bis[2,2-bis(4-dimethylaminophenyl)ethenyl]-4,5,6,7-tetrachlorophthalide.

Specific examples of the diarylmethane compounds include 4,4-bis-dimethylaminobenzhydrinbenzyl ether, N-halophenyl-leucoauramines and N-2,4,5-trichlorophenylleucoauramine.

Specific examples of the Rhodamine-lactam compounds include Rhodamine-B-anilinolactam, Rhodamine-(4-nitroanilino)lactam and Rhodamine-B-(4-chloroanilino)lactam.

Specific examples of the fluoran compounds include 3,6-dimethoxyfluoran, 3-dimethylamino-7-methoxyfluoran, 3-diethylamino-6-methoxyfluoran, 3-diethylamino-7-methoxyfluoran, 3-diethylamino-7-chlorofluoran, 3-diethylamino-6-methyl-7-chlorofluoran, 3-diethylamino-6,7-dimethylfluoran, 3-N-cyclohexyl-N-n-butylamino-7-methylfluoran, 3-diethylamino-7-dibenzylaminofluoran, 3-diethylamino-7-n-octylaminofluoran, 3-diethylamino-7-di-n-hexylaminofluoran, 3-diethylamino-7-anilinofluoran, 3-diethylamino-7-(2-chloroanilino)fluoran, 3-diethylamino-7-(3-chloroanilino) fluoran, 3-diethylamino-7-(2,3-dichloroanilino)fluoran, 3-diethylamino- 7-(3-trifluoromethylanilino)fluoran, 3-di-n-butylamino-7-(2-chloroanilino)fluoran, 3-diethylamino-6-chloro-7-anilinofluoran, 3-di-n-butylamino-6-chloro-7-anilinofluoran, 3-diethylamino-6-methoxy-7-anilinofluoran, 3-di-n-butylamino-6-ethoxy-7-anilinofluoran, 3-pyrrolidino-6-methyl-7-anilinofluoran, 3-morpholino-6-methyl-7-anilinofluoran, 3-dimethylamino-6-methyl-7-anilinofluoran, 3-diethylamino-6-methyl-7-anilinofluoran, 3-di-n-butylamino-6-methyl-7-anilinofluoran, 3-di-n-pentylamino-6-methyl-7-anilinofluoran, 3-di-n-octylamino-6-methyl-7-anilinofluoran, 3-N-ethyl-N-methylamino-6-methyl-7-anilinofluoran, 3-N-n-propyl-N-methylamino-6-methyl-7-anilinofluoran, 3-N-n-propyl-N-ethylamino-6-methyl-7-anilinofluoran, 3-N-isopropyl-N-methylamino-6-methyl-7-anilinofluoran, 3-N-n-butyl-N-methylamino-6-methyl-7-anilinofluoran, 3-N-n-butyl-N-n-ethylamino-6-methyl-7-anilinofluoran, 3-N-n-butyl-N-n-propylamino-6-methyl-7-anilinofluoran, 3-N-isobutyl-N-methylamino-6-methyl-7-anilinofluoran, 3-N-isobutyl-N-ethylamino-6-methyl-7-anilinofluoran, 3-N-isopentyl-N-ethylamino-6-methyl-7-anilinofluoran, 3-N-n-hexyl-N-ethylamino-6-methyl-7-anilinofluoran, 3-N-n-octyl-N-ethylamino-6-methyl-7-anilinofluoran, 3-N-cyclohexyl-N-methylamino-6-methyl-7-anilinofluoran, 3-N-cyclohexyl-N-n-propylamino-6-methyl-7-anilinofluoran, 3-N-cyclohexyl-N-n-butylamino-6-methyl-7-anilinofluoran, 3-N-cyclohexyl-N-n-pentylamino-6-methyl-7-anilinofluoran, 3-N-cyclohexyl-N-n-hexylamino-6-methyl-7-anilinofluoran, 3-N-cyclohexyl-N-n-heptylamino-6-methyl-7-anilinofluoran, 3-N-cyclohexyl-N-n-octylamino-6-methyl-7-anilinofluoran, 3-N-cyclohexyl-N-n-decylamino-6-methyl-7-anilinofluoran, 3-N-2'-methoxyethyl-N-methylamino-6-methyl-7-anilinofluoran, 3-N-2'-methoxyethyl-N-ethylamino-6-methyl-7-anilinofluoran, 3-N-2'-ethoxyethyl-N-methylamino-6-methyl-7-anilinofluoran, 3-N-2'-ethoxyethyl-N-ethylamino-6-methyl-7-anilinofluoran, 3-N-3'-methoxypropyl-N-methylamino-6-methyl-7-anilinofluoran, 3-N-3'-ethoxypropyl-N-methylamino-6-methyl-7-anilinofluoran, 3-N-2'-methoxyethyl-N-isobutylamino-6-Methyl-7-anilinofluoran, 3-N-2'-tetrahydrofurfuryl-N-ethylamino-6-methyl-7-anilinofluoran, 3-N-(4'-methylphenyl)-N-ethylamino-6-methyl-7-anilinofluoran, 3-diethylamino-6-ethyl-7-anilinofluoran, 3-di-ethylamino-6-methyl-7-(2',6'-dimethylphenylamino)fluoran, 3-di-n-butylamino-6-methyl-7-(2',6'-dimethylphenylamino)fluoran, 3-di-n-butylamino-7-(2',6'-dimethylphenylamino)fluoran and 2,2-bis[4'-(3-N-cyclohexyl-N-methylamino-6-methylfluoran)-7-ylaminophenyl]propane.

Specific examples of the indolylphthalide compounds include 3,3-bis(1-ethyl-2-methylindol-3-yl)phthalide, 3,3-bis(1-octyl-2-methylindol-3-yl)phthalide, 3-(2-ethoxy-4-diethylaminophenyl)-3-(1-ethyl-2-methylindol-3-yl)phthalide, 3-(2-ethoxy-4-dibutylaminophenyl)-3-(1-ethyl-2-methylindol-3-yl)phthalide and 3-(2-ethoxy-4-diethylaminophenyl)-3-(1octyl-2-methylindol-3-yl)phthalide.

Specific examples of the pyridine compounds include 3-(2-ethoxy-4-diethylaminophenyl)-3-(1-octyl-2methylindol-3-yl)-4- and -7-azaphthalides, 3-(2-ethoxy-4-diethylaminophenyl)-3-(1-ethyl-2-methylindol-3-yl)-4- and -7-azaphthalides, 3-(2-hexyloxy-4-diethylaminophenyl)-3-(1-ethyl-2-methylindol-3-yl)-4- and -7-azaphthalides, 3-(2-ethoxy-4-diethylaminophenyl)-3-(1-ethyl-2-phenylindol-3-yl)-4- and -7-azaphthalides, and 3-(2-butoxy-4-diethylaminophenyl)-3-(1-ethyl-2-phenylindol-3-yl)-4- and -7-azaphthalides.

Specific examples of the spiro compounds include 3-methyl-spiro-dinaphthopyran, 3-ethyl-spiro-dinaphthopyran, 3-phenyl-spiro-dinaphthopyran, 3-benzyl-spiro-dinaphthopyran, 3-methyl-naphtho-(3-methoxybenzo)spiro-pyran and 3-propyl-spiro-dibenzopyran.

Specific examples of the fluorene compounds include 3',6'-bisdiethylamino-5-diethylaminospiro(isobenzofuran-1,9'-fluoren)-3-on and 3',6'-bisdiethylamino-7-diethylamino-2-methylspiro(1,3-benzooxazine-4,9'-fluorene).

These electron-donating chromogenic compounds can be used either singly or, to adjust the tone of color images to be produced or to obtain a multi-color heat-sensitive recording material or for other purposes, in combination.

In the heat-sensitive recording material according to the present invention, it is generally desirable to use the electron-attracting compound in an amount of 50-700 parts by weight, preferably 100-500 parts by weight per 100 parts by weight of the electron-donating chromogenic compound. As has already been mentioned above, the heat-sensitive recording material according to this invention can also use, as an electron-attracting compound, an electron-attracting compound other than the compound represented by the formula (1) or (2) in combination with the latter compound.

In particular, a heat-sensitive recording material using, as an electron-attracting compound, the compound represented by the formula (1) or (2) in combination with another electron-attracting compound is excellent in the storage stability (hydrothermo-resistance, waterproofness, oil resistance, etc.) of color images to be produced, and is preferred.

In this case, it is generally desirable to control the proportion of the compound represented by the formula (1) or (2) to at least 5 wt. %, preferably 20 wt. % or more, more preferably 30 wt. % or more, all based on the whole electron-attracting compounds.

Examples of electron-attracting compounds other than the compounds represented by the formula (1) or (2) include organic electron-attracting compounds such as phenol derivatives, organic acids and metal salts thereof, complexes and urea derivatives; and inorganic electron-attracting compounds such as acid clay.

Specific examples of these compounds include organic electron-attracting compounds, for example, phenol derivatives such as 4-tert-butylphenol, 4-tert-octylphenol, 4-phenylphenol, 1-naphthol, 2-naphthol, hydroquinone, resorcinol, 4-tert-octylcatechol, 2,2'-dihydroxydiphenyl, 2,2-bis(4'-hydroxyphenyl)propane [also called "bisphenol A"], 1,1-bis(4'-hydroxyphenyl)cyclohexane, 2,2-bis(4'-hydroxy-3'-methylphenyl)propane, ethyl 2,2-bis(4'-hydroxyphenyl)acetate, n-butyl 4,4-(4'-hydroxyphenyl)pentanoate, benzyl 4-hydroxybenzoate, phenethyl 4-hydroxybenzoate, phenoxyethyl 2,4-dihydroxybenzoate, dimethyl 4-hydroxyphthalate, hydroquinonmonobenzyl ether, bis(3-methyl-4-hydroxyphenyl) sulfide, bis(2-methyl-4-hydroxyphenyl) sulfide, bis(3-phenyl-4-hydroxyphenyl) sulfide, bis(3-cyclohexyl-4-hydroxyphenyl) sulfide, bis(4-hydroxyphenyl) sulfoxide, bis(4-hydroxyphenyl) sulfone, bis(3-allyl-4-hydroxyphenyl) sulfone, 4-hydroxy-4'-methyldiphenyl sulfone, 4-hydroxy-4'-chlorodiphenyl sulfone, 4-hydroxy-4'-n-propoxydiphenyl sulfone, 4-hydroxy-4'-isopropoxydiphenyl sulfone, 4-hydroxy-4'-n-butoxydiphenyl sulfone, 3,4-dihydroxy-4'-methyldiphenyl sulfone, bis(2-hydroxy-4-tert-butylphenyl) sulfone, bis(2-hydroxy-4-chlorophenyl) sulfone, 4-hydroxybenzophenone, 2,4-dihydroxybenzophenone, 1,7-di(4-hydroxyphenylthio)-3,5-dioxaheptane and 1,5-di(4-hydroxyphenylthio)-3-oxapentane, organic acids such as salicyclic acid, 3-isopropylsalicyclic acid, 3-cyclohexylsalicyclic acid, 3,5-di-tert-butylsalicyclic acid, 3,5-di-α-methylbenzylsalicyclic acid, 3-methyl-5-α-methylbenzylsalicyclic acid, 4-[2'-(4-methoxyphenyloxy)ethyloxy]-salicylic acid, 2-hydroxy-3-naphthoic acid, 2-hydroxy-6-naphthoic acid, monobenzyl phthalate and monophenyl phthalate and metallic salts thereof (ex. nickel, zinc, aluminum and calcium salts), complexes such as zinc thiocyanate/antipyrine complexes and molybdic acid/acetylacetone complexes and urea derivatives such as phenylthiourea, di(3-trifluoromethylphenyl)thiourea and 1,4-di(3'-chlorophenyl)-3-thiosemicarbazide; and inorganic electron-attracting compounds such as acid clay, attapulgite, activated clay, aluminum chloride, zinc chloride and zinc bromide. Among them, phenol derivatives are particularly preferred as electron-attracting compounds.

These electron-attracting compounds can be used either singly or in combination.

In addition, in the heat-sensitive recording material according to the present invention, a thermo-fusible compound (a compound whose melting point is 60°–150° C., preferably about 80°–130° C.) can be added further to improve the color-producing sensitivity, if desired. This is preferred as it makes it possible to obtain a heat-sensitive recording material which is good in color-producing sensitivity and excellent in the storage stability of a color image to be produced. Particularly preferred are heat-sensitive recording materials using, as an electron-attracting compound, the compound represented by the formula (1) or (2) and the above-mentioned, known, electron-attracting compound (for example, one of the various phenol derivatives) in combination and heat-sensitive recording materials added further with a thermofusible compound.

In this case, it is generally desirable to use the thermo-fusible compound in an amount of 10–700 parts by weight, preferably 20–500 parts by weight per 100 parts by weight of the electron-donating chromogenic compound. Specific examples of such thermofusible compounds include nitrogen-containing compounds such as stearic acid amide, palmitic acid amide, stearyl urea, N-ethylcarbazole and 4-methoxydiphenylamine; esters such as benzyl 4-benzyloxybenxoate, phenyl 2-naphthoate, phenyl 1-hydroxy-2-naphthoate, dibenzyl oxalate, di(4-methylbenzyl) oxalate, di(4-chlorobenzyl) oxalate, diphenacyl glutarate, di(4-methylphenyl) carbonate and dibenzyl terephthalate; hydrocarbon compounds such as 4-benzylbiphenyl, m-terphenyl, fluorene and fluoranthene; and ether compounds such as 2-benzyloxynaphthalene, 2-(4'-methylbenzyloxy)naphthalene, 1,4-diethoxynaphthalene, 1,2-bis(3'-methylphenoxy)ethane, 1-phenoxy-2-(4-ethylphenoxy)ethane, 4-(4'-methylphenoxy)biphenyl, 1,4-bis(2'-chlorobenzyloxy)benzene, 4,4'-di-n-butoxydiphenyl sulfone, 1,2-diphenoxybenzene, 1,4-bis(3'-methylphenyloxymethyl)benzene and 4-chlorobenzyloxy(4'-ethoxybenzene). The ester compounds, hydrocarbon compounds and ether compounds are particularly preferred as thermofusible compounds.

These thermofusible compounds can be used either singly or in combination.

To produce the heat-sensitive recording material according to this invention, a conventional process can be followed without the need for relying upon any special process. In the heat-sensitive recording materials according to this invention, no particular limitation is imposed on the method for the formation of the recording layer. For example, a coating formulation for the heat-sensitive recording layer can be coated on a base by a suitable coating means such as an air knife coater, blade coater, bar coater, gravure coater, curtain coater or wire bar, and then dried to form a recording layer.

The coating formulation for the heat-sensitive recording layer can be prepared, generally, by separately grinding and dispersing an electron-donating chromogenic compound, the compound represented by the formula (1) or (2), etc., normally to 3 μm or smaller, preferably to 1.5 μm or smaller in a water-soluble binder in an apparatus such as a ball mill or sand mill and then mixing the resultant dispersions.

Specific examples of usable water-soluble binders include polyvinyl alcohol, hydroxyethylcellulose, hydroxypropylcellulose, epichlorohydrin-modified polyamide, ethylene-maleic anhydride copolymer, styrene-maleic anhydride copolymer, isobutylene-maleic anhydride copolymer, polyacrylic acid, polyacrylamide, methylol-modified polyacrylamide, starch derivatives, casein, gelatin, methylcellulose, carboxymethylcellulose, gum arabic, and carboxyl-modified polyvinyl alcohol.

The recording layer of the heat-sensitive recording material according to this invention can be added, as needed, with a pigment, a water-insoluble binder, a metal soap, a wax, a surfactant, an ultraviolet absorber, a hindered phenol, a defoaming agent, etc.

Usable examples of pigments include zinc oxide, zinc carbonate, calcium carbonate, magnesium carbonate, barium carbonate, barium sulfate, titanium oxide, talc, agalmatolite, kaolin, diatomaceous earth, aluminum hydroxide, magnesium hydroxide, alumina, silica, amorphous silica, urea-formaldehyde filler, polyethylene particles, and cellulose filler.

As the water-insoluble binder, a synthetic rubber latex or synthetic resin emulsion is usually employed. Known examples include styrene-butadiene rubber latex, acrylonitrile-butadiene latex, methyl acrylate-butadiene rubber latex, and vinyl acetate emulsion. They can be used as needed.

As the metal soap, a higher fatty acid metal salt is used. Usable examples include zinc stearate, calcium stearate, and aluminum stearate.

Illustrative examples of waxes include paraffin wax, microcrystalline wax, carboxyl-modified paraffin wax, carnauba wax, polyethylene wax, polystyrene wax, and higher fatty acid esters.

Examples of surfactants include alkali metal sulfosuccinates and fluorine-containing surfactants.

Examples of ultraviolet absorbers include cinnamic acid derivatives, benzophenone derivatives, benzotriazolylphenol derivatives.

Preferred as the hindered phenol is a phenol derivative with a branched alkyl group substituted to at least one of the ortho positions relative to the phenolic hydroxyl group. Examples include 1,1,3-tris(2-methyl-4-hydroxy-5-tert-butylphenyl)butane, 1,1,3tris(2-methyl-4-hydroxy-5-cyclohexylphenyl)butane, 1,1,3-tris(2-ethyl-4-hydroxy-5-tert-butylphenyl)butane, 1,1,3-tris(3,5-di-tert-butyl-4-hydroxyphenyl)butane, 1,1,3-tris(2-methyl-4-hydroxy-5-tert-butylphenyl)propane, 2,2-methylene-bis-(6-tert-butyl-4-methylphenol), 2,2-methylene-bis-(6-tert-butyl-4-ethylphenol), 1,3,5-trimethyl-2,4,6-tris(3,5-di-tert-butyl-4-hydroxybenzyl)benzene, 1,3,5-tris(4-tert-butyl-3-hydroxy-2,6-dimethylbenzyl)isocyanuric acid, 1,3,5-tris-(4-tert-butyl-3-hydroxy-2-methyl-6-ethylbenzyl)isocyanuric acid, and bis(2-methyl-4-hydroxy-5-tert-butylphenyl) sulfide.

No particular limitation is imposed on the amount of the coating formulation to be applied. It can be coated in an amount sufficient to give a dry weight in a range of 1.5–12 g/m$^2$, preferably 2.5–10 g/m$^2$. As the base, a paper sheet, plastic sheet, a synthetic paper sheet or the like can be used.

Various techniques known in the production of heat-sensitive recording materials can be applied as needed. For example, a protective layer can be arranged on the upper and/or lower surfaces of the heat-sensitive recording layer, or a prime coat can be provided between the base and the heat-sensitive recording layer. Further, tackifying treatment can also be applied.

The present invention will hereinafter be described specifically by the following preparation examples and examples. It should however be borne in mind that this invention is by no means limited to or by the examples In the examples, all designations of "%" mean wt. %.

Preparation Example 1 (Preparation of Exemplified Compound No. 1)

Methyl chloroformate (22.7 g) was added dropwise to a suspension of 45.4 g of 2-(4'-hydroxyphenyl)-2-(4"-aminophenyl)propane and 10.6 g of sodium carbonate in 300 ml of ethyl acetate. After they were reacted at room temperature under stirring for 12 hours, the reaction mixture was filtered. Water (200 ml) was added to the resultant filtrate to wash the same. That procedure was repeated until the water layer became neutral. The reaction mixture was allowed to separate into layers. The ethyl acetate layer was collected and, then, ethyl acetate was distilled off under reduced pressure at 40° C., whereby a slightly yellowish crude product was obtained in a solid form. The product was recrystallized from 150 ml of toluene and then dried at 40° C. for 24 hours, whereby 51.3 g of 2-(4'-hydroxyphenyl)-2-(4"-methoxycarbonylaminophenyl)propane were obtained as white crystals.

yield: 90%. Melting Point: 104°–105.5° C. $^1$H-NMR, $\delta$(CDCl$_3$):1.6(s,6H), 3.8(s,3H), 5.1(s,1H), 6.5–7.4(m,9H).

Preparation Example 2(Preparation of Exemplified Compound No. 2)

In a similar manner to Preparation Example 1 except for the replacement of methyl chloroformate by n-propyl chloroformate, 2-(4'-hydroxyphenyl)-2-(4"n-propoxycarbonylaminophenyl)propane was obtained.

Melting Point: 146°–147.5° C. $^1$H-NMR, $\delta$(CDCl$_3$): 0.8–1.1(t,3H), 1.6(s,6H) 1.7–1.9(m,2H), 4.0–4.2(t,2H), 5.4(s,1H), 6.5–7.4(m,9H).

Preparation Example 3 (Preparation of Exemplified Compound No. 3)

In a similar manner to Preparation Example 1 except for the replacement of methyl chloroformate by n-butyl chloroformate, 2-(4'-hydroxyphenyl)-2-(4"-n-butoxycarbonylaminophenyl)propane was obtained.

Melting Point: 89°–91° C. $^1$H-NMR, $\delta$(CDCl$_3$): 0.9–1.1(t,3H), 1.3–1.9(m,10H), 4.1–4.3(m,2H), 5.4–5.6(br,1H), 6.6–7.4(m,9H).

Preparation Example 4 (Preparation of Exemplified Compound No. 5)

In a similar manner to Preparation Example 1 except for the replacement of methyl chloroformate by n-hexadecyl chloroformate, 2-(4'-hydroxyphenyl)-2-(4"-n-hexadecyloxycarbonylaminophenyl)propane was obtained.

Melting Point: 63.5°65° C. $^1$H-NMR, $\delta$(CDCl$_3$): 0.9–1.1(t,3H), 1.1–2.0(m,36H), 4.1–4.3(t,2H), 5.4–5.6(br,1H) , 6.6–7.4(m,9H). Preparation Example 5 (Preparation of Exemplified Compound No. 6)

In a similar manner to Preparation Example 1 except for the replacement of methyl chloroformate by cyclohexyl chloroformate, 2-(4'-hydroxyphenyl)-2-(4"-cyclohexyloxycarbonylaminophenyl)propane was obtained.

Melting Point: 136°–137.5° C. $^1$H-NMR, $\delta$(CDCl$_3$): 1.1–2.1(m,16H), 4.7–4.9(br,1H), 5.3–5.5(br,1H), 6.5–7.5(m,9H).

Preparation Example 6 (Preparation of Exemplified Compound No. 9)

In a similar manner to Preparation Example 1 except for the replacement of methyl chloroformate by 2-methoxyethyl chloroformate, 2-(4'-hydroxyphenyl)-2-[4"-(2-methoxyethyl)oxycarbonylaminophenyl]propane was obtained.

Melting Point: 84°–86° C. $^1$H-NMR, $\delta$(CDCl$_3$): 1.6(s,6H), 3.4(s,3H), 3.6–3.8(m,2H), 4.2–4.4(m,2H), 5.8–6.0(br,1H), 6.6–7.4(m,9H) . Preparation Example 7 (Preparation of Exemplified Compound No. 14)

In a similar manner to Preparation Example 1 except for the replacement of methyl chloroformate by 2-phenoxyethyl chloroformate, 2-(4'-hydroxyphenyl)-2-[4"-(2-phenoxyethyl)oxycarbonylaminophenyl]propane was obtained.

Melting Point: 98°–100° C. $^1$H-NMR, $\delta$(CDCl$_3$): 1.6(s,6H), 4.1–4.3(m,2H), 4.4–4.6(m,2H), 5.3–5.5(br,1H), 6.6–7.4(m,14H).

Preparation Example 8 (Preparation of Exemplified Compound No. 17)

In a similar manner to Preparation Example 1 except for the replacement of methyl chloroformate by allyl chloroformate, 2-(4'-hydroxyphenyl)-2-(4"-allyloxycarbonylaminophenyl)propane was obtained.

Melting Point: 109°–111° C. $^1$H-NMR, $\delta$(CDCl$_3$): 1.6(s,6H), 4.6–4.8(d,2H), 5.1–5.5(m,3H), 5.7–6.2(m,1H), 6.6–7.4(m,9H).

Preparation Example 9 (Preparation of Exemplified Compound No. 18)

In a similar manner to Preparation Example 1 except for the replacement of methyl chloroformate by benzyl chloroformate, 2-(4'-hydroxyphenyl)-2-(4"-benzyloxycarbonylaminophenyl)propane was obtained.

Melting Point: 69°–74° C. $^1$H-NMR, δ(CDCl$_3$): 1.6(s,6H), 5.0–5.2(m,2H), 5.3(s,1H), 6.6–7.4(m,14H).

Preparation Example 10 (Preparation of Exemplified Compound No. 23)

In a similar manner to Preparation Example 1 except for the replacement of methyl chloroformate by 2-phenylethyl chloroformate, 2-(4'-hydroxyphenyl)-2-[4''-(2-Phenylethyl)oxycarbonylaminophenyl]propane was obtained.

Melting Point: 121°–123° C. $^1$H-NMR, δ(CDCl$_3$): 1.6(s,6H), 2.8–3.1(t,2H), 4.2–4.5(t,2H), 5.4–5.5(br,1H), 6.6–7.4(m,14H).

Preparation Example 11 (Preparation of Exemplified Compound No. 24)

In a similar manner to Preparation Example 1 except for the replacement of methyl chloroformate by phenyl chloroformate, 2-(4'-hydroxyphenyl)-2-(4''-phenyloxycarbonylaminophenyl)propane was obtained.

Melting Point: 116°–120° C. $^1$H-NMR, δ(CDCl$_3$): 1.6(s,6H), 5.3(s,1H), 6.6–7.5(m,14H).

Preparation Example 12 (Preparation of Exemplified Compound No. 26)

In a similar manner to Preparation Example 1 except for the replacement of methyl chloroformate by 4-phenylphenyl chloroformate, 2-(4'-hydroxyphenyl)-2-[4''-(4-phenylphenyl)oxycarbonylaminophenyl]propane was obtained.

Melting Point: 171°–173° C. $^1$H-NMR, δ(CDCl$_3$): 1.6(s,6H), 5.3(s,1H), 6.6–7.5(m,18H).

Preparation Example 13 (Preparation of Exemplified Compound No. 27)

In a similar manner to Preparation Example 1 except for the replacement of methyl chloroformate by 4-methylphenyl chloroformate, 2-(4'-hydroxyphenyl)-2-[4''-(4-methylphenyl)oxycarbonylaminophenyl]propane was obtained.

Melting Point: 146°–148° C. $^1$H-NMR, δ(CDCl$_3$): 1.6(s,6H), 2.4(s,3H), 4.5(br,1H), 6.6–7.4(m,13H).

Preparation Example 14 (Preparation of Exemplified Compound No. 28)

In a similar manner to Preparation Example 1 except for the replacement of methyl chloroformate by 3-methylphenyl chloroformate, 2-(4'-hydroxyphenyl)-2-[4''-(3-methylphenyl)oxycarbonylaminophenyl]propane was obtained.

Melting Point: 133°–136° C. $^1$H-NMR, δ(CDCl$_3$): 1.6(s,6H), 2.4(s,3H), 5.0(br,1H), 6.6–7.4(m,13H).

Preparation Example 15 (Preparation of Exemplified Compound No. 30)

In a similar manner to Preparation Example 1 except for the replacement of methyl chloroformate by 4-cumylphenyl chloroformate, 2-(4'-hydroxyphenyl)-2-[4''-(4-cumylphenyl)oxycarbonylaminophenyl]propane was obtained.

Melting Point: 146°–148° C. $^1$H-NMR, δ(CDCl$_3$): 1.5–1.7(m,12H), 4.8(s,1H), 6.6–7.4(m,18H).

Preparation Example 16 (Preparation of Exemplified Compound No. 31)

In a similar manner to Preparation Example 1 except for the replacement of methyl chloroformate by 4-methoxyphenyl chloroformate, 2-(4'-hydroxyphenyl)-2-[4''-(4-methoxyphenyl)oxycarbonylaminophenyl]propane was obtained.

Melting Point: 125°–127° C. $^1$H-NMR, δ(CDCl$_3$): 1.6(s,6H), 3.8(s,3H), 5.0(br,1H), 6.6–7.4(m,13H).

Preparation Example 17 (Preparation of Exemplified Compound No. 33)

In a similar manner to Preparation Example 1 except for the replacement of methyl chloroformate by 4-chlorophenyl chloroformate, 2-(4'-hydroxyphenyl)-2-[4''-(4-chlorophenyl)oxycarbonylaminophenyl]propane was obtained.

Melting Point: 162°–164° C. $^1$H-NMR, δ(CDCl$_3$): 1.6(s,6H), 4.6(s,1H), 6.6–7.4(m, 13H).

Preparation Example 18 (Preparation of Exemplified Compound No. 34)

In a similar manner to Preparation Example 1 except for the replacement of methyl chloroformate by 2-chlorophenyl chloroformate, 2-(4'-hydroxyphenyl)-2-[4''(2-chlorophenyl)oxycarbonylaminophenyl]propane was obtained.

Melting Point: 97°–99° C. $^1$H-NMR, δ(CDCl$_3$): 1.6(s,6H), 4.6(s,1H), 6.6–7.4(m,13H).

Preparation Example 19 (Preparation of Exemplified Compound No. 41)

In a similar manner to Preparation Example 1 except for the replacement of methyl chloroformate by 2,4-dimethylphenyl chloroformate, 2-(4'-hydroxyphenyl)-2-[4''-(2,4-dimethylphenyl)oxycarbonylaminophenyl]propane was obtained.

Melting Point: 156°–157° C. $^1$H-NMR, δ(CDCl$_3$): 1.6(s,6H), 2.2(s,3H), 2.4(s,3H), 5.0–5.1(br, 1H), 6.6–7.4(m,12H).

Preparation Example 20 (Preparation of Exemplified Compound No. 62)

In a similar manner to Preparation Example 1 except for the replacement of methyl chloroformate by S-phenyl chlorothioformate, 2-(4'-hydroxyphenyl)-2-(phenylthiolcarbonylaminophenyl)propane was obtained.

Melting Point: 118°–121° C. $^1$H-NMR, δ(CDCl$_3$): 1.6(s,6H), 5.3(s,1H), 6.6–7.5(m,14H).

Preparation Example 21 (Preparation of Exemplified Compound No. 65)

Methyl chloroformate (11.4 g) was added dropwise to a suspension of 22.7 g of 2-(3'-hydroxyphenyl)-2-(4''-aminophenyl)propane and 5.3 g of sodium carbonate in 100 ml of ethyl acetate. After they were reacted at room temperature under stirring for 12 hours, the reaction mixture was filtered. Water (200 ml) was added to the resultant filtrate to wash the same. That procedure was repeated until the water layer became neutral. The reaction mixture was allowed to separate into layers. The ethyl acetate layer was collected and, then, ethyl acetate was distilled off under reduced pressure at 40° C., whereby a slightly yellowish crude product was obtained in a solid form. The product was recrystallized from 100 ml of toluene and then dried at 40° C. for 24 hours, whereby 26.2 g of 2-(3'-hydroxyphenyl)-2-(4''-methoxycarbonylaminophenyl)propane were obtained as white crystals.

yield: 92%. Melting Point: 137°–139° C. $^1$H-NMR, δ(CDCl$_3$): 1.6(t,3H), 3.8(s,3H), 5.1(s,1H), 6.5–7.4(m,9H).

Preparation Example 22 (Preparation of Exemplified Compound No. 66)

In a similar manner to Preparation Example 21 except for the replacement of methyl chloroformate by n-butyl chloroformate, 2-(3'-hydroxyphenyl)-2-(4''-n-butoxycarbonylaminophenyl)propane was obtained.

Melting Point: 101°–104° C. $^1$H-NMR, $\delta$(CDCl$_3$): 0.8–1.1(t,3H), 1.6(s,6H), 1.7–1.9(m,2H), 4.0–4.2(t,2H), 5.0(s,1H), 6.5–7.4(m,9H).

Preparation Example 23 (Preparation of Exemplified Compound No. 70)

In a similar manner to Preparation Example 21 except for the replacement of methyl chloroformate by phenyl chloroformate, 2-(3'-hydroxyphenyl)-2-(4''-phenyloxycarbonylaminophenyl)propane was obtained.

Melting Point: 119°–124° C. $^1$H-NMR, $\delta$(CDCl$_3$): 1.6(s,6H), 5.0(br, 1H), 6.6–7.5(m,14H).

Preparation Example 24 (Preparation of Exemplified Compound No. 77)

In a similar manner to Preparation Example 21 except for the replacement of methyl chloroformate by 4-chlorophenyl chloroformate, 2-(3'-hydroxyphenyl)-2-[4''-(4-chlorophenyl)oxycarbonylaminophenyl]propane was obtained.

Melting Point: 112°–116° C. $^1$H-NMR, $\delta$(CDCl$_3$): 1.6(s,3H), 5.0(br,1H), 6.6–7.5(m,13H).

Preparation Example 25 (Preparation of Exemplified Compound No. 78)

In a similar manner to Preparation Example 21 except for the replacement of methyl chloroformate by 2-chlorophenyl chloroformate, 2-(3'-hydroxyphenyl)-2-[4''-(2-chlorophenyl)oxycarbonylaminophenyl]propane was obtained.

Melting Point: 95°–101° C. $^1$H-NMR, $\delta$(CDCl$_3$): 1.6(s,3H), 5.0(br,1H), 6.6–7.5(m,13H).

Preparation Example 26 (Preparation of Exemplified Compound No. 117)

Methyl chloroformate (5.2 g) was added dropwise to a suspension of 10.0 g of 4-(4'-aminophenoxy)phenol and 4.6 g of sodium hydrogencarbonate in 50 ml of ethyl acetate. They were reacted at room temperature under stirring for 12 hours. Water (100 ml) was thereafter added to the reaction mixture to wash the same. That procedure was repeated until the water layer became neutral. The reaction mixture was allowed to separate into layers. The ethyl acetate layer was collected and, then, ethyl acetate was distilled off under reduced pressure at 40° C., whereby a slightly yellowish crude product was obtained in a solid form. The product was recrystallized from 500 ml of toluene and then dried at 40° C. for 24 hours, whereby 11.0 g of 4-hydroxyphenyl-4'-methoxycarbonylaminophenyl ether were obtained as white crystals.

yield: 85%. Melting Point: 104°–108° C. $^1$H-NMR, $\delta$(CDCl$_3$): 1.1(s,3H), 6.7–7.8(m,6H), 7.3–7.8(m,2H), 8.2(s,1H), 8.3–8.4(br,1H).

Preparation Example 27 (Preparation of Exemplified Compound No. 118)

In a similar manner to Preparation Example 26 except for the replacement of methyl chloroformate by ethyl chloroformate, 4-hydroxyphenyl-4'-ethoxycarbonylaminophenyl ether was obtained.

Melting Point: 117°–118° C. $^1$H-NMR, $\delta$(CDCl$_3$): 1.2(t,3H), 4.2(q,2H), 6.8–7.0(m,6H), 7.4–7.7(m,2H), 8.1(s,1H), 8.2–8.4(br,1H).

Preparation Example 28 (Preparation of Exemplified Compound No. 119)

In a similar manner to Preparation Example 26 except for the replacement of methyl chloroformate by n-butyl chloroformate, 4-hydroxyphenyl-4'-n-butoxycarbonylaminophenyl ether was obtained.

Melting Point: 118°–119° C. $^1$H-NMR, $\delta$(CDCl$_3$): 1.2–4.3(m,9H), 6.8–7.1(m,6H), 7.3–7.6(m,2H), 8.0(s,1H), 8.3–8.4(br,1H).

Preparation Example 29 (Preparation of Exemplified Compound No. 120)

In a similar manner to Preparation Example 26 except for the replacement of methyl chloroformate by n-hexyl chloroformate, 4-hydroxyphenyl-4'-n-hexyloxycarbonylaminophenyl ether was obtained.

Melting Point: 120°–122° C. $^1$H-NMR, $\delta$(CDCl$_3$): 1.1–4.1(m,13H), 6.4–6.9(m,6H), 7.4–7.6(m, 2H), 8.1–8.3(br,1H), 8.3(s,1H)

Preparation Example 30 (Preparation of Exemplified Compound No. 121)

In a similar manner to Preparation Example 26 except for the replacement of methyl chloroformate by n-hexadecyl chloroformate, 4-hydroxyphenyl-4'-n-hexadecyloxycarbonylaminophenyl ether was obtained.

Melting Point: 123°–124° C. $^1$H-NMR, $\delta$(CDCl$_3$): 1.1–4.5(m,33H), 6.9–7.8(m,8H), 8.1(s,1H), 8.2–8.4(br,1H).

Preparation Example 31 (Preparation of Exemplified Compound No. 122)

In a similar manner to Preparation Example 26 except for the replacement of methyl chloroformate by 2-methoxyethyl chloroformate, 4-hydroxyphenyl-4'-(2-methoxyethyl)oxycarbonylaminophenyl ether was obtained.

Melting Point: 89°–90° C. $^1$H-NMR, $\delta$(CDCl$_3$): 1.5(s,3H), 3.6–4.2(m,4H), 6.9–7.1(m,6H), 7.4–7.8(m,2H), 8.1(s,1H), 8.4–8.5(br,1H).

Preparation Example 32 (Preparation of Exemplified Compound No. 125)

In a similar manner to Preparation Example 26 except for the replacement of methyl chloroformate by benzyl chloroformate, 4-hydroxyphenyl-4'-benzyloxycarbonylaminophenyl ether was obtained.

Melting Point: 148°–150° C. $^1$H-NMR, $\delta$(CDCl$_3$): 4.2(s,2H), 6.9–7.8(m,13H), 8.2(s,1H), 9.0–9.2(br,1H)

Preparation Example 33 (Preparation of Exemplified Compound No. 126)

In a similar manner to Preparation Example 26 except for the replacement of methyl chloroformate by phenyl chloroformate, 4-hydroxyphenyl-4'-phenyloxycarbonylaminophenyl ether was obtained.

Melting Point: 158°–161° C. $^1$H-NMR, $\delta$(CDCl$_3$): 6.8–7.6(m,13H), 8.2(s,1H), 8.9–9.2(br,1H).

Preparation Example 34 (Preparation of Exemplified Compound No. 128)

In a similar manner to Preparation Example 26 except for the replacement of methyl chloroformate by 4-phenylphenyl chloroformate, 4-hydroxyphenyl-4'-(4- phenylphenyl)oxycarbonylaminophenyl ether was obtained.

Melting Point: 264°–270° C. $^1$H-NMR, δ(CDCl$_3$): 6.4–7.9(m,17H), 8.2(s,1H), 8.9–9.2(br,1H).

Preparation Example 35 (Preparation of Exemplified Compound No. 131)

In a similar manner to Preparation Example 26 except for the replacement of methyl chloroformate by 3-chlorophenyl chloroformate, 4-hydroxyphenyl-4'-(3-chlorophenyl)oxycarbonylaminophenyl ether was obtained.

Melting Point: 121°–125° C. $^1$H-NMR, δ(CDCl$_3$): 6.8–7.9(m,12H), 8.4(s,1H), 8.7–9.1(br,1H).

Preparation Example 36 (Preparation of Exemplified Compound No. 134)

In a similar manner to Preparation Example 26 except for the replacement of methyl chloroformate by S-phenyl chlorothioformate, 4-hydroxyphenyl-4'-phenylthiolcarbonylaminophenyl ether was obtained.

Melting Point: 138°–140° C. $^1$H-NMR, δ(CDCl$_3$): 6.6–7.9(m,13H), 8.1(s,1H), 9.0–9.2(br,1H).

Preparation Example 37 (Preparation of Exemplified Compound No. 136)

Methyl chloroformate (11.3 g) was added dropwise to a suspension of 20.0 g of 3-(4'-aminophenoxy)phenol and 9.2 g of sodium hydrogencarbonate in 100 ml of ethyl acetate. They were reacted at room temperature under stirring for 9 hours. Water (100 ml) was thereafter added to the reaction mixture to wash the same. That procedure was repeated until the water layer became neutral. The reaction mixture was allowed to separate into layers. The ethyl acetate layer was collected and, then, ethyl acetate was distilled off under reduced pressure at 40° C., whereby a slightly brownish crude product was obtained in a solid form. The product was recrystallized from 700 ml of toluene and then dried at 40° C. for 24 hours, whereby 21.7 g of 3-hydroxyphenyl-4'-methoxycarbonylaminophenyl ether were obtained as white crystals.

yield: 80%. Melting Point: 95°–96° C. $^1$H-NMR, δ(CDCl$_3$): 1.1(s,3H), 6.7–7.1l(m,6H), 7.3–7.8(m,8H), 8.5(s,1H), 9.0–9.3(br,1H).

Preparation Example 38 (Preparation of Exemplified Compound No. 137)

In a similar manner to Preparation Example 37 except for the replacement of methyl chloroformate by ethyl chloroformate, 3-hydroxyphenyl-4'-ethoxycarbonylaminophenyl ether was obtained.

Melting Point: 126°–128° C. $^1$H-NMR, δ(CDCl$_3$): 1.2(t,3H), 4.1(q,2H), 6.3–7.8(m,8H), 8.3–8.7(m,2H).

Preparation Example 39 (Preparation of Exemplified Compound No. 138)

In a similar manner to Preparation Example 37 except for the replacement of methyl chloroformate by n-octyl chloroformate, 3-hydroxyphenyl-4'-n-octyloxycarbonylaminophenyl ether was obtained.

Melting Point: 102°–104° C.

Preparation Example 40 (Preparation of Exemplified Compound No. 140)

In a similar manner to Preparation Example 37 except for the replacement of methyl chloroformate by phenyl chloroformate, 3-hydroxyphenyl-4'-phenyloxycarbonylaminophenyl ether was obtained.

Melting Point: 132°–134° C. $^1$H-NMR, δ(CDCl$_3$): 6.3–6.7(m,5H), 6.9–7.8(m,8H), 8.5(s,1H), 9.0–9.3(br,1H).

Preparation Example 41 (Preparation of Exemplified Compound No. 144)

In a similar manner to Preparation Example 37 except for the replacement of methyl chloroformate by 4-methoxyphenyl chloroformate, 3-hydroxyphenyl-4'-(3methoxyphenyl)oxycarbonylaminophenyl ether was obtained.

Melting Point: 133°–136° C.

Preparation Example 42 (Preparation of Exemplified Compound No. 145)

In a similar manner to Preparation Example 37 except for the replacement of methyl chloroformate by 3-chlorophenyl chloroformate, 3-hydroxyphenyl-4'-(3chlorophenyl)oxycarbonylaminophenyl ether was obtained.

Melting Point: 101°–110° C. $^1$H-NMR, δ(CDCl$_3$): 6.5–7.6(m,5H), 6.9–7.8(m,7H), 8.6(s,1H), 9.0–9.3(br,1H).

Preparation Example 43 (Preparation of Exemplified Compound No. 157)

Ethyl chloroformate (8.3 g) was added dropwise to a suspension of 14.9 g of 4-amino-4'-hydroxydiphenyl sulfide and 6.0 g of sodium hydrogencarbonate in 50 ml of ethyl acetate. They were reacted at room temperature under stirring for 12 hours. Water (200 ml) was thereafter added to the reaction mixture to wash the same. That procedure was repeated until the water layer became neutral. The reaction mixture was allowed to separate into layers. The ethyl acetate layer was collected and, then, ethyl acetate was distilled off under reduced pressure at 40° C., whereby a slightly yellowish crude product was obtained in a solid form. The product was recrystallized from 500 ml of toluene and then dried at 40° C. for 24 hours, whereby 17.3 g of 4-hydroxyphenyl-4'-ethoxycarbonylaminophenyl sulfide were obtained as white crystals.

yield: 87%. Melting Point: 87°–88° C. $^1$H-NMR, δ(CDCl$_3$): 1.3(t,3H), 4.2(q,2H), 5.3(br,1H), 6.7–6.9(m,3H), 7.0–7.4(m,6H).

Preparation Example 44 (Preparation of Exemplified Compound No. 158)

In a similar manner to Preparation Example 43 except for the replacement of ethyl chloroformate by isobutyl chloroformate, 4-hydroxyphenyl-4'-isobutoxycarbonylaminophenyl sulfide was obtained.

yield: 64%. Melting Point: 114°–116° C. $^1$H-NMR, δ(CDCl$_3$): 0.9(d,6H), 1.8–2.0(m,1H), 3.9(d,2H), 5.1(br,1H), 6.7–6.9(m,3H), 7.1–7.4(m,6H).

Preparation Example 45 (Preparation of Exemplified Compound No. 159)

In a similar manner to Preparation Example 43 except for the replacement of ethyl chloroformate by n-hexadecyl chloroformate, 4-hydroxyphenyl-4'-n-hexadecyloxycarbonylaminophenyl sulfide was obtained.

yield: 83%. Melting Point: 114°–116° C. $^1$H-NMR, δ(CDCl$_3$): 1.3(br,31H), 4.1(t,2H), 5.0(br,1H), 6.7–6.9(m,3H), 7.2–7.4(m,6H).

Preparation Example 46 (Preparation of Exemplified Compound No. 161)

In a similar manner to Preparation Example 43 except for the replacement of ethyl chloroformate by 2-methoxyethyl chloroformate, 4-hydroxyphenyl-4'-(2-methoxyethyl)oxycarbonylaminophenyl sulfide was obtained.

Melting Point: 82°–84° C. $^1$H-NMR, $\delta$(CDCl$_3$): 3.4(s,3H), 3.6–3.7(m,2H), 4.3–4.4(m,2H), 5.2(br,1H), 6.6–6.9(m,3H), 7.1–7.7 (m,6H).

Preparation Example 47 (Preparation of Exemplified Compound No. 165)

In a similar manner to Preparation Example 43 except for the replacement of ethyl chloroformate by phenyl chloroformate, 4-hydroxyphenyl-4'-phenyloxycarbonylaminophenyl sulfide was obtained.

Melting Point: 151°–153° C. $^1$H-NMR, $\delta$(CDCl$_3$): 4.9(br,1H), 6.7–6.9(m,3H), 7.1–7.6(m,11H)

Preparation Example 48 (Preparation of Exemplified Compound No. 172)

In a similar manner to Preparation Example 43 except for the replacement of ethyl chloroformate by S-phenyl chlorothioformate, 4-hydroxyphenyl-4'-phenylthiolcarbonylaminophenyl sulfide was obtained.

Melting Point: 243°–248° C. $^1$H-NMR, $\delta$(CDCl$_3$): 5.1(br,1H), 6.8–6.9(m,3H), 7.3–7.8(m,11H)

Preparation Example 49 (Preparation of Exemplified Compound No. 192)

Phenyl chloroformate (15.0 g) was added dropwise to a suspension of 26.4 g of 4''-aminophenyl-4-(4'-hydroxy)phenylbenzoate and 8.0 g of sodium hydrogencarbonate in 120 ml of ethyl acetate. They were reacted at room temperature under stirring for 12 hours. Water (300 ml) was thereafter added to the reaction mixture to wash the same. That procedure was repeated until the water layer became neutral. The reaction mixture was allowed to separate into layers. The ethyl acetate layer was collected and, then, ethyl acetate was distilled off under reduced pressure at 40° C., whereby a slightly yellowish crude product was obtained in a solid form. The product was recrystallized from 900 ml of toluene and then dried at 40° C. for 24 hours, whereby 27.7 g of 4''-phenyloxycarbonylaminophenyl-4-(4'-hydroxy)phenylbenzoate were obtained as white crystals.

yield: 75%. Melting Point: >300° C. $^1$H-NMR, $\delta$(CDCl$_3$): 6.8–7.6(m,17H), 8.2(s,1H), 8.9–9.2(br,1H)

Preparation Example 50 (Preparation of Exemplified Compound No. 193)

Phenyl chloroformate (7.5 g) was added dropwise to a suspension of 13.2 g of 3''-aminophenyl-4-(4'-hydroxy)phenylbenzoate and 4.0 g of sodium hydrogencarbonate in 50 ml of ethyl acetate. They were reacted at room temperature under stirring for 12 hours. Water (200 ml) was thereafter added to the reaction mixture to wash the same. That procedure was repeated until the water layer became neutral. The reaction mixture was allowed to separate into layers. The ethyl acetate layer was collected and, then, ethyl acetate was distilled off under reduced pressure at 40° C., whereby a slightly yellowish crude product was obtained in a solid form. The product was recrystallized from 900 ml of toluene and then dried at 40° C. for 24 hours, whereby 13.9 g of 3''-phenyloxycarbonylaminophenyl-4-(4'-hydroxy)phenylbenzoate were obtained as white crystals.

yield: 75%. Melting Point: >300° C. $^1$H-NMR, $\delta$(CDCl$_3$): 6.8–7.6(m,17H), 8.2(s,1H), 8.9–9.2(br,1H)

Preparation Example 51 (Preparation of Exemplified Compound No. 194)

Ethyl chloroformate (7.7 g) was added dropwise to a suspension of 14.9 g of 4'-hydroxyphenyl-4-aminobenzoate and 6.0 g of sodium hydrogencarbonate in 50 ml of ethyl acetate. They were reacted at room temperature under stirring for 12 hours. Water (200 ml) was thereafter added to the reaction mixture to wash the same. That procedure was repeated until the water layer became neutral. The reaction mixture was allowed to separate into layers. The ethyl acetate layer was collected and, then, ethyl acetate was distilled off under reduced pressure at 40° C., whereby a slightly yellowish crude product was obtained in a solid form. The product was recrystallized from 500 ml of toluene and then dried at 40° C. for 24 hours, whereby 14.9 g of 4'-hydroxyphenyl-4-ethoxycarbonylaminobenzoate were obtained as white crystals.

yield: 76%. Melting Point: >300° C. $^1$H-NMR, $\delta$(CDCl$_3$): 1.2(t,3H), 4.2(q,2H) 6.8–7.0 (m,6H), 7.4–7.7(m, 2H), 8.1(s,1H), 8.2–8.4(br,1H).

[Evaluation methods for heat-sensitive recording paper]

(Storage stability test of produced color image)

Using a color-producing apparatus for heat-sensitive recording paper ("TH-PMD" trade name; manufactured by Okura Denki K.K.), a color image having a color density of 0.9 as measured by a Macbeth densitometer ("TR-524 Model") was formed on a heat-sensitive recording paper produced in each of the below-described examples. Each heat-sensitive recording paper was then observed as to whether the image area presented the whitening phenomenon or not, and was then subjected to the below-described storage stability tests.

1. Heat resistance test

After each heat-sensitive recording paper had been stored at 60° C. for 24 hours, the density of the produced color image was measured by the Macbeth densitometer so that the percent remainder of the produced color image was determined.

2. Hydrothermoresistance test

After each heat-sensitive recording paper had been stored at 60° C. and 90% R.H. for 24 hours, the density of the produced color image was measured by the Macbeth densitometer so that the percent remainder of the produced color image was determined.

3. Waterproofness test

After each heat-sensitive recording paper had been stored at 25° C. for 24 hours in water, the density of the produced color image was measured by the Macbeth densitometer so that the percent remainder of the produced color image was determined.

4. Oil resistance test

Each heat-sensitive recording paper and a paper, which was coated with dioctyl-phthalate-containing capsules were brought into a contiguous relationship and then caused to pass through a pressure roll. After the heat-sensitive recording paper had been stored at 25° C. for 1 week, the density of the color image so produced was measured by the Macbeth densitometer so that the percent remainder of the produced color image was determined.

The percent remainder of each produced color image after each test was determined in accordance with the following formula:

$$\text{Percent remainder} = \frac{\text{Density of produced color image after each test}}{\text{Density of produced color image before the test (0.9)}} \times 100$$

A greater value indicates better storage stability of produced color image.

(Color-producing performance test)

Each heat-sensitive recording paper was maintained for 5 seconds in contact with a metal block heated at a surface temperature of 150° C. The density of a color image so produced was measured using the Macbeth densitometer ("TR-524" Model). A greater value indicates a higher color density. From the practical viewpoint, the density of each color image so produced is considered to be sufficient as long as it is not smaller than 1.

(Temperature-dependent color-producing performance test)

Each heat-sensitive recording paper was maintained for 5 minutes in contact with metal blocks heated at varied surface temperatures. The densities of color images so produced were measured using the Macbeth densitometer ("TR-524" Model). A greater value indicates a higher color density.

EXAMPLES 1–34

(Production method of heat-sensitive recording papers)

(Composition of Liquid A)

| | |
|---|---|
| Electron-donating chromogenic compound | 10 g |
| 10% Aqueous solution of polyvinyl alcohol ("Kuraray-117", trade name; product of Kuraray Co., Ltd.) | 10 g |
| Water | 80 g |
| Total | 100 g |

(Composition of Liquid B)

| | |
|---|---|
| Electron-attracting compound | 20 g |
| Precipitated calcium carbonate ("TP-123", trade name; product of Okutama Kogyo K.K.) | 40 g |
| 10% Aqueous solution of polyvinyl alcohol ("Kuraray-117", trade name; product of Kuraray Co., Ltd.) | 60 g |
| Water | 130 g |
| Total | 250 g |

Liquid A and Liquid B were separately dispersed to an average particle size of 1.5 μm or smaller in a sand grinding mill, whereby dispersions were prepared.

Mixed were the dispersion of 100 g of Liquid A, the dispersion of 250 g of Liquid B, and 23 g of 30% paraffin wax. The coating formulation so prepared was coated on a wood free paper to give a dry coat weight of 5.0±0.5 g/m² and then dried, whereby a heat-sensitive recording paper was produced.

Using the electron-donating chromogenic compounds and electron-attracting compounds [the compounds represented by the formula (1) or (2)], both shown in Tables 1(1) to 1(5), heat-sensitive recording papers were produced in the manner described above.

TABLE 1(1)

| Ex. | Electron-donating chromogenic compound | Electron-attracting compound [Compound of formula (1) or (2)] |
|---|---|---|
| 1 | 3-Di-n-butylamino-6-methyl-7-anilinofluoran | Exemplified Compound No. 1 |
| 2 | 3-Diethylamino-6-methyl-7-anilinofluoran | Exemplified Compound No. 18 |
| 3 | 3-Di-n-butylamino-6-methyl-7-anilinofluoran | Exemplified Compound No. 24 |
| 4 | 3-N-isopentyl-N-ethylamino-6-methyl-7-anilinofluoran | Exemplified Compound No. 28 |
| 5 | 3-Di-n-butylamino-6-methyl-7-anilinofluoran | Exemplified Compound No. 33 |
| 6 | 3-N-isopentyl-N-ethylamino-6-methyl-7-anilinofluoran | Exemplified Compound No. 66 |
| 7 | 3-N-isopentyl-N-ethylamino-6-methyl-7-anilinofluoran | Exemplified Compound No. 70 |
| 8 | 3-N-isopentyl-N-ethylamino-6-methyl-7-anilinofluoran | Exemplified Compound No. 77 |
| 9 | 3-N-n-propyl-N-methylamino-6-methyl-7-anilinofluoran | Exemplified Compound No. 78 |

TABLE 1(2)

| Ex. | Electron-donating chromogenic compound | Electron-attracting compound [Compound of formula (1) or (2)] |
|---|---|---|
| 10 | 3-N-isobutyl-N-methylamino-6-methyl-7-anilinofluoran | Exemplified Compound No. 96 |
| 11 | 3-di-n-butylamino-6-methyl-7-anilinofluoran | Exemplified Compound No. 98 |
| 12 | 3-N-isopentyl-N-ethylamino-6-methyl-7-anilinofluoran | Exemplified Compound No. 99 |
| 13 | 3-Di-n-butylamino-6-methyl-7-anilinofluoran | Exemplified Compound No. 24 & Exemplified Compound No. 70 (50%:50%) |
| 14 | 3-Di-n-butylamino-6-methyl 7-anilinofluoran | Exemplified Compound No. 117 |
| 15 | 3-Diethylamino-6-methyl-7-anilinofluoran | Exemplified Compound No. 119 |
| 16 | 3-Di-n-butylamino-6-methyl-7-anilinofluoran | Exemplified Compound No. 120 |
| 17 | 3-N-isopentyl-N-ethylamino--6-methyl-7-anilinofluoran | Exemplified Compound No. 121 |

TABLE 1(3)

| Ex. | Electron-donating chromogenic compound | Electron-attracting compound [Compound of formula (1) or (2)] |
|---|---|---|
| 18 | 3-Di-n-butylamino-6-methyl-7-anilinofluoran | Exemplified Compound No. 122 |
| 19 | 3-N-isopentyl-N-ethylamino-6-methyl-7-anilinofluoran | Exemplified Compound No. 125 |
| 20 | 3-N-isopentyl-N-ethylamino-6-methyl-7-anilinofluoran | Exemplified Compound No. 126 |
| 21 | 3-N-isopentyl-N-ethylamino-6-methyl-7-anilinofluoran | Exemplified Compound No. 128 |
| 22 | 3-N-n-propyl-N-methylamino-6-methyl-7-anilinofluoran | Exemplified Compound No. 131 |
| 23 | 3-N-isobutyl-N-methylamino-6-methyl-7-anilinofluoran | Exemplified Compound No. 136 |
| 24 | 3-Di-n-butylamino-6-methyl-7-anilinofluoran | Exemplified Compound No. 137 |
| 25 | 3-N-isopentyl-N-ethylamino-6-methyl-7-anilinofluoran | Exemplified Compound No. 140 |

TABLE 1(4)

| Ex. | Electron-donating chromogenic compound | Electron-attracting compound [Compound of formula (1) or (2)] |
|---|---|---|
| 26 | 3-Di-n-butylamino-6-methyl-7-anilinofluoran | Exemplified Compound No. 120 & Exemplified Compound No. 126 (50%:50%) |
| 27 | 3-Di-n-butylamino-6-methyl-7-anilinofluoran | Exemplified Compound No. 158 |
| 28 | 3-N-2'-methoxyethyl-N-isobutylamino-6-methyl-7-anilinofluoran | Exemplified Compound No. 165 |
| 29 | 3-N-isopentyl-N-ethylamino-6-methyl-7-anilinofluoran | Exemplified Compound No. 172 |
| 30 | 3-Di-n-butylamino-6-methyl-7-anilinofluoran | Exemplified Compound No. 221 |
| 31 | 3-Di-n-butylamino-7-(2-chloroanilino)fluoran | Exemplified Compound No. 234 |
| 32 | 3-Di-n-butylamino-6-methyl-7-anilinofluoran | Exemplified Compound No. 281 |
| 33 | 3-N-isopentyl-N-ethylamino-6-methyl-7-anilinofluoran | Exemplified Compound No. 352 |

TABLE 1(5)

| Ex. | Electron-donating chromogenic compound | Electron-attracting compound [Compound of formula (1) or (2)] |
|---|---|---|
| 34 | 3-Di-n-butylamino-6-methyl-7-anilinofluoran | Exemplified Compound No. 381 |

Comparative Examples 1-8

In each comparative example, heat-sensitive recording paper was produced in the above-described manner by using the electron-donating chromogenic compound and electron-attracting compound shown in Table 2.

TABLE 2(1)

| Comp. Ex. | Electron-donating chromogenic compound | Electron-attracting compound |
|---|---|---|
| 1 | 3-Di-n-butylamino-6-methyl-7-anilinofluoran | Bisphenol A |
| 2 | 3-Di-n-butylamino-6-methyl-7-anilinofluoran | Benzyl 4-hydroxybenzoate |
| 3 | 3-N-isopentyl-N-ethylamino-6-methyl-7-anilinofluoran | 4-Benzyloxyphenol |

TABLE 2(2)

| Comp. Ex. | Electron-donating chromogenic compound | Electron-attracting compound |
|---|---|---|
| 4 | 3-Di-n-butylamino-6-methyl-7-anilinofluoran | 4-Hydroxybenzophenone |
| 5 | 3-Di-n-butylamino-6-methyl-7-anilinofluoran | 3-Ethoxycarbonylaminophenol |
| 6 | 3-Di-n-butylamino-6-methyl-7-anilinofluoran | 4-Phenoxycarbonylaminophenol |
| 7 | 3-Di-n-butylamino-6-methyl-7-anilinofluoran | 4-tert-Butylphenyloxycarbonylaminobenzene |
| 8 | 3-Di-n-butylamino-6-methyl-7-anilinofluoran | 2,4-Bis(4'-tert-butylphenyloxycarbonylamino toluene |

Tables 3(1) to 3(3) present the results of incubation and waterproofness tests of color images produced on the heat-sensitive recording papers obtained in Examples 1–34 and Comparative Examples 1–6, respectively, and also show whether the color images were subjected to whitening or not.

TABLE 3(1)

Storage Stability Test of Produced Color Image

| Heat-sensitive recording paper | Percent remainder after hydrothermoresistance test (%) | Percent remainder after waterproofness test (%) | Whitening |
|---|---|---|---|
| Example 1 | 94 | 92 | Not occurred |
| Example 2 | 96 | 95 | Not occurred |
| Example 3 | 98 | 98 | Not occurred |
| Example 4 | 98 | 96 | Not occurred |
| Example 5 | 100 | 97 | Not occurred |
| Example 6 | 95 | 93 | Not occurred |
| Example 7 | 100 | 97 | Not occurred |
| Example 8 | 98 | 96 | Not occurred |
| Example 9 | 99 | 97 | Not occurred |
| Example 10 | 98 | 97 | Not occurred |
| Example 11 | 99 | 98 | Not occurred |
| Example 12 | 98 | 97 | Not occurred |
| Example 13 | 98 | 96 | Not occurred |
| Example 14 | 81 | 90 | Not occurred |
| Example 15 | 96 | 92 | Not occurred |
| Example 16 | 98 | 94 | Not occurred |
| Example 17 | 91 | 91 | Not occurred |
| Example 18 | 79 | 93 | Not occurred |
| Example 19 | 100 | 89 | Not occurred |

TABLE 3(2)

Storage Stability Test of Produced Color Image

| Heat-sensitive recording paper | Percent remainder after hydrothermoresistance test (%) | Percent remainder after waterproofness test (%) | Whitening |
|---|---|---|---|
| Example 20 | 100 | 95 | Not occurred |
| Example 21 | 97 | 91 | Not occurred |
| Example 22 | 100 | 96 | Not occurred |
| Example 23 | 99 | 100 | Not occurred |
| Example 24 | 98 | 93 | Not occurred |
| Example 25 | 100 | 100 | Not occurred |
| Example 26 | 96 | 96 | Not occurred |
| Example 27 | 89 | 88 | Not occurred |
| Example 28 | 88 | 89 | Not occurred |
| Example 29 | 89 | 86 | Not occurred |
| Example 30 | 90 | 85 | Not occurred |
| Example 31 | 87 | 89 | Not occurred |
| Example 32 | 90 | 88 | Not occurred |
| Example 33 | 88 | 89 | Not occurred |
| Example 34 | 87 | 87 | Not occurred |

TABLE 3(3)

Storage Stability Test of Produced Color Image

| Heat-sensitive recording paper | Percent remainder after hydrothermoresistance test (%) | Percent remainder after waterproofness test (%) | Whitening |
|---|---|---|---|
| Comp. Ex. 1 | 36 | 38 | Not occurred |
| Comp. Ex. 2 | 26 | 25 | Occurred |
| Comp. Ex. 3 | 30 | 25 | Occurred |
| Comp. Ex. 4 | 24 | 20 | Not occurred |
| Comp. Ex. 5 | 28 | 18 | Not occurred |
| Comp. Ex. 6 | 30 | 21 | Not occurred |

As is apparent from Tables 3(1) to 3(3), the heat-sensitive recording papers of the present invention, which used the compound represented by the formula (1) or (2) as an electron-attracting compound, are extremely superior in the storage stability (hydrothermoresistance and waterproofness) of produced color images compared with the heat-sensitive recording materials produced using the conventional electro-attracting compound.

Tables 4(1) to 4(3) present the results of a color-producing performance test of the heat-sensitive recording papers obtained in Examples 1-34 and Comparative Examples 7-8.

TABLE 4(1)

| Color-Producing Performance Test | | |
|---|---|---|
| Heat-sensitive recording paper | Density of color-unproduced area | Density of produced color image |
| Example 1 | 0.04 | 1.15 |
| Example 2 | 0.04 | 1.16 |
| Example 3 | 0.04 | 1.17 |
| Example 4 | 0.04 | 1.15 |
| Example 5 | 0.04 | 1.16 |
| Example 6 | 0.04 | 1.16 |
| Example 7 | 0.04 | 1.16 |
| Example 8 | 0.04 | 1.15 |
| Example 9 | 0.04 | 1.16 |
| Example 10 | 0.04 | 1.15 |
| Example 11 | 0.04 | 1.17 |
| Example 12 | 0.04 | 1.17 |
| Example 13 | 0.04 | 1.16 |
| Example 14 | 0.04 | 1.15 |
| Example 15 | 0.04 | 1.16 |
| Example 16 | 0.04 | 1.17 |
| Example 17 | 0.04 | 1.15 |
| Example 18 | 0.04 | 1.16 |

TABLE 4(2)

| Color-Producing Performance Test | | |
|---|---|---|
| Heat-sensitive recording paper | Density of color-unproduced area | Density of produced color image |
| Example 19 | 0.04 | 1.16 |
| Example 20 | 0.04 | 1.16 |
| Example 21 | 0.04 | 1.15 |
| Example 22 | 0.04 | 1.16 |
| Example 23 | 0.04 | 1.15 |
| Example 24 | 0.04 | 1.17 |
| Example 25 | 0.04 | 1.17 |
| Example 26 | 0.04 | 1.16 |
| Example 27 | 0.04 | 1.15 |
| Example 28 | 0.04 | 1.14 |
| Example 29 | 0.04 | 1.14 |
| Example 30 | 0.04 | 1.15 |
| Example 31 | 0.04 | 1.16 |
| Example 32 | 0.04 | 1.16 |
| Example 33 | 0.04 | 1.15 |
| Example 34 | 0.04 | 1.17 |
| Comp. Ex. 7 | 0.04 | 0.04 |
| Comp. Ex. 8 | 0.04 | 0.04 |

As is evident from Tables 4(1) to 4(3), carbamate compounds without any intramolecular hydroxyl group can be considered to have absolutely no color-producing ability and to have practically no function as color-attracting compounds.

It is understood, on the other hand, that the compounds of this invention, which are represented by the formula (1) or (2), namely, the compounds with intramolecular hydroxyl and carbamate groups are electron-attracting compounds having valuable practical utility.

Table 5 presents the results of a color-producing performance test of the heat-sensitive recording materials, which were obtained in Examples 3, 15, 27 and 32 and Comparative Example 1, at varied temperatures.

TABLE 5

| Color-Producing Performance Test at Varied Temperature | | | | | | |
|---|---|---|---|---|---|---|
| Heat-sensitive recording paper | Temperature (°C.) | | | | | |
| | 100 | 105 | 110 | 115 | 120 | 130 |
| Example 3 | 0.04 | 0.25 | 0.82 | 1.05 | 1.17 | 1.17 |
| Example 15 | 0.05 | 0.28 | 0.80 | 1.06 | 1.15 | 1.15 |
| Example 27 | 0.05 | 0.26 | 0.80 | 1.04 | 1.15 | 1.15 |
| Example 32 | 0.04 | 0.27 | 0.83 | 1.06 | 1.16 | 1.16 |
| Comp. Ex. 1 | 0.05 | 0.10 | 0.15 | 0.21 | 0.35 | 1.10 |

As is clearly envisaged from Table 5, the heat-sensitive recording materials according to the present invention promptly produced the color at lower temperatures than the heat-sensitive recording material using the conventional electron-attracting compound and are considered to be heat-sensitive recording materials of high sensitivity suited for high-speed recording.

EXAMPLES 35-71

(Production method of heat-sensitive recording papers)

(Composition of Liquid A')

| | |
|---|---|
| Electron-donating chromogenic compound | 10 g |
| 10% Aqueous solution of polyvinyl alcohol ("Kuraray-117", trade name; product of Kuraray Co., Ltd.) | 10 g |
| Water | 80 g |
| Total | 100 g |

(Composition of Liquid B')

| | |
|---|---|
| Electron-attracting compound (bisphenol-A) | 20 g |
| Precipitated calcium carbonate ("TP-123", trade name; product of Okutama Kogyo K.K.) | 40 g |
| 10% Aqueous solution of polyvinyl alcohol ("Kuraray-117", trade name; product of Kutaray Co., Ltd.) | 60 g |
| Water | 130 g |
| Total | 250 g |

(Composition of Liquid C')

| | |
|---|---|
| Compound of formula (1) or (2) | 20 g |
| 10% Aqueous solution of polyvinyl alcohol ("Kuraray-117", trade name; product of Kuraray Co., Ltd.) | 10 g |
| Water | 220 g |
| Total | 250 g |

Liquid A'-Liquid B' and Liquid C' were separately dispersed to an average particle size of 1.5 μm or smaller in a sand grinding mill, whereby dispersions were prepared.

Mixed were the dispersion of 100 g of Liquid A', the dispersion of 250 g of Liquid B', the dispersion of 250 g of Liquid C' and 23 g of 30% paraffin wax. The coating formulation so prepared was coated on a wood free paper to give a dry coat weight of 5.0±0.5 g/m² and then dried, whereby a heat-sensitive recording paper was produced.

Using the electron-donating chromogenic compounds and the compounds represented by the formula (1) or (2), both shown in Tables 6(1) to 6(5), heat-sensitive recording papers were produced in the manner described above.

TABLE 6

| Ex. | Electron-donating chromogenic compound | Compound of formula (1) or (2) |
|---|---|---|
| 35 | 3-Di-n-butylamino-6-methyl- | Exemplified |

TABLE 6-continued

| Ex. | Electron-donating chromogenic compound | Compound of formula (1) or (2) |
|---|---|---|
|  | 7-anilinofluoran | Compound No. 1 |
| 36 | 3-Diethylamino-6-methyl-7-anilinofluoran | Exemplified Compound No. 18 |
| 37 | 3-Di-n-butylamino-6-methyl-7-anilinofluoran | Exemplified Compound No. 24 |

TABLE 6(2)

| Ex. | Electron-donating chromogenic compound | Compound of formula (1) or (2) |
|---|---|---|
| 38 | 3-N-isopentyl-N-ethylamino-6-methyl-7-anilinofluoran | Exemplified Compound No. 28 |
| 39 | 3-Di-n-butylamino-6-methyl-7-anilinofluoran | Exemplified Compound No. 33 |
| 40 | 3-N-isopentyl-N-ethylamino-6-methyl-7-anilinofluoran | Exemplified Compound No. 66 |
| 41 | 3-N-isopentyl-N-ethylamino-6-methyl-7-anilinofluoran | Exemplified Compound No. 70 |
| 42 | 3-N-isopentyl-N-ethylamino-6-methyl-7-anilinofluoran | Exemplified Compound No. 77 |
| 43 | 3-N-n-propyl-N-methylamino-6-methyl-7-anilinofluoran | Exemplified Compound No. 78 |
| 44 | 3-N-isobutyl-N-methylamino-6-methyl-7-anilinofluoran | Exemplified Compound No. 96 |
| 45 | 3-Di-n-butylamino-6-methyl-7-anilinofluoran | Exemplified Compound No. 98 |
| 46 | 3-N-isopentyl-N-ethylamino-6-methyl-7-anilinofluoran | Exemplified Compound No. 99 |

TABLE 6(3)

| Ex. | Electron-donating chromogenic compound | Compound of formula (1) or (2) |
|---|---|---|
| 47 | 3-Di-n-butylamino-6-methyl 7-anilinofluoran | Exemplified Compound No. 24 & Exemplified Compound No. 70 (50%:50%) |
| 48 | 3-Di-n-butylamino-6-methyl 7-anilinofluoran | Exemplified Compound No. 117 |
| 49 | 3-Diethylamino-6-methyl-7-anilinofluoran | Exemplified Compound No. 119 |
| 50 | 3-Di-n-butylamino-6-methyl-7-anilinofluoran | Exemplified Compound No. 120 |
| 51 | 3-N-isopentyl-N-ethylamino--6-methyl-7-anilinofluoran | Exemplified Compound No. 121 |
| 52 | 3-Di-n-butylamino-6-methyl-7-anilinofluoran | Exemplified Compound No. 122 |
| 53 | 3-N-isopentyl-N-ethylamino-6-methyl-7-anilinofluoran | Exemplified Compound No. 125 |
| 54 | 3-N-isopentyl-N-ethylamino-6-methyl-7-anilinofluoran | Exemplified Compound No. 126 |
| 55 | 3-N-isopentyl-N-ethylamino-6-methyl-7-anilinofluoran | Exemplified Compound No. 128 |

TABLE 6(4)

| Ex. | Electron-donating chromogenic compound | Compound of formula (1) or (2) |
|---|---|---|
| 56 | 3-N-n-propyl-N-methylamino-6-methyl-7-anilinofluoran | Exemplified Compound No. 131 |
| 57 | 3-N-isobutyl-N-methylamino-6-methyl-7-anilinofluoran | Exemplified Compound No. 136 |
| 58 | 3-Di-n-butylamino-6-methyl-7-anilinofluoran | Exemplified Compound No. 137 |
| 59 | 3-N-isopentyl-N-ethylamino-6-methyl-7-anilinofluoran | Exemplified Compound No. 140 |
| 60 | 3-Di-n-butylamino-6-methyl 7-anilinofluoran | Exemplified Compound No. 120 & Exemplified Compound No. 126 (50%:50%) |
| 61 | 3-Di-n-butylamino-6-methyl-7-anilinofluoran | Exemplified Compound No. 158 |
| 62 | 3-N-2'-methoxyethyl-N-isobutylamino-6-methyl-7-anilinofluoran | Exemplified Compound No. 165 |
| 63 | 3-N-isopentyl-N-ethylamino-6-methyl-7-anilinofluoran | Exemplified Compound No. 172 |
| 64 | 3-Di-n-butylamino-6-methyl-7-anilinofluoran | Exemplified Compound No. 193 |

TABLE 6(5)

| Ex. | Electron-donating chromogenic compound | Compound of formula (1) or (2) |
|---|---|---|
| 65 | 3-N-isopentyl-N-ethylamino-6-methyl-7-anilinofluoran | Exemplified Compound No. 194 |
| 66 | 3-Di-n-butylamino-6-methyl-7-anilinofluoran | Exemplified Compound No. 221 |
| 67 | 3-Di-n-butylamino-7-(2-chloroanilino)fluoran | Exemplified Compound No. 234 |
| 68 | 3-Di-n-butylamino-6-methyl-7-anilinofluoran | Exemplified Compound No. 281 |
| 69 | 3-Di-n-butylamino-6-methyl-7-anilinofluoran | Exemplified Compound No. 358 |
| 70 | 3-Di-n-butylamino-6-methyl-7-anilinofluoran | Exemplified Compound No. 375 |
| 71 | 3-Di-n-butylamino-6-methyl-7-anilinofluoran | Exemplified Compound No. 381 |

Comparative Examples 9–10

In each comparative example, heat-sensitive recording paper was produced in the above-described manner by using the electron-donating chromogenic compound shown in Table 7 and Liquids A' and B' without using Liquid C'.

TABLE 7

| Comp. Ex. | Electron-donating chromogenic compound |
|---|---|
| 9 | 3-Di-n-butylamino-6-methyl-7-anilinofluoran |
| 10 | 3-N-isopentyl-N-ethylamino-6-methyl-7-anilinofluoran |

Comparative Examples 11–19

In each comparative example, heat-sensitive recording paper was produced in substantially the same manner as described above except that 3-di-n-butylamino-6-methyl-7-anilinofluoran was used as the electron-donating chromogenic compound in Liquid A' and the compound shown in Table 8 was used in place of the compound of the general formula (1) or (2) in Liquid C'.

TABLE 8

| Comp. Ex. | Compound in Liquid C' |
|---|---|
| 11 | 4-Benzylbiphenyl |
| 12 | m-Terphenyl |
| 13 | 3-Ethoxycarbonylaminophenol |
| 14 | 4-Phenyloxycarbonylaminophenol |
| 15 | 4-tert-Butylphenyloxycarbonylaminobenzene |
| 16 | 4-Cumylphenyloxycarbonylaminobenzene |
| 17 | 1,6-Bis(phenyloxycarbonylamino)hexane |
| 18 | 1,1-Bis(4-ethoxycarbonylaminophenyl)- |

TABLE 8-continued

| Comp. Ex. | Compound in Liquid C' |
|---|---|
| 19 | methane Di-(4-ethoxycarbonylaminophenyl)ether |

Tables 9(1) to 9(3) present the results of incubation, waterproofness and oil resistance tests of color images produced on the heat-sensitive recording papers obtained in Examples 35-71 and Comparative Examples 9-19.

TABLE 9(1)

Storage Stability Test of Produced Color Image

| Heat-sensitive recording paper | Percent remainder after hydrothermo-resistance test (%) | Percent remainder after waterproofness test (%) | Percent remainder after oil resistance test (%) |
|---|---|---|---|
| Example 35 | 100 | 98 | 99 |
| Example 36 | 100 | 97 | 96 |
| Example 37 | 99 | 97 | 98 |
| Example 38 | 99 | 100 | 98 |
| Example 39 | 100 | 97 | 99 |
| Example 40 | 98 | 99 | 99 |
| Example 41 | 100 | 97 | 100 |
| Example 42 | 98 | 96 | 97 |
| Example 43 | 100 | 97 | 99 |
| Example 44 | 98 | 99 | 99 |
| Example 45 | 100 | 98 | 99 |
| Example 46 | 99 | 97 | 98 |
| Example 47 | 98 | 98 | 98 |

TABLE 9(2)

Storage Stability Test of Produced Color Image

| Heat-sensitive recording paper | Percent remainder after hydrothermo-resistance test (%) | Percent remainder after waterproofness test (%) | Percent remainder after oil resistance test (%) |
|---|---|---|---|
| Example 48 | 81 | 90 | 90 |
| Example 49 | 96 | 90 | 94 |
| Example 50 | 98 | 92 | 94 |
| Example 51 | 91 | 94 | 96 |
| Example 52 | 79 | 91 | 95 |
| Example 53 | 100 | 93 | 99 |
| Example 54 | 100 | 89 | 85 |
| Example 55 | 97 | 95 | 96 |
| Example 56 | 100 | 91 | 100 |
| Example 57 | 99 | 96 | 98 |
| Example 58 | 98 | 100 | 89 |
| Example 59 | 100 | 93 | 92 |
| Example 60 | 96 | 96 | 93 |
| Example 61 | 95 | 93 | 90 |
| Example 62 | 95 | 94 | 89 |
| Example 63 | 96 | 94 | 88 |
| Example 64 | 98 | 93 | 90 |
| Example 65 | 98 | 92 | 91 |
| Example 66 | 97 | 90 | 90 |

TABLE 9(3)

Storage Stability Test of Produced Color Image

| Heat-sensitive recording paper | Percent remainder after hydrothermo-resistance test (%) | Percent remainder after waterproofness test (%) | Percent remainder after oil resistance test (%) |
|---|---|---|---|
| Example 67 | 95 | 92 | 86 |
| Example 68 | 95 | 91 | 88 |
| Example 69 | 94 | 92 | 90 |
| Example 70 | 94 | 93 | 87 |
| Example 71 | 90 | 90 | 91 |
| Comp. Ex. 9 | 36 | 38 | 20 |
| Comp. Ex. 10 | 42 | 45 | 29 |
| Comp. Ex. 11 | 18 | 15 | 16 |
| Comp. Ex. 12 | 16 | 13 | 12 |
| Comp. Ex. 13 | 19 | 18 | 11 |
| Comp. Ex. 14 | 20 | 19 | 15 |
| Comp. Ex. 15 | 21 | 20 | 17 |
| Comp. Ex. 16 | 23 | 21 | 19 |
| Comp. Ex. 17 | 22 | 20 | 16 |
| Comp. Ex. 18 | 20 | 17 | 17 |
| Comp. Ex. 19 | 19 | 18 | 18 |

As is apparent from Tables 9(1) to 9(3), the heat-sensitive recording materials according to the present invention are excellent in the storage stability (hydrothermoresistance, waterproofness and oil resistance) of produced color images.

Table 10 shows the results of a color-producing performance test of the heat-sensitive recording papers, which were obtained in Examples 37, 49, 61 and 68 and Comparative Example 9, at varied temperatures.

TABLE 10

Color-Producing Performance Test at Varied Temperatures

| Heat-sensitive recording paper | Temperature (°C.) | | | | | |
|---|---|---|---|---|---|---|
| | 95 | 100 | 105 | 110 | 120 | 130 |
| Example 37 | 0.10 | 0.68 | 1.10 | 1.26 | 1.35 | 1.35 |
| Example 49 | 0.10 | 0.68 | 1.10 | 1.26 | 1.35 | 1.35 |
| Example 61 | 0.10 | 0.66 | 1.11 | 1.20 | 1.35 | 1.35 |
| Example 68 | 0.10 | 0.65 | 1.12 | 1.22 | 1.35 | 1.35 |
| Comp. Ex. 9 | 0.05 | 0.05 | 0.10 | 0.15 | 0.35 | 1.10 |

As is understood clearly from Table 10, the heat-sensitive sensitive recording materials according to the present invention promptly produced the color at lower temperatures than the heat-sensitive recording material composed of the conventional electron-attracting chromogenic compound and electron-attracting compound and are considered to be heat-sensitive recording materials of high sensitivity suitable for high-speed recording.

EXAMPLES 72-108

(Production method of heat-sensitive recording papers)

In each example, heat-sensitive recording paper was produced in the above-described manner by using 100 g of Liquid A'', 250 g of Liquid B'', 250 g of Liquid C'' and 23 g of 30% paraffin wax Liquids A'', B'' and C'' had been prepared using the electron-donating chromogenic compound, thermofusible compound and the compound of the formula (1) or (2), all shown in Table 11.

(Composition of Liquid A'')

| | |
|---|---|
| Electron-donating chromogenic compound | 10 g |
| 10% Aqueous solution of polyvinyl alcohol ("Kuraray-117", trade name; product of Kuraray Co., Ltd.) | 10 g |
| Water | 80 g |
| Total | 100 g |

(Composition of Liquid B'')

| | |
|---|---|
| Electron-attracting compound (bisphenol-A) | 20 g |
| Precipitated calcium carbonate ("TP-123", trade name; product of Okutama Kogyo K.K.) | 40 g |

-continued

| | |
|---|---|
| 10% Aqueous solution of polyvinyl alcohol ("Kuraray-117", trade name; product of Kuraray Co., Ltd.) | 60 g |
| Water | 130 g |
| | Total 250 g |
| (Composition of Liquid C") | |
| Thermofusible compound | 5 g |
| Compound of formula (1) or (2) | 15 g |
| 10% Aqueous solution of polyvinyl alcohol ("Kuraray-117", trade name; product of Kuraray Co., Ltd.) | 10 g |
| Water | 220 g |
| | Total 250 g |

TABLE 11(1)

| Ex. | Electron-donating chromogenic compound | Thermo-fusible compound | Compound of formula (1) or (2) |
|---|---|---|---|
| 72 | 3-Di-n-butylamino-6-methyl-7-anilinofluoran | A | Exemplified Compound No. 1 |
| 73 | 3-Diethylamino-6-methyl-7-anilinofluoran | A | Exemplified Compound No. 18 |

TABLE 11(2)

| Ex. | Electron-donating chromogenic compound | Thermo-fusible compound | Compound of formula (1) or (2) |
|---|---|---|---|
| 74 | 3-Di-n-butylamino-6-methyl-7-anilinofluoran | A | Exemplified Compound No. 24 |
| 75 | 3-N-isopentyl-N-ethylamino-6-methyl-7-anilinofluoran | A | Exemplified Compound No. 28 |
| 76 | 3-Di-n-butylamino-6-methyl-7-anilinofluoran | B | Exemplified Compound No. 33 |
| 77 | 3-N-isopentyl-N-ethylamino-6-methyl-7-anilinofluoran | C | Exemplified Compound No. 66 |
| 78 | 3-N-isopentyl-N-ethylamino-6-methyl-7-anilinofluoran | D | Exemplified Compound No. 70 |
| 79 | 3-N-isopentyl-N-ethylamino-6-methyl-7-anilinofluoran | C | Exemplified Compound No. 77 |
| 80 | 3-N-n-propyl-N-methylamino-6-methyl-7-anilinofluoran | A | Exemplified Compound No. 78 |
| 81 | 3-N-Isobutyl-N-methylamino-6-methyl-7-anilinofluoran | E | Exemplified Compound No. 96 |
| 82 | 3-Di-n-butylamino-6-methyl-7-anilinofluoran | D | Exemplified Compound No. 98 |
| 83 | 3-N-Isopentyl-N-ethylamino-6-methyl-7-anilinofluoran | D | Exemplified Compound No. 99 |

TABLE 11(3)

| Ex. | Electron-donating chromogenic compound | Thermo-fusible compound | Compound of formula (1) or (2) |
|---|---|---|---|
| 84 | 3-Di-n-butylamino-6-methyl-7-anilinofluoran | D | Exemplified Compound No. 24 & Exemplified Compound No. 70 (50%:50%) |
| 85 | 3-Di-n-butylamino-6-methyl-7-anilinofluoran | A | Exemplified Compound No. 117 |
| 86 | 3-Diethylamino-6-methyl-7-anilinofluoran | A | Exemplified Compound No. 119 |
| 87 | 3-Di-n-butylamino-6-methyl-7-anilinofluoran | A | Exemplified Compound No. 120 |
| 88 | 3-N-Isopentyl-N-ethylamino-6-methyl-7-anilinofluoran | A | Exemplified Compound No. 121 |
| 89 | 3-Di-n-butylamino-6-methyl-7-anilinofluoran | B | Exemplified Compound No. 122 |
| 90 | 3-N-Isopentyl-N-ethylamino-6-methyl-7-anilinofluoran | C | Exemplified Compound No. 125 |
| 91 | 3-N-Isopentyl-N-ethylamino-6-methyl-7-anilinofluoran | D | Exemplified Compound No. 126 |
| 92 | 3-N-Isopentyl-N-ethylamino-6-methyl-7-anilinofluoran | C | Exemplified Compound No. 128 |

TABLE 11(4)

| Ex. | Electron-donating chromogenic compound | Thermo-fusible compound | Compound of formula (1) or (2) |
|---|---|---|---|
| 93 | 3-N-n-Propyl-N-methylamino-6-methyl-7-anilinofluoran | A | Exemplified Compound No. 131 |
| 94 | 3-N-Isobutyl-N-methylamino-6-methyl-7-anilinofluoran | E | Exemplified Compound No. 136 |
| 95 | 3-Di-n-butylamino-6-methyl-7-anilinofluoran | D | Exemplified Compound No. 137 |
| 96 | 3-N-Isopentyl-N-ethylamino-6-methyl-7-anilinofluoran | D | Exemplified Compound No. 140 |
| 97 | 3-Di-n-butylamino-6-methyl-7-anilinofluoran | D | Exemplified Compound No. 120 & Exemplified Compound No. 126 (50%:50%) |
| 98 | 3-Di-n-butylamino-6-methyl-7-anilinofluoran | A | Exemplified Compound No. 158 |
| 99 | 3-N-2'-methoxyethyl-N-iso-butylamino-6-methyl-7-anilinofluoran | A | Exemplified Compound No. 165 |
| 100 | 3-N-isopentyl-N-ethylamino-6-methyl-7-anilinofluoran | B | Exemplified Compound No. 172 |
| 101 | 3-Di-n-butylamino-6-methyl-7-anilinofluoran | C | Exemplified Compound No. 193 |

TABLE 11(5)

| Ex. | Electron-donating chromogenic compound | Thermo-fusible compound | Compound of formula (1) or (2) |
|---|---|---|---|
| 102 | 3-N-isopentyl-N-ethylamino-6-methyl-7-anilinofluoran | D | Exemplified Compound No. 194 |
| 103 | 3-Di-n-butylamino-6-methyl-7-anilinofluoran | E | Exemplified Compound No. 221 |
| 104 | 3-Di-n-butylamino-7-(2-chloroanilino)fluoran | A | Exemplified Compound No. 234 |
| 105 | 3-Di-n-butylamino-6-methyl-7-anilinofluoran | A | Exemplified Compound No. 281 |
| 106 | 3-Di-n-butylamino-6-methyl-7-anilinofluoran | A | Exemplified Compound No. |

TABLE 11(5)-continued

| Ex. | Electron-donating chromogenic compound | Thermo-fusible compound | Compound of formula (1) or (2) |
|---|---|---|---|
| 107 | 3-Di-n-butylamino-6-methyl-7-anilinofluoran | A | Exemplified Compound No. 358 |
| 108 | 3-Di-n-butylamino-6-methyl-7-anilinofluoran | A | Exemplified Compound No. 375 |
| | | | Exemplified Compound No. 381 |

Incidentally, the thermofusible compounds A, B, C, D and E used in Tables 11(1) to 11(5) indicate the following compounds:
A: 2-Benzyloxynaphthalene
B: Di(4-methylbenzyl) oxalate
C: 1,2-Bis(3'-methylphenoxy)ethane
D: 4-(4'-Methylphenoxy)biphenyl
E: 4-Benzylbiphenyl Comparative Examples 20-24

In each comparative example, heat-sensitive recording paper was produced in the above-described manner from 100 g of Liquid A", 250 g of Liquid B", 250 g of Liquid D" in place of Liquid C", and 23 g of 30% paraffin wax. Liquid A" had been prepared by employing the electron-donating chromogenic compound shown in Table 12 while Liquid D" had been obtained using the thermofusible compound shown in Table 12 in accordance with the below-described composition.

| (Composition of Liquid D") | |
|---|---|
| Thermofusible compound | 20 g |
| 10% Aqeous solution of polyvinyl alcohol ("Kuraray-117", trade name; product of Kuraray Co., Ltd.) | 10 g |
| Water | 220 g |
| | Total 250 g |

TABLE 12

| Comp. Ex. | Electron-donating chromogenic compound | Thermofusible substance |
|---|---|---|
| 20 | 3-Di-n-butylamino-6-methyl-7-anilinofluoran | A |
| 21 | 3-N-Isopentyl-N-ethylamino-6-methyl-7-anilinofluoran | A |
| 22 | 3-Di-n-butylamino-6-methyl-7-anilinofluoran | B |
| 23 | 3-Di-n-butylamino-6-methyl-7-anilinofluoran | C |
| 24 | 3-Di-n-butylamino-6-methyl-7-anilinofluoran | D |

Incidentally, the thermofusible compounds A, B, C and D employed in Table 12 indicate the following compounds:
A: 2-Benzyloxynaphthalene
B: Di(4-methylbenzyl) oxalate
C: 1,2-Bis(3'-methylphenoxy)ethane
D: 4-(4'-Methylphenoxy)biphenyl Comparative Examples 25-26

In each comparative example, heat-sensitive recording paper was produced in the same manner as described above except that 3-di(n-butylamino)-6-methyl-7-anilinofluoran was used as the electron-donating chromogenic compound in Liquid A" and 3-ethoxycarbonylaminophenol (Comparative Example 25) or 4-phenyloxycarbonylaminobenzene (Comparative Example 26) was employed instead of the compound of the formula (1) or (2) in Liquid C".

Tables 13(1) to 13(5) present the results of heat resistance, incubation, waterproofness and oil resistance tests of color images produced on the heat-sensitive recording papers obtained in Examples 72-108 and Comparative Examples 20-26, respectively.

TABLE 13(1)

Storage Stability Test of Produced Color Image

| Heat-sensitive recording paper | Percent remainder after heat resistance test (%) | Percent remainder after hydro-thermo-resistance test (%) | Percent remainder after water-proofness test (%) | Percent remainder after oil resistance test (%) |
|---|---|---|---|---|
| Example 72 | 93 | 86 | 84 | 89 |
| Example 73 | 91 | 88 | 85 | 84 |
| Example 74 | 93 | 88 | 87 | 86 |
| Example 75 | 92 | 90 | 86 | 84 |
| Example 76 | 94 | 87 | 86 | 89 |
| Example 77 | 91 | 91 | 88 | 87 |
| Example 78 | 90 | 90 | 86 | 84 |
| Example 79 | 93 | 91 | 86 | 87 |
| Example 80 | 90 | 88 | 90 | 89 |

TABLE 13(2)

Storage Stability Test of Produced Color Image

| Heat-sensitive recording paper | Percent remainder after heat resistance test (%) | Percent remainder after hydro-thermo-resistance test (%) | Percent remainder after water-proofness test (%) | Percent remainder after oil resistance test (%) |
|---|---|---|---|---|
| Example 81 | 90 | 86 | 84 | 83 |
| Example 82 | 91 | 85 | 85 | 86 |
| Example 83 | 93 | 88 | 87 | 88 |
| Example 84 | 90 | 90 | 88 | 88 |
| Example 85 | 90 | 88 | 88 | 89 |
| Example 86 | 93 | 86 | 87 | 88 |
| Example 87 | 91 | 90 | 85 | 88 |
| Example 88 | 90 | 98 | 84 | 86 |
| Example 89 | 90 | 85 | 90 | 83 |

TABLE 13(3)

Storage Stability Test of Produced Color Image

| Heat-sensitive recording paper | Percent remainder after heat resistance test (%) | Percent remainder after hydro-thermo-resistance test (%) | Percent remainder after water-proofness test (%) | Percent remainder after oil resistance test (%) |
|---|---|---|---|---|
| Example 90 | 93 | 86 | 86 | 89 |
| Example 91 | 90 | 88 | 86 | 87 |
| Example 92 | 91 | 91 | 88 | 84 |
| Example 93 | 94 | 90 | 86 | 89 |
| Example 94 | 92 | 91 | 86 | 84 |
| Example 95 | 93 | 87 | 87 | 86 |
| Example 96 | 91 | 90 | 85 | 84 |
| Example 97 | 93 | 88 | 84 | 87 |
| Example 98 | 90 | 88 | 84 | 83 |

TABLE 13(4)

Storage Stability Test of Produced Color Image

| Heat-sensitive recording paper | Percent remainder after heat resistance test (%) | Percent remainder after hydro-thermo-resistance test (%) | Percent remainder after water-proofness test (%) | Percent remainder after oil resistance test (%) |
|---|---|---|---|---|
| Example 99 | 89 | 87 | 83 | 82 |
| Example 100 | 88 | 87 | 82 | 82 |
| Example 101 | 89 | 86 | 85 | 82 |
| Example 102 | 91 | 85 | 83 | 82 |
| Example 103 | 90 | 84 | 82 | 82 |
| Example 104 | 88 | 83 | 82 | 82 |
| Example 105 | 90 | 88 | 84 | 83 |
| Example 106 | 94 | 87 | 85 | 84 |
| Example 107 | 90 | 88 | 85 | 84 |
| Example 108 | 91 | 90 | 89 | 88 |

TABLE 13(5)

Storage Stability Test of Produced Color Image

| Heat-sensitive recording paper | Percent remainder after heat resistance test (%) | Percent remainder after hydro-thermo-restistance test (%) | Percent remainder after water-proofness test (%) | Percent remainder after oil resistance test (%) |
|---|---|---|---|---|
| Comp. Ex. 20 | 30 | 15 | 20 | 10 |
| Comp. Ex. 21 | 42 | 28 | 32 | 21 |
| Comp. Ex. 22 | 30 | 15 | 18 | 11 |
| Comp. Ex. 23 | 29 | 17 | 16 | 12 |
| Comp. Ex. 24 | 32 | 18 | 21 | 15 |
| Comp. Ex. 25 | 30 | 19 | 18 | 14 |
| Comp. Ex. 26 | 29 | 19 | 18 | 16 |

As is clearly envisaged from Tables 13(1) to 13(5), the heat-sensitive recording materials according to the present invention are excellent in the storage stability (heat resistance, hydrothermoresistance, waterproofness and oil resistance) of produced color images.

Table 14 presents the results of a color-producing performance test of the heat-sensitive recording papers, which were obtained in Examples 74, 86, 98 and 105 and Comparative Example 20, at varied temperatures.

TABLE 14

Color-Producing Performance Test at Varied Temperatures

| Heat-sensitive recording paper | Temperature (°C.) | | | | | |
|---|---|---|---|---|---|---|
| | 75 | 80 | 85 | 90 | 95 | 100 |
| Example 74 | 0.05 | 0.10 | 0.80 | 0.93 | 1.09 | 1.21 |
| Example 86 | 0.05 | 0.10 | 0.80 | 0.93 | 1.09 | 1.21 |
| Example 98 | 0.05 | 0.11 | 0.82 | 0.95 | 1.10 | 1.20 |
| Example 105 | 0.05 | 0.11 | 0.81 | 0.92 | 1.12 | 1.22 |
| Comp. Ex. 20 | 0.05 | 0.07 | 0.10 | 0.20 | 0.92 | 1.19 |

As is understood clearly from Table 14, the heat-sensitive recording materials according to the present invention promptly produced the color at lower temperatures than the conventional heat-sensitive recording material and are considered to be heat-sensitive recording materials of high sensitivity suitable for high-speed recording.

What is claimed is:

1. A phenol compound represented by the following formula (3):

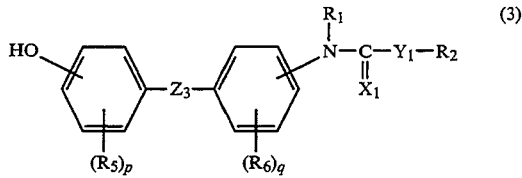

wherein $R_1$ means a hydrogen atom or an alkyl, aralkyl or aryl group, $R_2$ denotes an alkyl, alkenyl, aralkyl or aryl group, $R_5$ and $R_6$ are a hydrogen or halogen atom or an alkyl, alkoxy, aralkyl, aryl or hydroxyl group, p and q stand for an integer of 1–4, $R_5$ and $R_6$ may be either the same or different when p and q individually represent an integer of 2, or greater, $X_1$ and $Y_1$ individually represent an oxygen or sulfur atom, and $—Z_3—$ means a group containing at least one group selected from the class consisting of —O—, —S—, a phenylene group, —CO—, $—CR_{10}=CR_{11}—$, in which $R_{10}$ and $R_{11}$ are individually a hydrogen atom or an alkyl or aryl group, —SO— and —SO$_2$— or, when $R_1$ is a hydrogen atom, $—Z_3—$ may also be $—R_8CR_9—$, wherein $R_8$ and $R_9$ individually represent an alkyl group having 1–4 carbon atoms.

2. The compound of claim 1, wherein in the formula (3), $R_1$, $R_5$ and $R_6$ are each a hydrogen atom, $X_1$ is an oxygen atom, and $—Z_3—$ is $—R_8CR_9—$.

3. The compound of claim 2, wherein in the formula (3), $R_8$ and $R_9$ are each a methyl group.

4. The compound of claim 1, which is represented by one of the following formula (4-1) or (4-2):

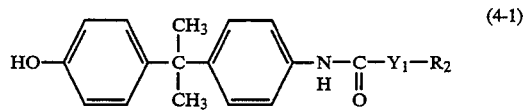

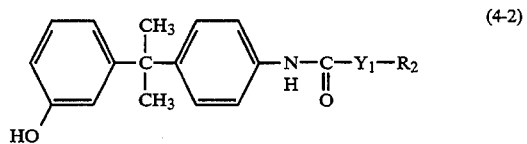

wherein $R_2$ and $Y_1$ have the same meanings as defined above.

5. A phenol compound represented by the following formula (5-0):

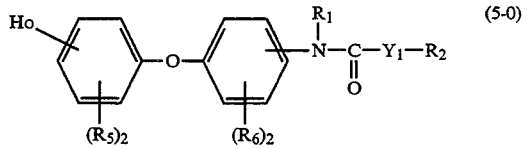

wherein $R_1$ means a hydrogen atom or an alkyl, aralkyl or aryl group, $R_2$ denotes an alkyl, alkenyl, aralkyl or aryl group, $R_5$ and $R_6$ are either the same or different and individually represent a hydrogen or halogen atom, or an alkyl, alkoxy, aralkyl, aryl or hydroxyl group, and $Y_1$ represents an oxygen or sulfur atom.

6. The compound of claim 5, wherein in the formula (5-0), $R_1$, $R_5$ and $R_6$ are each a hydrogen atom.

7. The compound of claim 6, wherein in the formula (5-0), $Y_1$ is an oxygen atom.

8. The compound of claim 6, which is represented by one of the following formulae (5-1 or 5-2):

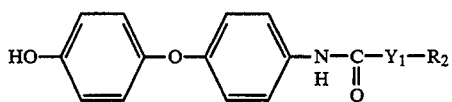
(5-1)

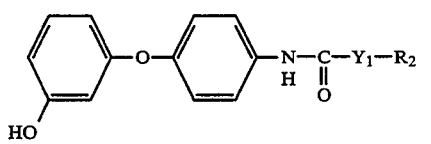
(5-2)

wherein $R_2$ and $Y_1$ have the same meanings as defined above.

9. A phenol compound represented by the following formula (6-0):

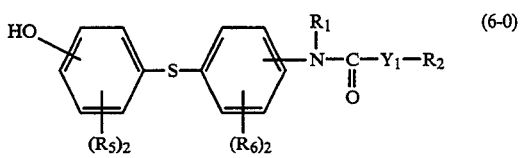
(6-0)

wherein $R_1$ means a hydrogen atom or an alkyl, aralkyl or aryl group, $R_2$ denotes an alkyl, alkenyl, aralkyl or aryl group, $R_5$ and $R_6$ are either the same or different and individually represent a hydrogen or halogen atom, or an alkyl, alkoxy, aralkyl, aryl or hydroxyl group, and $Y_1$ represents an oxygen or sulfur atom.

10. The compound of claim 9, wherein in the formula (6-0), $R_1$, $R_5$ and $R_6$ are each a hydrogen atom.

11. The compound of claim 10, wherein in the formula (6-0), $Y_1$ is an oxygen atom.

12. A compound represented by the following formula (6-1):

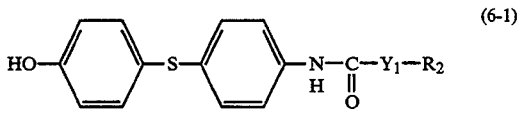
(6-1)

wherein $R_2$ is an alkyl, alkenyl, aralkyl or aryl group and $Y_1$ is an oxygen or sulfur atom.

13. A phenol compound represented by the following formula (7-0):

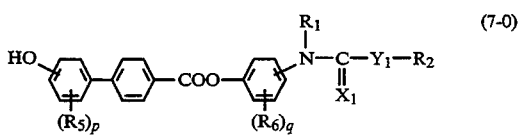
(7-0)

wherein $R_1$ means a hydrogen atom or an alkyl, aralkyl or aryl group, $R_2$ denotes an alkyl, alkenyl, aralkyl or aryl group, $R_5$ and $R_6$ are either the same or different and individually represent a hydrogen or halogen atom, or an alkyl, alkoxy, aralkyl, aryl or hydroxyl group, p and q each individually stand for an integer of 1–4, wherein $R_5$ and $R_6$ may be the same or different when p and q individually represent an integer of 2–4, and $X_1$ and $Y_1$ individually represent an oxygen or sulfur atom.

14. The compound of claim 13, wherein in the formula (7-0), $R_1$, $R_5$ and $R_6$ are each a hydrogen atom and $X_1$ is an oxygen atom.

15. The compound of claim 14, wherein in the formula (7-0), $Y_1$ is an oxygen atom.

16. A compound of claim 13, which is represented by one of the following formulae (7-1) or (7-2):

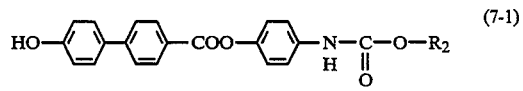
(7-1)

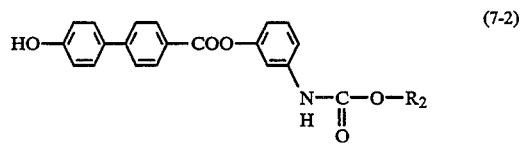
(7-2)

wherein $R_2$ has the same meaning as defined above.

17. A compound represented by the following formula (8-0):

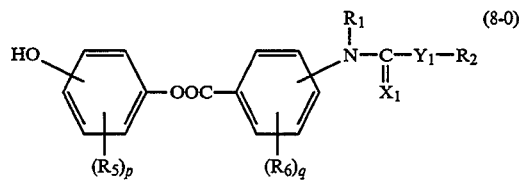
(8-0)

wherein $R_1$ means a hydrogen atom or an alkyl, aralkyl or aryl group, $R_2$ denotes an alkyl, alkenyl, aralkyl or aryl group, $R_5$ and $R_6$ are either the same or different and individually represent a hydrogen or halogen atom, or an alkyl, alkoxy, aralkyl, aryl or hydroxyl group, p and q stand for an integer of 1–4, wherein $R_5$ and $R_6$ may be the same or different when p and q individually represent an integer of 2–4, and $X_1$ and $Y_1$ individually represent an oxygen or sulfur atom.

18. The compound of claim 17, wherein in the formula (8-0), $R_1$, $R_5$ and $R_6$ are each a hydrogen atom and $X_1$ is an oxygen atom.

19. The compound of claim 18, wherein in the formula (8-0), $Y_1$ is an oxygen atom.

20. A compound of claim 17, which is represented by the following formula (8-1):

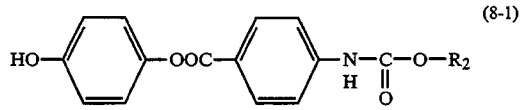
(8-1)

wherein $R_2$ has the same meaning as defined above.

* * * * *

UNITED STATES PATENT AND TRADEMARK OFFICE
CERTIFICATE OF CORRECTION

PATENT NO. : 5,391,806
DATED : February 21, 1995
INVENTOR(S) : Atsuo OTSUJI et al.

It is certified that error appears in the above-indentified patent and that said Letters Patent is hereby corrected as shown below:

Title page; Item [30], Under Foreign Application Priority Data: Change "3-370770" to - -3-340770- -.

Signed and Sealed this

Sixth Day of June, 1995

Attest:

BRUCE LEHMAN

*Attesting Officer*   *Commissioner of Patents and Trademarks*